United States Patent
Annex et al.

(10) Patent No.: US 9,845,465 B2
(45) Date of Patent: Dec. 19, 2017

(54) COMPOSITIONS AND METHODS FOR TREATING PERIPHERAL ARTERIAL DISEASE

(71) Applicant: University of Virginia Patent Foundation, Charlottesville, VA (US)

(72) Inventors: Brian H. Annex, Charlottesville, VA (US); Charles R. Farber, Charlottesville, VA (US); Surovi Hazarika, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 62 days.

(21) Appl. No.: 14/421,950

(22) PCT Filed: Aug. 15, 2013

(86) PCT No.: PCT/US2013/055184
§ 371 (c)(1),
(2) Date: Feb. 16, 2015

(87) PCT Pub. No.: WO2014/028762
PCT Pub. Date: Feb. 20, 2014

(65) Prior Publication Data
US 2015/0218556 A1 Aug. 6, 2015

Related U.S. Application Data

(60) Provisional application No. 61/683,281, filed on Aug. 15, 2012.

(51) Int. Cl.
*A61K 48/00* (2006.01)
*C12N 15/11* (2006.01)
(Continued)

(52) U.S. Cl.
CPC ...... *C12N 15/113* (2013.01); *C12N 2310/113* (2013.01); *C12N 2310/14* (2013.01); *C12N 2310/141* (2013.01); *C12N 2320/12* (2013.01)

(58) Field of Classification Search
USPC .......................................................... 514/44
See application file for complete search history.

(56) References Cited

U.S. PATENT DOCUMENTS

| | | |
|---|---|---|
| 2011/0034538 A1 | 2/2011 | Croce et al. |
| 2012/0165382 A1 | 6/2012 | Olson et al. |
| 2012/0165392 A1* | 6/2012 | Olson ............... A61K 31/7105 514/44 A |

FOREIGN PATENT DOCUMENTS

| | | |
|---|---|---|
| WO | WO2008042231 | 4/2008 |
| WO | WO2009137807 | 11/2009 |

(Continued)

OTHER PUBLICATIONS

Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher AM, Dimmeler S. "MicroRNA-92a controls angiogenesis and functional recovery of ischemic tissues in mice." Science. 2009;324:1710-1713.

(Continued)

*Primary Examiner* — Terra C Gibbs
(74) *Attorney, Agent, or Firm* — Rodney L. Sparks

(57) ABSTRACT

The present application discloses roles for miR-93 in treating hypoxia and ischemia. Endothelial cells (HUVEC) and myocytes (C2C12) expressed miR-93 and up-regulated miR-93 in response to hypoxia and serum starvation. Over-expression of miR-93 in HUVECs promoted cell proliferation, prevented hypoxia-induced apoptosis, and enhanced endothelial cell tube formation. miR-93 knockdown in HUVECs resulted in increased hypoxia-induced apoptosis and decreased tube formation. Over-expression or knock-down of miR-93 in myocytes resulted in reduced or increased hypoxia-induced apoptosis, respectively. Down-regulation of miR-93 in C57BL/6 mice with antagomiR resulted in attenuated perfusion recovery (% non-ischemic leg at day-21: Scramble 85.22.9 vs. AntagomiR-93 67.96). Over-expression of miR-93 in BALB/C mice improved perfusion recovery (% non-ischemic leg at day 21: PremiR-93 757.5 vs. Scramble 59.62.5). The present invention (Continued)

encompasses the use of miR-93 and regulation of miR-93 to treat and prevent hypoxia, ischemia, and other injuries, diseases, disorders, and conditions associated with ischemia.

36 Claims, 14 Drawing Sheets

(51) Int. Cl.
*C07H 21/02* (2006.01)
*C07H 21/04* (2006.01)
*C12N 15/113* (2010.01)

(56) References Cited

FOREIGN PATENT DOCUMENTS

| WO | WO2011076147 | 6/2011 |
|---|---|---|
| WO | WO2011084460 | 7/2011 |

OTHER PUBLICATIONS

Yin KJ, Olsen K, Hamblin M, Zhang J, Schwendeman SP, Chen YE. "Vascular endothelial cell-specific microRNA-15a inhibits angiogenesis in hindlimb ischemia." J Biol Chem. 2012;287:27055-27064.

Fang L, Deng Z, Shatseva T, Yang J, Peng C, Du WW, Yee AJ, Ang LC, He C, Shan SW, Yang BB. "MicroRNA miR-93 promotes tumor growth and angiogenesis by targeting integrin-beta8." Oncogene. 2011;30:806-821.

Long J, Wang Y, Wang W, Chang BH, Danesh FR. "Identification of microRNA-93 as a novel regulator of vascular endothelial growth factor in hyperglycemic conditions." J Biol Chem. 2010;285:23457-23465.

Zhou, X, et al., Role of microRNAs in peripheral artery disease (Review), Molecular Medicine Reports 6: 695-700, 2012.

Hazarika, S., et al., "MicroRNA-93 Controls Perfusion Recovery After Hindlimb Ischemia by Modulating Expression of Multiple Genes in the Cell Cycle Pathway", Circulation, V. 127, No. 17, Apr. 30, 2013, 1818-1828.

Fu X, Tian J, Zhang L, Chen Y, Hao Q. "Involvement of microRNA-93, a new regulator of PTEN/Akt signaling pathway, in regulation of chemotherapeutic drug cisplatin chemosensitivity in ovarian cancer cells." FEBS Lett. 2012;586:1279-1286.

\* cited by examiner

Figure 1a - c.
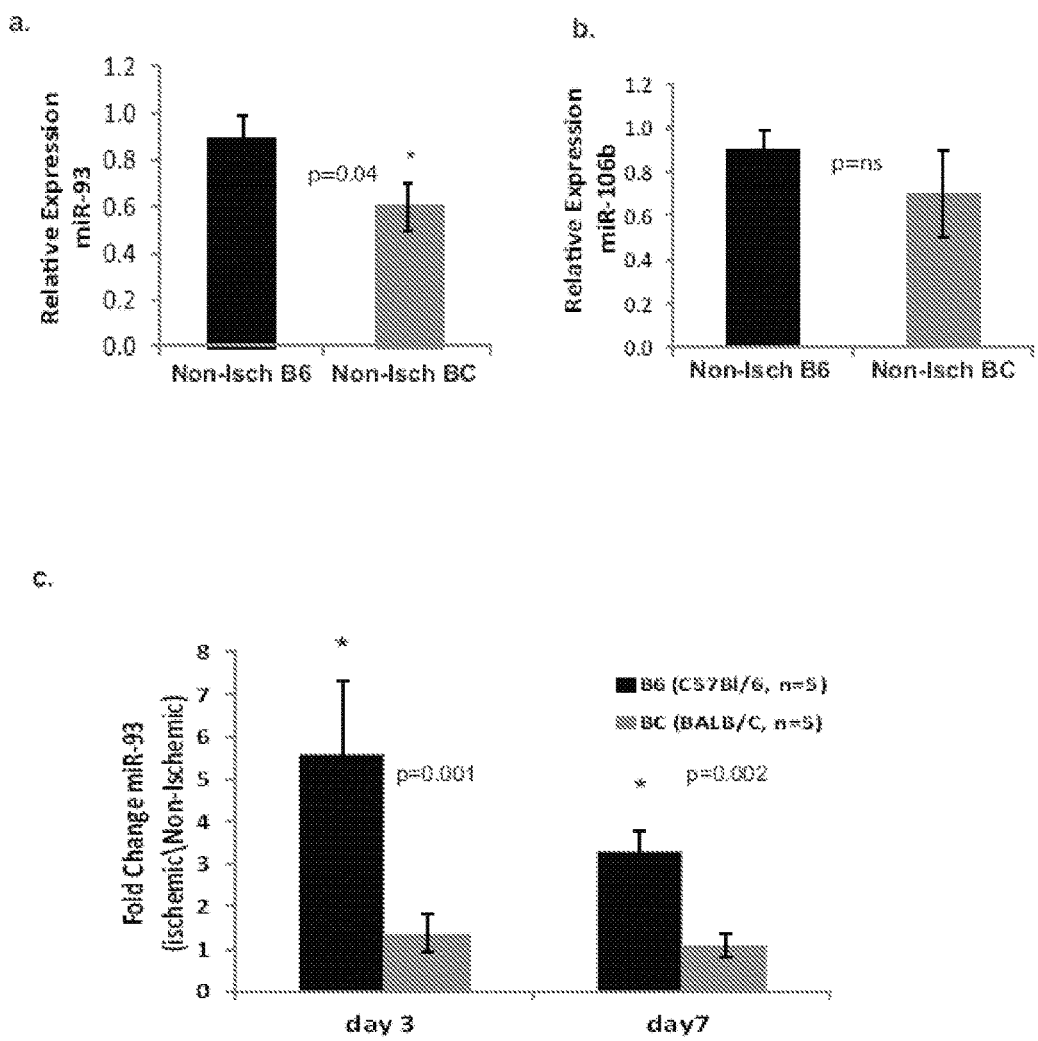

a. Gene Expression Changes at mRNA Level, Scramble vs. AntagomiR-93 treated C57Bl/6J b.
Gene Expression Changes at Protein level, Scramble vs. AntagomiR-93 treated C57BL/6J c. Gene changes at mRNA level with miR-93 Overexpression, BALB/cJ d. Changes at protein level with miR-93 Overexpression, BALB/cJ Range of colors (red to blue) indicates range of enrichment (high to low).

Supplemental Figure 1.
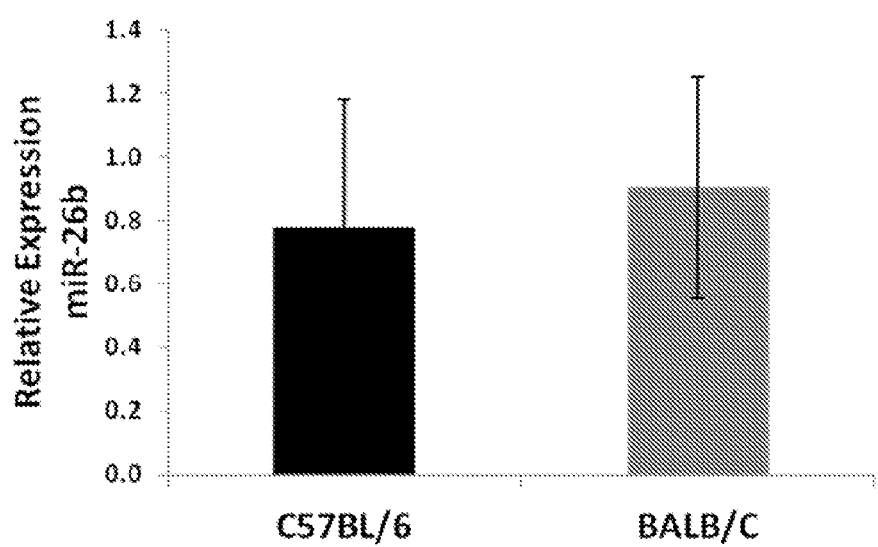

Supplemental Figure 2 a-d.
a.
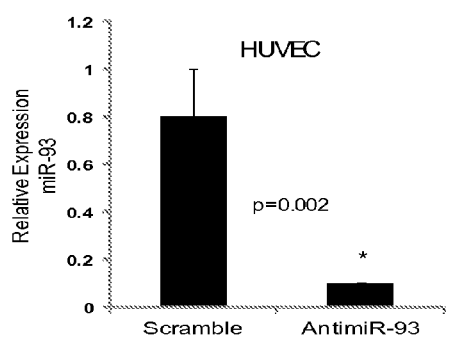
b.
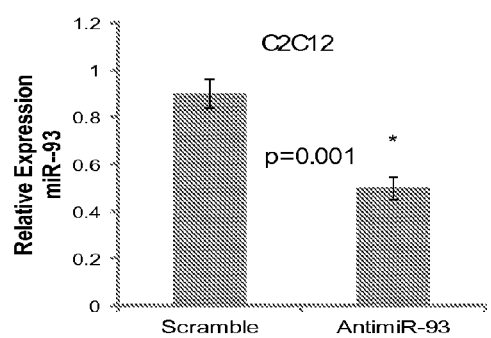
c.
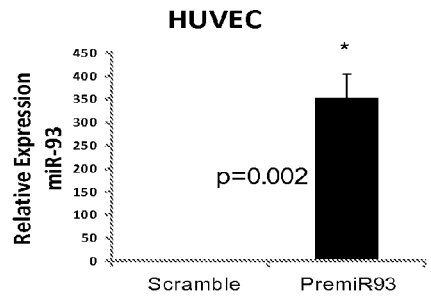
d.
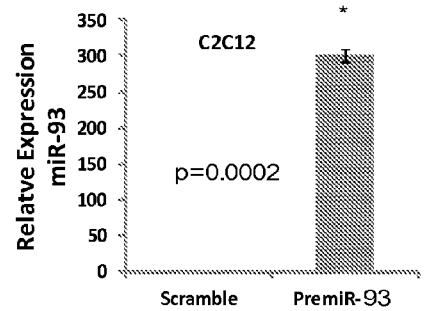

Supplemental Figure 3.
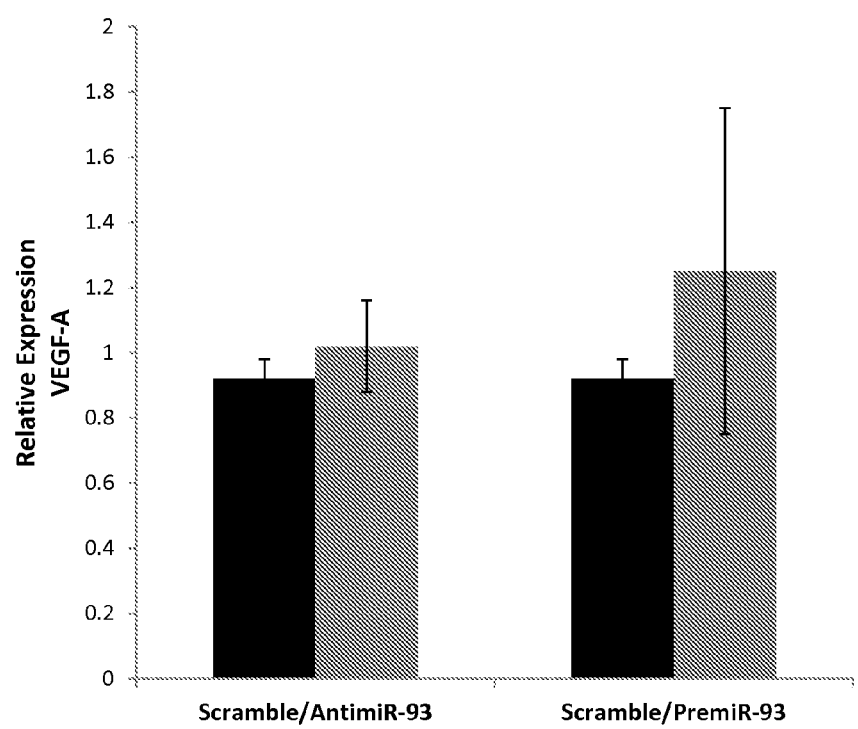

Supplemental Figure 4a and b.
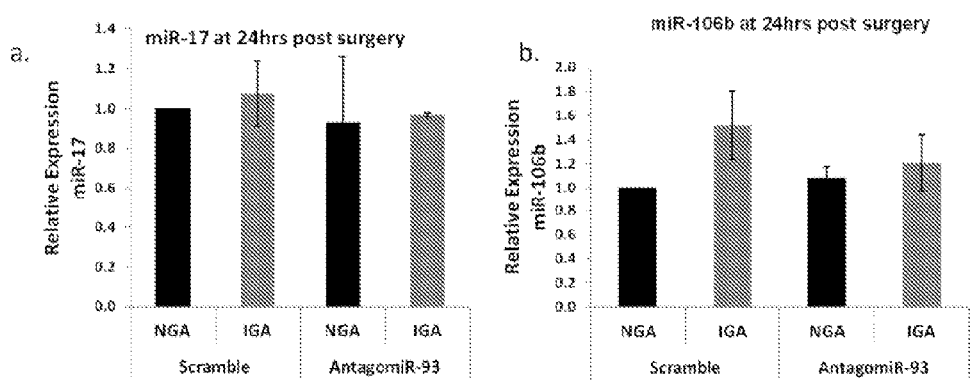

COMPOSITIONS AND METHODS FOR TREATING PERIPHERAL ARTERIAL DISEASE

CROSS REFERENCE TO RELATED APPLICATIONS

This application is a national stage filing of International Application No. PCT/US2013/055184, filed Aug. 15, 2013, which is entitled to priority pursuant to 35 U.S.C. §119(e) to U.S. provisional patent application no. 61/683,281, filed on Aug. 15, 2012. The entire disclosures of the afore-mentioned patent applications are incorporated herein by reference.

STATEMENT REGARDING FEDERALLY SPONSORED RESEARCH OR DEVELOPMENT

This invention was made with government support under HL101200 and HL007284 awarded by the National Institute of Health. The government has certain rights in the invention.

BACKGROUND

Peripheral arterial disease (PAD) affects approximately 8-12 million adults in the United States, and despite its significant impact on morbidity and mortality, a definitive medical therapy to improve perfusion in the ischemic hind limb is lacking. In response to tissue ischemia, a complex cascade of events leads to sprouting of new blood vessels from existing capillaries in the vicinity of ischemic tissue to form new blood vessels. This process of angiogenesis is an adaptive mechanism to promote blood supply to the ischemic tissue. Therapeutic angiogenesis, the stimulation of growth of new blood vessels distal to the site of occlusion, is an investigational therapeutic strategy to create a medical bypass to the ischemic limb and help improve perfusion in the ischemic tissue. A multitude of angiogenic growth factors have been exhaustively studied in both pre-clinical models of PAD and in clinical patients with PAD. Despite initial success in pre-clinical settings, most growth factors have uncertain final clinical outcomes. This necessitates a better understanding of regulation of gene expression following tissue ischemia.

In the past decade, micro-RNAs have emerged as strong endogenous regulators of gene expression, particularly important in disease/injury states. Micro-RNAs (miRs) are 16-25 nucleotide non-coding RNAs that are endogenous regulators of gene expression, particularly in disease/injury states. Micro-RNAs typically work by targeting mRNA degradation or by direct translational repression, and they can regulate a single gene or entire pathways (1, 2). Some micro-RNAs play crucial roles in developmental vasculogenesis (3) and in tumor angiogenesis (4-7). However, information on the role of micro-RNAs in ischemia-induced angiogenesis such as in myocardial ischemia and PAD is limited. Bonauer et al. showed that systemically delivered antagomirs against miR-92a enhanced perfusion recovery in a mouse model of PAD (8). Selection of miR-92a was based on the known role of the miR-17~92-cluster in angiogenesis, and its high level of expression in human umbilical vein endothelial cells (HUVEC) (8). Grundman et al. showed that inhibiting miR-100 enhanced perfusion recovery in the same hind-limb ischemia (HLI) model (9). Selection of miR-100 was based on its down-regulation in ischemic hind limb in a single strain of mice (C57B1/6J) (9). Finally, Yin et al. selected miR-15a based on its known role in regulation of Bcl-2 and its induction in oxygen-glucose deprived cerebral endothelial cells, and miR-15a knockdown improved angiogenesis in HLI (10).

There is a long felt need in the art for compositions and methods useful for enhancing endothelial cell and myocyte survival, for inducing angiogenesis, for treating ischemia, and for treating diseases, conditions, and disorders such as PAD. The present invention satisfies these needs.

SUMMARY OF THE INVENTION

The experiments and disclosure provided herein are based on an unbiased strategy and are based on different phenotypic outcomes that follow surgically induced HLI between inbred mouse strains. In an established pre-clinical model of PAD, it has been shown that C57B1/6J mice recover remarkably well while BALB/cJ mice show poor perfusion recovery following HLI (11, 12). This strain dependent response has been attributed to the extent of preformed collaterals, VEGF-A expression, and genes located in quantitative trait locus between the two strains (11-13).

The present application utilized C57BL/6J and BALB/cJ mice to examine micro-RNA expression in ischemic hind-limb muscles at a time-point when the two strains had similar recovery in order to identify micro-RNAs that are differentially regulated. Computational techniques were used to identify, and quantitative real-time-PCR to confirm, that micro-RNA-93 was the most consistent micro-RNA differentially regulated based on strain and ischemia. The role of miR-93 in vitro and in vivo was examined and it is disclosed herein that miR-93 is a potent modulator of cell proliferation, limits cell death, and modulates perfusion recovery following HLI by modulating expression of multiple genes in the cell cycle pathway.

It is further disclosed herein that up-regulation of miR-93 is beneficial for perfusion recovery from hind-limb ischemia. The present application discloses compositions and methods for regulating miR-93 expression and levels.

In one embodiment, the present invention provides for the use of miRNA to enhance or improve recovery from hypoxia and ischemia, including ischemia associated with vascular ischemia, peripheral arterial disease, myocardial ischemia, and brain ischemia. In one aspect, the vascular ischemia is coronary artery ischemia. In one aspect, the compositions and methods of the invention are useful for treating ischemia reperfusion injury.

One of ordinary skill in the art will appreciate that the amount of miRNA administered, timing of administration, etc., can be varied based on variables such as the injury, disease, disorder, or condition being treated and the age, gender, and health of the subject being treated. The methods of the invention are useful for enhancing, increasing, stimulating, augmenting, and even preventing multiple biological responses and providing improved clinical outcomes. In one aspect, the compositions and methods of the invention are useful for treating ischemia. In one aspect, the compositions and methods of the invention are useful for treating perfusion recovery.

In one aspect, the miRNA is miR-93.

In one embodiment, the present invention provides compositions and methods for treating or preventing a disease, disorder, injury, or condition associated with ischemia, comprising administering to a subject a pharmaceutical composition comprising an effective amount of an agonist of miRNA expression, levels, or activity, a pharmaceutically-acceptable carrier, and optionally an additional therapeutic agent. In one aspect, the miRNA is miR-93. In one aspect, the agonist of miR-93 is selected from the group of isolated nucleic acids consisting of a nucleic acid comprising a nucleic acid sequence encoding a precursor miR-93, a nucleic acid comprising a nucleic acid sequence encoding a mature miR-93, a nucleic acid comprising a precursor miR-93, and a nucleic acid comprising a mature miR-93, and biologically active fragments or homologs thereof. In one aspect, the isolated nucleic acid is a precursor miR-93 or biologically active fragments or homologs thereof. In another aspect, the isolated nucleic acid is a mature miR-93, or biologically active fragments or homologs thereof. In one aspect, the isolated nucleic acid is a deoxyribonucleic acid. In another aspect, the isolated nucleic acid is a ribonucleic acid.

In one embodiment, the sequences encoding miR-93 or mir-93 microRNA are selected from the group consisting of SEQ NOs:1, 2, 5, 6, 7, and 8, and biologically active fragments and homologs thereof. In one aspect, the agonist increases miR-93 expression, levels, or activity in a target cell or target tissue. In one aspect, the agonist is an miR-93 mimic.

In one embodiment, an isolated nucleic acid of the invention is encoded by a vector. In one aspect, the vector is an miRNA expression vector or AAV expression vector. In one aspect, the expression vector is an miRNA expression vector.

In one aspect, the isolated nucleic acid is operably-linked to a cell-specific promoter.

In one aspect, a lipid vehicle comprises said isolated nucleic acid.

In one aspect, additional therapeutic agents of the pharmaceutical compositions of the invention are anti-ischemia agents. One of ordinary skill in the art will appreciate that the composition may further comprise an effective amount of at least one additional therapeutic agents which may be useful for the type of injury, disease, or disorder being treated. Additional therapeutic agents include, but are not limited to, anesthetic, analgesic, antimicrobial, steroid, growth factor, cytokine, and anti-inflammatory agents. Useful anesthetic agents include benzocaine, lidocaine, bupivocaine, dibucaine, mepivocaine, etidocaine, tetracaine, butanilicaine, and trimecaine.

In another aspect, the agent is at least one analgesic. In yet another aspect, the agent is an additional therapeutic drug.

In a further aspect, the additional therapeutic agent is an antimicrobial agent. In one aspect, the antimicrobial agent is an antibacterial agent. In another aspect, the antimicrobial agent is an antifungal agent. In yet another aspect, the antimicrobial agent is an antiviral agent. Antimicrobial agents useful in the practice of the invention include, but are not limited to, silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine. It may be desirable for the antimicrobial to be other than Nystatin.

In another aspect, the agent is selected from aspirin, pentoxifylline, and clopidogrel bisulfate, or other angiogenic, or a rheologic active agent.

In one aspect, the invention provides for the use of miRNA or miRNA agonists to increase cell proliferation. In one aspect, treatment with miRNA treats hypoxia. In one aspect, the miRNA prevents apoptosis. In one aspect, treatment with miRNA prevents hypoxia-induced apoptosis. In one aspect, the miRNA is miR-93

In one aspect, miRNA or miRNA agonists of the invention are useful for preventing or treating symptoms associated with ischemia without effecting expression or levels of one or more of integrin β8, PTEN, VEGF-A, MCM-7, TGFβ1, Epiregulin, BMP-2, ATP8b, and Dusp-4. That is, addition of an miR-93 stimulator or of exogenous miR-93 does not up-regulate or down-regulate integrin β8, PTEN, VEGF-A, MCM-7, TGFβ1, Epiregulin, BMP-2, ATP8b, and Dusp-4. In one aspect, the expression is in cells of the target tissue, such as muscle.

One of ordinary skill in the art will appreciate that additional compounds could be used to regulate the proteins described above where no regulation by miR-93 was found and a certain result is desired, based on the fact that the regulation, or lack thereof, was measured at only certain time points. That is, the timing of treatment and of measurements disclosed herein may be critical to obtain the results described herein, and if so, these results are even more critical for designing treatment regimens for subjects. The same is true for other proteins disclosed herein that were found not to be regulated by miR-93. Additionally, although miR-93 or agonists of miR-93 can treat ischemia independently of regulating certain proteins, this does not preclude the use of additional agents which do regulate these proteins.

In one aspect, a compound or method of the invention unexpectedly enhances perfusion recovery independent of regulating integrin β8. In one aspect, miR-93 enhances perfusion recovery by down-regulation of multiple genes in the cell cycle pathway. In one aspect, increased levels, expression, or activity of miR-93 is associated with decreased levels of p21, E2F-1, and p53. In one aspect, increased levels, expression, or activity of miR-93 results in decreased levels of p21, E2F-1, and p53.

Other genes that can be targeted using the methods of the invention are summarized in the Examples and in Tables 1, 2, 3, Supplemental 1, and Supplemental 2.

In one aspect, the expression or levels of one or more of integrin β8, PTEN, VEGF-A, MCM-7, TGFβ1, Epiregulin, BMP-2, ATP8b, and Dusp-4 are not regulated by an miRNA or miRNA agonist.

In one embodiment, the compositions and methods of the invention are useful for causing decreased expression of at least one cell cycle pathway gene. In one aspect, the cell cycle pathway genes are selected from the group consisting of p21, E2F-1, and p53. In one aspect, the expression of at least one of p21, EF-1, and p53 decreases. In one aspect of the treatment, integrin β8, PTEN, VEGF-A, MCM-7, TGFβ1, Epiregulin, BMP-2, ATP8b, and Dusp-4 expression or levels do not change. In one aspect, the expression or levels of one or more of integrin β8, PTEN, VEGF-A, MCM-7, TGFβ1, Epiregulin, BMP-2, ATP8b, and Dusp-4 do not change. In one aspect, the expression is in muscle cells. In one aspect, the muscle cell is a skeletal muscle cell or a cardiac muscle cell. One of ordinary skill in the art will appreciate that administration can be directed to specific cells or tissues and that when expression vectors are used, cell or tissue-specific promoters can be used to help prevent or decrease expression in cells or tissues that are not the target cells or tissues.

In one embodiment of the invention, the administered agonist is incorporated into a muscle cell or an endothelial cell. In one aspect, the agonist incorporates into at least one muscle cell and an at least one endothelial cell.

In one embodiment of the invention, the treatment enhances perfusion recovery.

In one aspect, the treatment enhances angiogenesis. In one aspect, the treatment enhances the angiogenic response to ischemia.

In one embodiment, the method stimulates cell proliferation. In one aspect, the cell is an endothelial cell or a muscle cell. In one aspect, the muscle cell is a skeletal muscle cell or a cardiomyocyte.

In one embodiment, the disease, disorder, or condition being treated is peripheral arterial disease.

Based on the disclosure provided herein it can be appreciated that using the compounds and the methods of the invention the results described include a direct effect on a cell of interest. That is, a compound of the invention, such as a mature miR-93 (SEQ ID NOs:2, 6, 7, 8, and 10) or premiR-93 (SEQ ID NOs:1, 5, and 9), and biologically active fragments and homologs thereof, can be applied directly to a tissue of interest or cell of interest, including by transfection, and upon incorporation into the cell of interest effects expression and activity within the cell. The results demonstrate that using the methods of the invention the active compounds can work directly in a cell, instead of indirectly as published by others. That is, the effect disclosed herein is not due cell-cell interactions or to some kind of paracrine effect. In one aspect, the composition of the invention is directly injected into the tissue and the active compound is incorporated into the cell in which the effect is elicited.

The present invention discloses the unexpected result that increased expression, levels, or activity of miR-93 are involved in several aspects of ischemia and in improving perfusion recovery following ischemia.

In one embodiment, miRNA-93 enhances perfusion recovery by modulating expression of at least one gene in the cell cycle pathway. In one aspect, the perfusion recovery is after ischemia begins.

In one aspect, an increase in miR-93 attenuates hypoxia-induced apoptosis. In one aspect, it inhibits apoptosis of endothelial cells. In one aspect, it inhibits apoptosis of muscle cells. In one aspect, the muscle cell is a skeletal muscle cell. In one aspect, the muscle cell is a cardiac muscle cell.

In one embodiment, administering miR-93 or stimulating miR-93 expression, levels, or activity enhances capillary density and perfusion recovery from ischemia. In one aspect, the ischemia is in a limb.

The present invention provides compositions and methods for stimulating or enhancing angiogenesis by administering nucleic acids encoding miR-93 or by stimulating miR-93 expression, levels, or activity. Stimulation can be stimulation of endogenous miR-93 expression, levels, or activity.

In one aspect, an antagomir to miR-93 is useful for attenuating perfusion recovery after ischemia.

In one aspect, overexpression of miR-93 or increased activity of miR-93 enhances cell proliferation. In one aspect, the cell is an endothelial cell. In one aspect, the cell is a muscle cell. In one aspect, the muscle cell is a skeletal muscle cell. In one aspect, the muscle cell is a cardiac muscle cell.

The present invention provides a method of increasing expression of p21 or E2F-1, comprising contacting a cell with an effective amount of an inhibitor of miR-93. In one aspect, the inhibitor of miR-93 is an antagomir of miR-93.

In one aspect, inducing expression of MCM-7 is useful for treating ischemia and its related symptoms.

In one aspect, increased expression, levels, or activity of miR-93 enhances endothelial cell tube formation. In one aspect, knockdown or inhibition of miR-93 expression, levels, or activity reduces endothelial cell tube formation. In one aspect, the compositions and methods of the invention are useful for increasing endothelial cell tube formation. In one aspect, the compositions and methods of the invention are useful for increasing myocyte survival. In one aspect, the compositions and methods of the invention are useful for increasing myocyte proliferation.

In one aspect, the compositions and methods of the invention are useful for increasing angiogenesis.

In one aspect, compositions and methods of the invention are useful for administration of an miR to enhance angiogenesis. There are many ways to prepare and deliver a miR. In one aspect, the miR is a mature miR. In one aspect, the miR is a precursor miR. In one aspect, the miR is miR-93. An advantage for treating using miR is that no vector for gene transfer is required.

In one embodiment, the method of the invention increases capillary density at the site of disease, disorder, or condition associated with ischemia.

The present invention does not just encompass administering pharmaceutical compositions comprising an effective amount of miRNA or an isolated nucleic acid encoding miRNA. The present invention further encompasses targeting cells that express miR-93, such as endothelial cells and skeletal muscle cells, using compositions and methods that enhance miR-93 expression and levels to further increase the expression or levels of miR-93 in the cells. In one aspect, the increased expression or levels of miR-93 resulting from use of the compositions and methods of the invention enhances treatment and recovery. In one aspect, cells and tissues can be targeted by administration, such as injection, at the site of injury or interest, such as a muscle.

The present invention further provides compositions and methods useful for inhibiting or decreasing miR-93 expression and levels, including the use of antagomirs.

The present invention provides for isolated nucleic acids comprising sequences encoding an miRNA of the invention and for expression vectors comprising said isolated nucleic acids.

Useful expression vectors for practicing the methods of the invention include, but are not limited to, miRNA expression vectors. miRNA expression vectors are known in the art and include, for example, vectors from the following sources: Cell Biolabs (RAPAd® miRNA Adenoviral Expression System, Cat. # VPK-253; pMXs-miR-GFP/Puro Retroviral Expression Vector, Cat. # RTV-017; miRNASelect™ pEGP-miR Cloning & Expression Vector, Cat. # MIR-EXP-GP-C; miRNASelect™ pEP-miR Cloning & Expression Vector, Cat. # MIR-EXP-C); System Biosciences lentivector systems; Clontech; Origene's MicroRNA eXpression plasmid for over-expression of miRNAs of choice (##'s SC410001 and SC410002); Life Technologies/Ambion (multiple vectors, including for control miRNAs) and AAV vectors.

In one embodiment of the invention, the compositions can be administered by a route selected from the group consisting of oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, rectal, intrasternal injection, kidney dialytic infusion, and parenteral. In one aspect, the administration is intramuscular.

In one embodiment, an agonist of the invention is administered at a frequency selected from the group consisting of at least once a day, twice a day, three times a day, four times a day, once a week, twice a week, once a month, and twice a month. In one embodiment, at least two agonists are administered.

In one embodiment, the subject is a human

In one embodiment, the treatment is prophylactic.

The invention further provides kits for practicing the invention. In one aspect, a kit is provided for administering one or more compounds of the invention, the kit comprising at least one compound or polynucleotide of the invention, optionally supplied as a pharmaceutical composition comprising a pharmaceutically-acceptable carrier, an applicator, and an instructional material for the use thereof. Polynucleotides of the invention include the miRNAs of the invention and the isolated nucleotides comprising the sequences encoding the miRNAs of the invention (agonists, premiRs, mature miRNAs, DNA, RNA, etc.)

In another aspect, the present invention provides a kit for treating a disease, disorder, or condition associated with ischemia, the kit comprising at least one compound or polynucleotide of the invention, optionally supplied as a pharmaceutical composition comprising a pharmaceutically-acceptable carrier, an applicator, and an instructional material for the use thereof.

The data and invention upon which the present application is based, and which were the subject of U.S. Provisional Pat. App. No. 61/683,281, resulted in the publication Hazarika et al., 2013, Circulation, 127:1818-1828, the entirety of which is incorporated by reference herein.

Some Sequences of the Invention

```
full-length 80 residue precursor premiR-93 DNA
sequence (NCBI Accession No. NR_029510.1)
                                    SEQ ID NO: 1
CTGGGGGCTCCAAAGTGCTGTTCGTGCAGGTAGTGTGATTACCCAAC

CTACTGCTGAGCTAGCACTTCCCGAGCCCCGG a mature 22 residue miR-93 DNA sequence
(fragment of SEQ ID NO: 1; GenBank Accession
No. AF48053.1)
                                    SEQ ID NO: 2
AAAGTGCTGTTCGTGCAGGTAG Antagomir-93
                                    SEQ ID NO: 3
CUACCUGCACGAACAGCACUUUG Scramble (Bonauer et al.⁸)
                                    SEQ ID NO: 4
AAGGCAAGCUGACCCUGAAGUU miRNA equivalent 80 nucleotides of SEQ ID NO: 1
                                    SEQ ID NO: 5
CUGGGGGCUCCAAAGUGCUGUUCGUGCAGGUAGUGUGAUUACCCA

ACCUACUGCUGAGCUAGCACUUCCCGAGCCCCGG miRNA equivalent 22 nucleotide residues
of SEQ ID NO: 2
                                    SEQ ID NO: 6
AAAGUGCUGUUCGUGCAGGUAG "PremiR-93"- miRNA equivalent of 23 nucleotide
residues of a fragment of SEQ ID NO: 1 (an
extra 5' C compared to SEQ ID NO: 6; see also
accession numbers MIMAT0000093)
                                    SEQ ID NO: 7
CAAAGUGCUGUUCGUGCAGGUAG miRNA equivalent of 22 nucleotide residues of
a fragment of SEQ ID NO: 1 (see Accession Nos.
MIMAT0004509 and MIMAT0004636, and miRBase
Acc. No. MI0000095)
                                    SEQ ID NO: 8
ACUGCUGAGCUAGCACUUCCCG Transcribed SEQ ID NO: 1
                                    SEQ ID NO: 9
CUGGGGGCUCCAAAGUGCUGUUCGUGCAGGUAGUGUGAUUACCCA

ACCUACUGCUGAGCUAGCACUUCCCGAGCCCCGG

-continued
Transcribed SEQ ID NO: 2
                                    SEQ ID NO: 10
AAAGUGCUGUUCGUGCAGGUAG
```

One of ordinary skill in the art will appreciate that the present invention encompasses the use of biologically active homologs and analogs of these sequences.

Various aspects and embodiments of the invention are described in further detail below.

BRIEF DESCRIPTION OF THE DRAWINGS

FIG. 1. Micro-RNA-93 is differentially expressed between C57B1/6J and BALB/cJ mice. C57BL/6J (B6) mice have greater levels of miR-93 compared to BALB/cJ (BC). (a) Relative expression of miR-93 in non-ischemic gastrocnemius (GA) muscle from C57BL/6J mice is higher compared to that in BALB/cJ mice. (b) Relative expression of miR-106b in non-ischemic GA muscle from C57B1/6J and BALB/cJ mice was not significantly different. (c) Following induction of hind-limb ischemia, ischemic GA from C57BL/6J mice showed up-regulation of miR-93 at 5.6±1.4 fold at day 3 and 3.3±0.5 fold at day-7 compared to non-ischemic GA. BALB/cJ mice did not show this up-regulation of miR-93 (1.4±0.5 fold at day 3, 1.1±0.3 fold at day 7-post hind-limb ischemia). Data represent mean±SEM; n=5/group); Non-isch=Non-ischemic GA muscle.

Figures 2A, 2B:
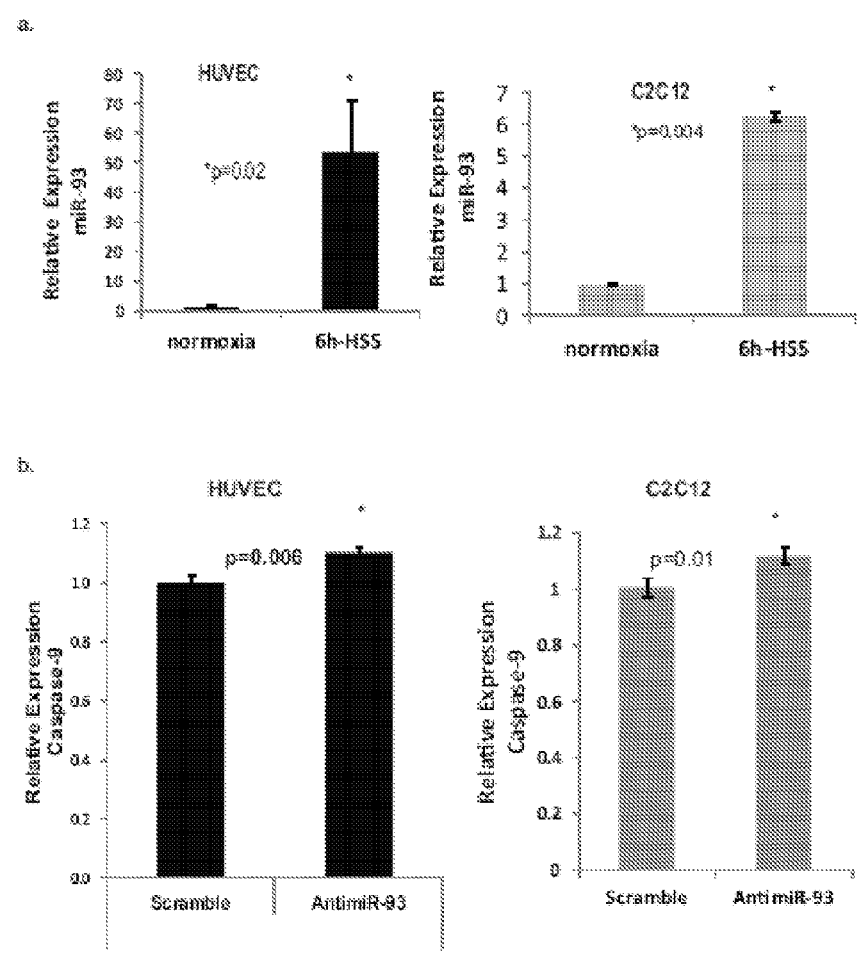
FIG. 2. Effects of miR-93 modulation in cellular apoptosis and proliferation (a) In both endothelial cells (HUVEC) and skeletal muscle cells (C2C12), miR-93 is up-regulated after exposure to 6-hours of hypoxia and serum starvation (6h-HSS). Data are representative of three separate experiments, n=3-5 wells/group. Bars represent mean±SEM. (b) In both HUVECs and C2C12 cells, knockdown of miR-93 resulted in up-regulation of the apoptotic gene caspase-9 even in the absence of any external injury. (c) In HUVECs, over-expression of miR-93 (PremiR-93) attenuates, and knock-down of miR-93 (AntimiR-93) increases hypoxia and serum starvation (HSS, 48-hours exposure)-induced apoptosis compared to scramble treated controls. (d) Similarly, in C2C12 cells, over-expression of miR-93 (PremiR-93) attenuates, while knockdown of miR-93 (AntimiR-93) increases HSS-induced (3-hours exposure) apoptosis. (e) Over-expression of miR-93 increased cell proliferation in both HUVEC and C2C12 cells 48-hours after transfection. Data are mean±SEM, n=6-8 wells/group, data representative of three separate experiments. (1) Forty-eight hours after transfection with Scramble miR-mimic or PremiR-93, HUVECs were plated in matrigel with reduced growth factor, and incubated for 6-hours in basal medium without or with 5% low serum growth supplement (LSGS). PremiR-93 treated HUVECs showed enhanced tube formation, which was quantitated as the number of full tubes per area (represented by bar graph). (g). Similarly, forty-eight hours after transfection with AntimiR-93 or Scramble siRNA sequences, HUVECs were plated in growth factor enriched matrigel and incubated for 6-hours in basal medium with or without a mixture of Endothelial Cell Growth Factors (GF). Tube formation was quantified as number of full tubes per area. As represented by the bar graph, tube formation was reduced in antimiR-93 treated HUVECs. Data are mean±SEM, n=4 wells/group, data representative of two separate experiments.
Figure 2C:
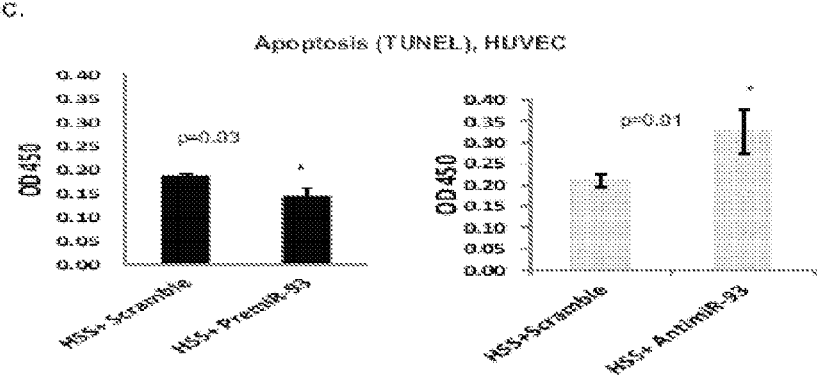

Supplemental FIG. 1. To validate results of micro-RNA microarray, we picked miR-26b as a negative control (a micro-RNA that was not differentially regulated by strain based on data from our array), and measured its expression using real time quantitative PCR. Consistent with data from array, relative expression of miR-26b was similar between C57Bl/6 and BALB/C mice (n=5/group, data represent mean±SEM; p=NS).

Supplemental FIG. 2. In-vitro knockdown and over-expression of miR-93 in HUVECs and C2C12 cells. HUVECs were transfected with 15 nM of AntimiR-93 or miRNA inhibitor negative control (scramble) for miR-93 knockdown, and premiR-93 or miR-mimic negative control (scramble) for miR-93 over-expression. C2C12 cells were transfected with the same sequences at doses of 120 nM. Micro-RNA-93 levels were measured 48 hours after transfection. AntimiR-93 knocked down expression of miR-93 by 80±2% in HUVECs (a) and by 60±1% in C2C12 cells (b) compared to scramble treated controls. PremiR-93 resulted in overexpression of miR-93 by >100-fold in both HUVECs (c) and C2C12 cells (d). Data represent mean±SEM. Data representative of three experiments.

Supplemental FIG. 3. Expression of VEGF-A was quantitated using real time RT-PCR in HUVECs with miR-93 knockdown or over-expression. Relative expression of VEGF-A was not different with miR-93 knockdown or over-expression compared to the respective scramble treated HUVECs. Data represent mean±SEM, p=ns; representative data from three different experiments using pooled HUVEC samples.

Supplemental FIG. 4. To investigate the specificity of systemic antagomiR-93, we checked the expression of two other micro-RNAs with sequence similarity and identical seeding sequence to miR-93, namely miR-17 (a) and miR-106b (b). Induction of miR-17 and miR-106b following hind-limb ischemia was similar between scramble and AntagomiR-93 treated mice at 24-hours after hind-limb ischemia, indicating that antagomiR-93 was specifically knocking down miR-93. IGA=ischemic GA, NGA=non-ischemic GA N=3/group. Data represent mean±SEM.

DETAILED DESCRIPTION

Abbreviations and Acronyms
bw—body weight
C2C12—an immortalized mouse muscle cell line
FDR—false discovery rate
GA—gastrocnemius muscle
GF—growth factor
GSEA—Gene Set Enrichment Analysis
HLI—hind-limb ischemia
HSS—hypoxia and serum starvation
HUVEC—human umbilical vein endothelial cell
IGA—ischemic gastrocnemius muscle
LNA—locked nucleic acid
LSGS—low serum growth supplement
miR—micro-RNA (also referred to as miRNA)
miRNA—micro-RNA (also referred to as miR)
NGA—non-ischemic gastrocnemius muscle
PAD—peripheral arterial disease
PremiR—a precursor miRNA
RISC—RNA-induced silencing complex
SEM—standard error of the mean
TA—tibialis anterior
VEGF—vascular endothelial growth factor Definitions In describing and claiming the invention, the following terminology will be used in accordance with the definitions set forth below.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal Fore example, an agonist of miR-93 expression, levels, or activity can include any compound which elicits the desired effect on endogenous miR-93, as well as transfection or addition of exogenous pre-miR-93 or a mature miR-93.

The term "alterations in peptide structure" as used herein refers to changes including, but not limited to, changes in sequence, and post-translational modification.

As used herein, "alleviating a disease or disorder symptom," means reducing the severity of the symptom or the frequency with which such a symptom is experienced by a patient, or both.

As used herein, amino acids are represented by the full name thereof, by the three-letter code corresponding thereto, or by the one-letter code corresponding thereto, as indicated in the following table:

| Full Name     | Three-Letter Code | One-Letter Code |
|---------------|-------------------|-----------------|
| Aspartic Acid | Asp               | D               |
| Glutamic Acid | Glu               | E               |
| Lysine        | Lys               | K               |
| Arginine      | Arg               | R               |
| Histidine     | His               | H               |
| Tyrosine      | Tyr               | Y               |
| Cysteine      | Cys               | C               |
| Asparagine    | Asn               | N               |
| Glutamine     | Gln               | Q               |
| Serine        | Ser               | S               |
| Threonine     | Thr               | T               |
| Glycine       | Gly               | G               |
| Alanine       | Ala               | A               |
| Valine        | Val               | V               |

-continued

| Full Name     | Three-Letter Code | One-Letter Code |
|---------------|-------------------|-----------------|
| Leucine       | Leu               | L               |
| Isoleucine    | Ile               | I               |
| Methionine    | Met               | M               |
| Proline       | Pro               | P               |
| Phenylalanine | Phe               | F               |
| Tryptophan    | Trp               | W               |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to, salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

Amino acids have the following general structure:

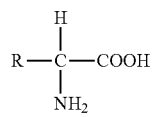

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

An "antagonist" is a composition of matter which when administered to a mammal such as a human, inhibits a biological activity attributable to the level or presence of a compound or molecule of interest in the mammal.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

As used herein, the term "attach", or "attachment", or "attached", or "attaching", used herein interchangeably with "bind", or "binding" or "binds" or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

As used herein, the term "avidity" refers to a total binding strength of a ligand with a receptor molecule, such that the strength of an interaction comprises multiple independent binding interactions between partners, which can be derived from multiple low affinity interactions or a small number of high affinity interactions.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

As used herein, the term "biopsy tissue" refers to a sample of tissue that is removed from a subject for the purpose of determining if the sample contains cancerous tissue. In some embodiment, biopsy tissue is obtained because a subject is suspected of having cancer. The biopsy tissue is then examined for the presence or absence of cancer.

As used herein, the term "carrier molecule" refers to any molecule that is chemically conjugated to a molecule of interest.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above. A "compound of the invention" refers to an miR or agonist of miR as described herein.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, "ductal cell", in reference to a pancreas, refers to any cell that forms or has the capability to form or originated from the ductal lining of ducts within and exiting from the pancreas.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length. Of course, these fragments must be considered in the context of the type of nucleic acid being used or the size of the nucleic acid that is the starting nucleic acid.

As used herein, a "functional" biological molecule is a biological molecule in a form in which it exhibits a property by which it is characterized.

A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting, or applying, or administering" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor or target molecule.

A "receptor" or target molecule is a compound that specifically binds to a ligand.

A ligand or a receptor "specifically binds to" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "mass tag", as used herein, means a chemical modification of a molecule, or more typically two such modifications of molecules such as peptides, that can be distinguished from another modification based on molecular mass, despite chemical identity.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

Micro-RNAs are generally about 16-25 nucleotides in length. In one aspect, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant adeno-associated viral (AAV) vector comprising a regulatory element active in muscle cells" refers to an AAV that has been constructed to comprise a new regulatory element to drive expression or tissue-specific expression in muscle of a gene of choice or interest. As described herein such a constructed vector may also contain at least one promoter and optionally at least one enhancer as part of the regulatory element, and the recombinant vector may further comprise additional nucleic acid sequences, including those for other genes, including therapeutic genes of interest.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal Such animals include mammals, preferably a human.

As used herein, a "subject in need thereof" is a patient, animal, mammal, or human, who will benefit from the method of this invention.

As used herein, the term "subject at risk for PAD" refers to a subject with one or more risk factors for developing PAD. Risk factors include, but are not limited to, gender, age, genetic predisposition, environmental expose, and previous incidents of PAD, and lifestyle.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence.

The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "transfection" is used interchangeably with the terms "gene transfer"", transformation," and "transduction", and means the intracellular introduction of a polynucleotide. "Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease, disorder, or condition for the purpose of decreasing the risk of developing pathology associated with the disease, disorder, or condition.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention encompasses the use of miR-93 and regulation of miR-93 to treat and prevent hypoxia, ischemia, and other injuries, diseases, disorders and conditions associated with ischemia such as peripheral arterial disease and myocardial ischemia. In one aspect, the compositions and methods of the invention are useful for treating ischemia reperfusion injury.

In one aspect, the ischemia is brain ischemia. In one aspect, the brain ischemia is associated with trauma.

In one aspect, the ischemia is vascular ischemia. In one aspect, the vascular ischemia is coronary artery ischemia.

In one embodiment, the present invention provides for the administration of at least one miRNA, including pre-miRNA and mature miRNA, or a mimic thereof. "miRNA mimics" are chemically synthesized nucleic acid based molecules, preferably double-stranded RNAs which mimic mature endogenous miRNAs after transfection into cells.

miRNAs are transcribed by RNA polymerase II (pol II) or RNA polymerase III and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

In one aspect, an agonist as used herein is a molecule or compound that enhances the expression, levels, or activity of a target miRNA.

An administered miRNA may be the naturally occurring miRNA or it may be an analogue or homologue of the miRNA. In one aspect, the miRNA, or analogue or homologues, are modified to increase the stability thereof in the cellular milieu. In an alternative aspect the miRNA is encoded by an expression vector and may be delivered to the target cell in a liposome or microvesicle.

In one embodiment, a stimulator of miR-93 expression, levels, or activity is an agonist. In one aspect, the agonist is a polynucleotide comprising a mature sequence of miR-93 or an active homolog or fragment thereof. In one aspect, the agonist is expressed from an expression construct.

In one embodiment, the agonist is administered to a subject by intravenous injection. In one aspect, the agonist is administered directly to the site of the disease, disorder or condition and the associated ischemia.

In one aspect, an miR-specific inhibitor may be an anti-miRNA (anti-miR) oligonucleotide (for example, see WO2005054494).

In one embodiment, the agonist is administered to a subject by oral, intravenous, intramuscular, transdermal, sustained release, controlled release, delayed release, suppository, subcutaneous, catheter, topical, or sublingual administration.

The present invention also encompasses a pharmaceutical composition comprising an agonist or antagonist of miR-93. In some embodiments, the pharmaceutical composition may be formulated for injection or topical administration. The formulation for topical administration may be a gel, cream, lotion, or ointment.

In another embodiment, an agonist of miR-93 is used in combination with other therapeutic modalities or agents for treating ischemia.

In one embodiment, agonists of miR-93 may be isolated nucleic acids comprising a precursor or mature miR-93 sequence. In some embodiments, the isolated nucleic acid comprises the sequence of SEQ NOs:1, 2, 5, 6, 7, 8, 9, and 10, and biologically active fragments and homologs thereof. In another embodiment, the agonist of miR-93 may be a polynucleotide comprising the pri-miRNA or pre-miRNA sequence for miR-93. The polynucleotide comprising the mature miR-93, pre-miR-93, or pri-miR-93 sequence may be single stranded or double stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-93 sequence is conjugated to cholesterol. In another embodiment, the agonist of miR-93 may be an agent distinct from miR-93 that acts to increase, supplement, or replace the function of miR-93.

In another embodiment, the agonist of miR-93 may be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-93 comprises a promoter "operably linked" to a polynucleotide encoding miR-93. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding miR-93 may encode the primary-microRNA sequence, the precursor-microRNA sequence, or the mature miR-93 sequence. In another embodiment, the expression vector comprises a polynucleotide operably linked to a promoter, wherein said polynucleotide comprises the sequence of SEQ NOs:1, 2, 5, 6, 7, 8, 9, 10 (or encodes the sequences) and biologically active fragments and homologs thereof where appropriate.

The term "expression construct" is meant to include any type of genetic construct containing a nucleic acid coding for a gene product in which part or all of the nucleic acid encoding sequence is capable of being transcribed. Generally, the nucleic acid encoding a gene product is under transcriptional control of a promoter. A "promoter" refers to a DNA sequence recognized by the synthetic machinery of the cell, or introduced synthetic machinery, required to initiate the specific transcription of a gene.

In one embodiment, a vector of the invention is a viral vector. In one aspect, the vector is an AAV (adeno-associated virus) vector. In one embodiment, a recombinant AAV vector of the invention is useful for targeting muscle preferentially over other tissues. In one embodiment, a recombinant AAV vector of the invention is useful for increasing expression of a gene of interest preferentially in muscle. The compositions and methods disclosed herein encompass targeting and transducing muscle with an AAV vector. The method comprises administering to a subject a pharmaceutical composition comprising an effective amount of a recombinant adeno-associated viral (AAV) vector comprising a regulatory element. The regulatory element comprises at least one promoter element and optionally at least one enhancer element. An enhancer and promoter are operably linked. The recombinant AAV vector also may optionally comprise at least one gene operably linked to a promoter element. The AAV may comprise the entire AAV genome, or a homolog or fragment thereof, such as the capsid of the particular AAV. However, it should be noted that the entire AAV genome may not be useful in some situations because of a need to make the vector replication-deficient and/or to insert genes of interest such as therapeutic genes.

The regulatory elements and the gene of interest may also be substituted with active fragments, modifications, or homologs thereof. In one aspect, the recombinant AAV vector preferentially targets skeletal muscle.

A recombinant AAV vector can be prepared for use in knocking down specific genes in muscle with siRNA or miRNA expressed from an AAV vector of the invention.

Other useful vectors, nucleic acids, and proteins or homologs and fragments thereof are useful with the practice of the invention, including but not limited to AAV-9-NCBI Accession number AX753250 and AAV-8-NCBI Accession number NC_006261.

Due to the payload constraints of AAV, in one embodiment a cDNA may be preferred. In one aspect, additional introns and sequences can be introduced. In one aspect, the cap gene of the AAV is used and not the entire AAV genomic DNA.

Other methods and vectors are known in the art which could also be used to practice the methods of the present invention, including those in Souza et al. (U.S. Pat. Pub. No. 2011/0212529, published Sep. 1, 2011).

Although AAVs such as AAV9 and AAV8 may target some tissues with higher specificity than other tissues, the use of tissue or cell specific enhancers and promoters as part of the vector can help to ensure that the genes of interest are expressed in the desired cell or tissue.

A more detailed description and use of AAVs can be found in U.S. Pat. Pub. No. US 2013/0136729 (French and Annex, U.S. patent application Ser. No. 13/673,351), the entirety of which is incorporated by reference herein.

Ordahl et al. (U.S. Pat. No. 5,266,488) characterized the chicken troponin-T gene promoter and found the essential proximal promoter element contains nonspecific sequences necessary for the initiation of transcription of a structural gene to be operatively associated with the promoter. See FIG. 2 of Ordahl and SEQ ID NO:18 herein. When +1 designates the first nucleotide of the transcription initiation site, this element is located between nucleotide −49 and nucleotide +1. Further, Ordahl demonstrated that the skeletal muscle-specific regulatory element is positioned upstream of the essential proximal promoter element and is operationally associated therewith. This element is necessary for the expression of a structural gene to be operatively associated with the promoter in skeletal muscle cells. The skeletal muscle-specific regulatory element is located between nucleotide −129 and −49. Ordahl also stated that the cardiac muscle-specific regulatory element is positioned upstream of both the skeletal muscle specific regulatory element and the essential proximal promoter element and is operatively associated with the essential proximal promoter element and suggested that this element is necessary for the expression of a structural gene to be operatively associated with the promoter in cardiac muscle cells. Ordahl also asserted that the cardiac muscle-specific regulatory element is located between nucleotide −268 and nucleotide −201.

Ordahl also demonstrated that the nonessential positive striated muscle regulatory element is positioned upstream of, and operationally associated with, both the skeletal muscle specific regulatory element and the cardiac muscle-specific regulatory element. This element facilitates the expression of a structural gene to be operatively associated with the promoter in striated muscle cells, both cardiac and skeletal. This element is located between nucleotide −550 and −269.

According to Ordahl, the nonessential negative regulatory element is positioned upstream of the positive striated muscle regulatory element and is operatively associated therewith. This element inhibits the positive striated muscle regulatory element from facilitating the expression of a structural gene to be operatively associated with the promoter. This element is located between nucleotide −3000 and nucleotide −1100. More broadly defined, this element is located between nucleotide −3000 and nucleotide −550.

In one embodiment, the present invention encompasses the use of the promoter regions described by Ordahl for targeting muscle in general or for more specifically targeting cardiac muscle over skeletal muscle or vice-versa.

A complete promoter (one containing all the elements described above) expresses a structural gene operatively associated therewith in both skeletal and striated muscle cells. The individual elements which comprise a complete promoter can be used in any desired operable combination to produce new promoters having different properties. For example, the negative nonspecific regulatory element can be deleted from a complete promoter so that the expression of a gene associated with the promoter is facilitated. The cardiac muscle-specific regulatory element can be deleted from a complete promoter so that a structural gene operatively associated with the promoter is preferentially expressed in skeletal cells, or the skeletal muscle-specific regulatory element can be deleted from a complete promoter so that a structural gene operatively associated with the promoter is preferentially expressed in cardiac cells. The term "deleted," as used herein, means any modification to a promoter element which renders that element inoperable.

Operable promoters can be constructed from the minimum necessary regulatory elements. One such promoter comprises an essential proximal promoter element and a cardiac muscle-specific regulatory element positioned upstream of the essential proximal promoter element and operatively associated therewith. Another such promoter comprises an essential proximal promoter element and a skeletal muscle-specific regulatory element positioned upstream of said essential proximal promoter element and operatively associated therewith. To these promoters, a positive striated muscle regulatory element may optionally be positioned upstream oft and operatively associated with, the specific regulatory element (skeletal or cardiac).

Therefore, the present invention encompasses the use of a cardiac troponin-T promoter, for example, where the sequence comprises a promoter and is the 5' region of about nucleotide position −3000 to about the transcription start site of cardiac troponin-T or about nucleotide +25 to about +50, or where the sequence comprises the 5' region of about nucleotide −1000 to about the transcription start site or about nucleotide +25 to about +50, or where the sequence comprises the 5' region of about nucleotide −550 to about the transcription start site or about nucleotide +25 to about +50, or where the sequence comprises the 5' region of about nucleotide −400 to about the transcription start site or about nucleotide +25 to about +50, or where the sequence comprises the 5' region of about nucleotide −300 to about the transcription start site or about nucleotide +25 to about +50. In one aspect, the sequence is about 375 nucleotides upstream (−) to 43 nucleotides downstream (+) (see Example 1). In another aspect, the sequence is 5' region from about nucleotide −268 to about nucleotide +38 relative to the transcription start site.

It will be understood by one of ordinary skill in the art that when a different promoter is being used, such as a muscle creatine kinase promoter, similar to the cardiac troponin-T promoter various lengths of the sequence can also be used.

In one embodiment, the present invention encompasses compositions and methods for transducing skeletal muscle and enhancing gene expression using an AAV vector engineered to comprise a skeletal muscle gene promoter. In one aspect, the AAV is AAV9 or AAV8.

In one embodiment, the present invention relates to gene therapy methods utilizing tissue-specific expression vectors. The invention further relates to expression vectors used for delivery of a transgene into muscle. In one aspect, the muscle is cardiac muscle. In another aspect, the muscle is skeletal muscle. More specifically, the invention relates to transcriptional regulatory elements that provide for enhanced and sustained expression of a transgene in the muscle.

Skeletal muscle promoters and enhancers are available for the muscle creatine kinase (MCK) gene and are encompassed by the presented invention for regulating expression of a therapeutic gene in an AAV vector of the invention.

Accordingly, one embodiment of the invention provides expression vectors optimized for sustained expression of a transgene in muscle tissue. Another object of this invention is to provide enhancer/promoter combinations that can direct sustained and appropriate expression levels in various expression systems.

In one embodiment, the invention encompasses combining minimal sequences from muscle-specific promoters and muscle-specific enhancers to create chimeric regulatory elements that drive transcription of a transgene in a sustained fashion. A minimal sequence is one which maintains the function of interest, although possibly somewhat less than the full sequence of interest. The resulting chimeric regulatory elements are useful for gene therapy directed at transgene expression in the muscle as well as other applications requiring long-term expression of exogenous proteins in transfected muscle cells such as myocytes. In one aspect, the myocytes are cardiac myocytes. In another aspect, the myocytes are skeletal muscle myocytes.

Chimeric regulatory elements useful for targeting transgene expression to the muscle are provided by the invention. The chimeric regulatory elements of the invention comprise combinations of muscle-specific promoters and muscle-specific enhancers that are able to direct sustained transgene expression preferentially in the muscle. In one aspect, the enhancers and promoters are cardiac specific and in another aspect, the enhancers and promoters are skeletal muscle specific.

The present invention is also directed to recombinant transgenes which comprise one or more operably linked tissue-specific regulatory elements of the invention. The tissue-specific regulatory elements, including muscle-specific promoter and enhancers operably linked to a transgene, drive its expression in myocytes and, in particular, in cardiomyocytes and/or skeletal myocytes. The transgenes may be inserted in recombinant viral vectors for targeting expression of the associated coding DNA sequences in muscle. Muscle-specific promoters useful in the invention include, for example, muscle creatine kinase (MCK) promoter, cardiac troponin-T promoter, or desmin (DES) promoter. In one particular embodiment, the promoter is a human promoter. In another embodiment, the promoter is a murine promoter. In yet another embodiment, the promoter is a chicken promoter. In certain embodiments, the promoter is truncated.

In one embodiment, tissue-specific enhancers are used. Tissue-specific enhancers include muscle specific enhancers. One or more of these muscle-specific enhancer elements may be used in combination with a muscle-specific promoter of the invention to provide a tissue-specific regulatory element. In one embodiment, the enhancers are derived from human, chicken, or mouse. In certain embodiments, the enhancer/enhancer or enhancer/promoter combinations are heterologous, i.e., derived from more than one species. In other embodiments, the enhancers and promoters are derived from the same species. In certain embodiments, enhancer elements are truncated.

In one embodiment, a regulatory element of the invention comprises at least one MCK or cardiac troponin-T enhancer operably linked to a promoter. In another embodiment, a regulatory element of the invention comprises at least two MCK enhancers linked to a MCK promoter or a DES promoter or a cardiac troponin-T promoter. In yet another embodiment, a regulatory element comprises at least two DES enhancers linked to a promoter. In a further embodiment, a regulatory element comprises at least two cardiac troponin-T enhancers linked to a promoter.

The invention provides vectors comprising a regulatory element of the invention. In some embodiments, a regulatory element of the invention is incorporated into a viral vector such as one derived from adenoviruses, adeno-associated viruses (AAV), or retroviruses, including lentiviruses such as the human immunodeficiency (HIV) virus. In one embodiment, the AAV is AAV8 or AAV9. The invention also encompasses methods of transfecting muscle tissue where such methods utilize the vectors of the invention.

The invention further provides cells transfected with the nucleic acid containing an enhancer/promoter combination of the invention.

Promoters may be coupled with other regulatory sequences/elements which, when bound to appropriate intracellular regulatory factors, enhance ("enhancers") or repress ("repressors") promoter-dependent transcription. A promoter, enhancer, or repressor, is said to be "operably linked" to a transgene when such element(s) control(s) or affect(s) transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, and other expression control elements, or any combination of such elements.

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis as the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000-fold from linked homologous or heterologous promoters. Enhancer elements often remain active even if their orientation is reversed (Li et al., J. Bio. Chem. 1990, 266: 6562-6570). Furthermore, unlike promoter elements, enhancers can be active when placed downstream from the transcription initiation site, e.g., within an intron, or even at a considerable distance from the promoter (Yutzey et al., Mol. and Cell. Bio. 1989, 9:1397-1405).

It is known in the art that some variation in this distance can be accommodated without loss of promoter function. Similarly, the positioning of regulatory elements with respect to the transgene may vary significantly without loss of function. Multiple copies of regulatory elements can act in concert.

Typically, an expression vector comprises one or more enhancer sequences followed by, in the 5' to 3' direction, a promoter sequence, all operably linked to a transgene followed by a polyadenylation sequence.

The present invention further relies on the fact that many enhancers of cellular genes work exclusively in a particular tissue or cell type. In addition, some enhancers become active only under specific conditions that are generated by the presence of an inducer such as a hormone or metal ion. Because of these differences in the specificities of cellular enhancers, the choice of promoter and enhancer elements to be incorporated into a eukaryotic expression vector is determined by the cell type(s) in which the recombinant gene is to be expressed.

In one aspect, the regulatory elements of the invention may be heterologous with regard to each other or to a transgene, that is, they may be from different species. Furthermore, they may be from species other than the host, or they also may be derived from the same species but from different genes, or they may be derived from a single gene.

The present invention further includes the use of desmin regulatory elements. Desmin is a muscle-specific cytoskeletal protein that belongs to the family of intermediate filaments that occur at the periphery of the Z disk and may act to keep adjacent myofibrils in lateral alignment. The expression of various intermediate filaments is regulated developmentally and shows tissue specificity.

The muscle creatine kinase (MCK) gene is highly active in all striated muscles. Creatine kinase plays an important role in the regeneration of ATP within contractile and ion transport systems. It allows for muscle contraction when neither glycolysis nor respiration is present by transferring a phosphate group from phosphocreatine to ADP to form ATP. There are four known isoforms of creatine kinase: brain creatine kinase (CKB), muscle creatine kinase (MCK), and two mitochondrial forms (CKMi). MCK is the most abundant non-mitochondrial mRNA that is expressed in all skeletal muscle fiber types and is also highly active in cardiac muscle. The MCK gene is not expressed in myoblasts, but becomes transcriptionally activate when myoblasts commit to terminal differentiation into myocytes. MCK gene regulatory regions display striated muscle-specific activity and have been extensively characterized in vivo and in vitro. Mammalian MCK regulatory elements are described, for example, in Hauser et al., Mol. Therapy 2000, 2:16-25 and in Souza et al., 2011. MCK enhancer and promoter sequences are provided herein.

The present invention further includes the use of troponin regulatory elements, particularly cardiac troponin.

The present invention further includes the use of combinations of elements to form, for example, chimeric regulatory elements. The present invention is directed to recombinant transgenes which comprise one or more of the tissue-specific regulatory elements described herein. The chimeric tissue-specific regulatory elements of the invention drive transgene expression in muscle cells. In one aspect the muscle cell is a skeletal muscle cell. In one aspect, the muscle cell is a cardiomyocyte. The transgenes may be inserted in recombinant viral or non-viral vectors for targeting expression of the associated coding DNA sequences in muscle. In one aspect, the viral vector is an AAV. In one embodiment, the promoter element is selected from the group consisting of muscle creatine kinase (MCK) promoter, desmin promoter, and cardiac troponin T promoter. In one particular embodiment, the promoter is a human promoter. In another embodiment, the promoter is a murine promoter. In another embodiment, the promoter is a chicken promoter. In certain embodiments, the promoter is truncated. One of ordinary skill in the art will appreciate that the entire promoter need not necessarily be used in all cases and that activity can be maintained when some nucleotides are deleted or added.

In one embodiment, a regulatory element of the invention comprises at least one MCK enhancer operably linked with a DES promoter or an MCK promoter or a cardiac troponin-T promoter. In another embodiment, the regulatory element comprises at least two MCK enhancers linked to a MCK promoter or a DES promoter or a cardiac troponin-T promoter. In yet another embodiment, a regulatory element comprises at least two DES enhancers linked to a DES promoter. In yet another embodiment, a regulatory element comprises at least two cardiac troponin-T enhancers linked to a cardiac troponin-T promoter. In one aspect, the MCK enhancer comprises the sequence of SEQ ID NO:15 or an active fragment or modification thereof.

It will be understood that the regulatory elements of the invention are not limited to specific sequences referred to in the specification but also encompass their structural and functional analogs/homologues and functional fragments thereof. Such analogs may contain truncations, deletions, insertions, as well as substitutions of one or more nucleotides introduced either by directed or by random mutagenesis. Truncations may be introduced to delete one or more binding sites for known transcriptional repressors. Additionally, such sequences may be derived from sequences naturally found in nature that exhibit a high degree of identity to the sequences in the invention. In one aspect, a nucleic acid of 20 nt or more will be considered to have high degree of identity to a promoter/enhancer sequence of the invention if it hybridizes to such promoter/enhancer sequence under stringent conditions. Alternatively, a nucleic acid will be considered to have a high degree of identity to a promoter/enhancer sequence of the invention if it comprises a contiguous sequence of at least 20 nt, which has percent identity of at least 60%, 65%, 70%, 75%, 80%, 85%, 90%, 95%, or more as determined by standard alignment algorithms such as, for example, Basic Local Alignment Tool (BLAST) described in Altschul et al., J. Mol. Biol. 1990, 215: 403-410, the algorithm of Needleman et al., J. Mol. Biol. 1970, 48: 444-453, or the algorithm of Meyers et al., Comput. Appl. Biosci. 1988, 4: 11-17. Non-limiting examples of analogs, e.g., homologous promoter sequences and homologous enhancer sequences derived from various species, are described in the present application.

In one embodiment, the invention further includes vectors comprising a regulatory element of the invention. In general, there are no known limitations on the use of the regulatory elements of the invention in any vector. A regulatory element comprises a promoter element and optionally an enhancer element.

In one embodiment an antagonist of mir-93 may be used. In one aspect, the antagonist is an antisense oligonucleotide or an antagomir. In one aspect, the antisense oligonucleotide comprises a sequence that is at least partially complementary to a mature sequence of miR-93.

miRNA expression vectors are known in the art, for example, from: Cell Biolabs (RAPAd® miRNA Adenoviral Expression System, Cat. # VPK-253; pMXs-miR-GFP/Puro Retroviral Expression Vector Cat. # RTV-017; miRNASelect™ pEGP-miR Cloning & Expression Vector, Cat. # MIR-EXP-GP-C; miRNASelect™ pEP-miR Cloning & Expression Vector, Cat. # MIR-EXP-C); SBI's (System Biosciences) lentivector systems; Clontech; Origene's MicroRNA eXpression plasmid for over-expression of miRNAs of choice (##'s SC410001 and SC410002); Life Technologies/Ambion (multiple vectors, including for control miRNAs).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double--stranded DNA, supercoiled DNA and/or triple-helical DNA; Z-DNA; miRNA, siRNA, and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

miRNAs are RNA molecules of about 22 nucleotides or less in length, but are variable in length. These molecules are post-transcriptional regulators that bind to complementary sequences on target mRNAs. Although miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. In one embodiment, an anti-miRNA oligomer directed against miR-93 can be used. See U.S. patent application Ser. No. 13/503,189, WO2007/112754, and WO2007/112653 for additional descriptions of oligomers, locked nucleic acid oligomers, gapmers, mixmers, totalmers, etc. In one aspect, an anti-miR-93 can be purchased.

The invention is also directed to methods of administering the compounds, cells, proteins and peptides (collectively referred to as compounds) of the invention to a subject.

In one aspect the nucleic acid is an antisense molecule, an oligonucleotide, an RNA, an siRNA, and an miRNA.

Although miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules.

Pharmaceutical compositions comprising the present compounds are administered to an individual in need thereof by any number of routes which effectively transport the active compound to the appropriate or desired site of action including, but not limited to, topical, oral, intravenous, intramuscular, intra-arterial, intramedullary, intrathecal, intraventricular, parenteral, transdermal, subcutaneous, intraperitoneal, intranasal, enteral, topical, sublingual, pulmonary, buccal, vaginal, or rectal means.

The present invention is also directed to pharmaceutical compositions comprising the polynucleotides/nucleic acids of the present invention. More particularly, such compounds can be formulated as pharmaceutical compositions using standard pharmaceutically acceptable carriers, fillers, solublizing agents and stabilizers known to those skilled in the art.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

In one embodiment, the pharmaceutical compositions useful for practicing the invention may be administered to deliver a dose of nucleic acid or additional therapeutic agent of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a subject for treatment of the diseases disclosed herein.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

A composition of the invention may comprise additional ingredients. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

The pharmaceutical composition may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies.

Additional Therapeutic Agents and Ingredients

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof.

In one embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart). Antimicrobial agents useful for the invention include those directed against the spectrums of gram positive organisms, gram negative organisms, fungi, and viruses.

According to the topical anesthetic embodiment of the present invention, in one aspect, suitable local anesthetic agents having a melting point of 30° to 70° C. are prilocaine, tetracaine, butanilcaine, trimecaine, benzocaine, lidocaine, bupivocaine, dibucaine, mepivocaine, and etidocaine.

The present invention further encompasses the use of at least two anesthetics.

The local anesthetic composition of the present invention may further comprise suitable additives, such a pigment, a dye, an anti-oxidant, a stabilizer or a fragrance provided that addition of such an additive does not destroy the single phase of the anesthetic composition.

In one aspect, the hydrated local anesthetic mixture is prepared by melting the local anesthetic with the higher melting point of the two, followed by addition of the other local anesthetic, under vigorous mechanical mixing, such as trituration or grinding A milky viscous liquid is formed, at which point, the surfactant is added with more mechanical mixing. Mixing of the surfactant produces a milky liquid of somewhat lower viscosity. Finally, the balance of water is added under vigorous mechanical mixing. The material can then be transferred to an air tight container, after which a clear composition is obtained after about 60 minutes at room temperature.

Alternatively, the hydrated local anesthetic mixture can be prepared by first melting the lower melting local anesthetic, followed by addition of the other local anesthetic along with vigorous mechanical mixing, then addition of the surfactant and water as above. However, when the lower melting local anesthetic is melted first, the storage time needed to obtain the single phase composition, increases from about 1 hour to about 72 hours. Accordingly, the former method is preferred.

One of ordinary skill in the art will appreciate that there are multiple suitable surfactants useful for preparing the hydrated topical anesthetic of the present invention. For example, single-phase hydrated topical anesthetics can be prepared from anionic, cationic or non-ionic surfactants.

Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

A list of the types of drugs, and specific drugs within categories which are encompassed within the invention is provided below and are intended be non-limiting examples.

Antimicrobial agents include: silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive: Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Growth Factors

In one embodiment, an effective amount of at least one growth factor, cytokine, hormone, or extracellular matrix compound or protein useful for enhancing wound healing is administered. In one aspect, a combination of these agents is used. In one aspect, growth factors useful in the practice of the invention include, but are not limited to, EGF, PDGF, GCSF, IL6, IL8, IL10, MCP1, MCP2, Tissue Factor, FGFb, KGF, VEGF, PLGF, MMP1, MMP9, TIMP1, TIMP2, TGFβ, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans can be easily determined by a person skilled in the art.

The invention is now described with reference to the following Examples. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Methods

Murine Model of Hind-limb Ischemia and Monitoring of Perfusion Recovery: Animal studies were approved by the Institutional Animal Care Committee and conformed to the Guide for the Care and Use of Laboratory Animals published by the US National Institute of Health. After inducing anesthesia (ketamine 90 mg/kg and xylazine 10 mg/kg), unilateral femoral artery ligation and excision was done on 8-12 weeks old male C57B1/6J or BALB/cJ mice (number as indicated for each experiment result) as described previously[14, 15]. Perfusion recovery was measured using laser Doppler imaging (Perimed, Inc) on days 0, 3, 7, 14, and 21 post-surgery. Perfusion in the ischemic limb was normalized to that in the non-ischemic limb for each mouse. Micro-RNA Micro-array: Gastrocnemius muscles were collected from C57B1/6J and BALB/cJ mice (n=3/group) at day 3 post-surgery. RNA was isolated using trizol total transcriptome isolation protocol and Pure Link RNA Mini kits following manufacturer's instructions (Life Technologies, Carlsbad, Calif.). RNA was aliquoted into 50 µg amounts, and arrays were done using Illumina micro-RNA chips containing 380 mouse micro-RNAs (V2 Micro-RNA Expression Profiling Kit; miRbase 9.1). Differentially expressed micro-RNAs were sorted based on regulation by a combination of ischemia and strain, or regulation by ischemia or strain alone.

mRNA Micro-array: For mouse mRNA arrays between ischemic and non-ischemic tissue, gastrocnemius muscle from BALB/cJ mice (n=3/group) were harvested at day 3-post-HLI. Total RNA was extracted using trizol total transcriptome isolation protocol. After quality control, RNAs were aliquoted into 50 µg aliquots and arrays were done using Gene Chip mouse genome 43-2.0. For HUVEC mRNA arrays, RNA from HUVECs were isolated after HUVECs were transfected with scramble or antimiR-93 and incubated for 24-hours under conditions of hypoxia and serum starvation (total of 48 hrs post-transfection). Arrays were done using Illumina Human 6 V 1 platform. Non-normalized data were obtained using Illumina's Genome Studio. Quality control, pre-processing and quantile normalization was done using R[16] and the beadarray package[17]. Analysis for gene set enrichment was done using GSEA[18] V 2.0 from Broad Institute, using 100 permutations and FDR cutoff of <0.25.

In vivo Knockdown of miR-93: Antagomir-93 and scramble sequences were synthesized following the nucleotide modifications as described by Krutzfeldt et al.[19]. Oligo sequences were as follows: Antagomir-93: 5'-CUACCUG-CACGAACAGCACUUUG-3' (SEQ ID NO:3). Scramble (Bonauer et al[8]) 5'-AAGGCAAGCUGACCCUGAAGUU-3' (SEQ ID NO:4). Oligos were dissolved in PBS and injected retro-orbitally at a dose of 8 mg/kg body weight[8,9]. Injections were given 30-minutes prior to, and at days 7 and 14 post-HLI. For detection of the efficiency of in-vivo knockdown, a separate group of mice were euthanized at days 0 (n=3), 3 (n=6) and 7 (n=3), and miR-93 expression was quantitated using real-time qPCR.

In vivo Over-expression of miR-93: PremiR-93 (Catalog # PM10951; mature sequence-CAAAGUGCU-GUUCGUGCAGGUAG; SEQ ID NO:7) or miR-mimic negative controls (scramble) (Cat#4464058, Ambion, Austin, Tex.) were dissolved in PBS, and a total dose of 300 µM of premiR-93 or negative control was delivered to each mouse intramuscularly by injecting into two sites of the gastrocnemius muscle (100 µM in 25 µl at each site), and one site in the TA muscle (100 µM in 25 µl). This method was adapted from Ge et al.[20] Injections were given at day 0, 30-minutes prior to surgery. For detection of the efficiency and duration of miR-93 over-expression, a separate group of mice were euthanized at days 4 and 10 (n=3/time point) and miR-93 expression in the gastrocnemius muscle was quantitated using real-time PCR.

Statistics: Statistical analysis was done using Graph-pad Prism software. Unpaired t-test was used for comparison between two groups, and comparison in experiments containing three or more groups was done using one-way ANOVA and Tukey's post-hoc test. Statistical significance was set at a p value of <0.05. For analysis of micro-RNA micro-array, the normalized data was fitted to a linear model for genotype and treatment. Significance of these effects was calculated with an F-test (with a James-Stein Shrinkage estimate) between groups in a factorial ANOVA design. P-values were calculated by performing 1000 permutation of samples to break association to expression values and corrected for multiple comparisons by adaptive false-discovery rate (FDR) transformation.

Supplemental Material

Supplemental Methods:

Cell Culture: Pooled HUVECs were purchased (Cell Applications Inc, San Diego, Calif.), and grown in standard endothelial cell growth medium with 10% FBS (Cell Applications Inc, San Diego, Calif.). C2C12 cells were cultured on DMEM with 10% FBS. For in-vitro transfection studies, a reverse transfection protocol using neofx transfection agent (Ambion, Austin, Tex.) was used. AntimiR-93 (MH10951), miRNA inhibitor negative control (Cat. #44640760), premiR-93 (PM10951) or miRNA mimic negative control (Cat. #4464058) were purchased from Ambion, Austin, Tex. Initial dose response experiments were done on HUVECs and C2C12 cells to determine the dose and time course for efficient knockdown of miR-93. Based on these experiments, a dose of 15 nM of antimiR-93 or premiR-93 and their respective controls were used to knockdown or over-express miR-93 in HUVECs. For C2C12, a dose of 120 nM was used for antimiR-93 or premiR-93 and their respective controls. Cell proliferation, tube formation and apoptosis assays were done 48 hours after transfection.

Cellular Apoptosis: Cells were plated in a 96-well plate at a density of $1*10^4$ cells/well for HUVECs and for C2C12, cells were plated at a density of $0.5*10^4$ (for premiR-93 vs. Scramble) or $1*10^5$ (Scramble vs. AntimiR93). After 24-hours of transfection, miR-93 modulated cells were exposed to hypoxia (2% oxygen, BioSpherix, Lacona, N.Y.) and serum starvation (HSS) to simulate ischemia in vitro. HUVECs were exposed to 48-hours of HSS, while C2C12 cells were exposed to 3-hours of HSS. A shorter time course of exposure to HSS for C2C12 cells were selected based on preliminary experiments that showed that C2C12 cells show significant cell death with longer duration of HSS. At the end of incubation, apoptosis in cells was determined using a TUNEL assay (TiterTACS, Trevigen Gaithersburg, Md.). TACS nuclease treated wells were used as positive control, while wells without addition of TdTs were used as negative controls. Each experiment was repeated at least three times.

Cell Proliferation: Cells were plated in a 96-well plate at a plating density of $5*10^3$ cells/well for HUVECs and at a density of $0.5*10^3$ (for premiR-93 vs. Scramble) or $1*10^3$ (Scramble vs. AntimiR93) for C2C12 cells. Cell proliferation was assessed 48 and 72 hours after plating using tetrazolium dye incorporation (BioVision, Milpitas, Calif.), and by doing manual cell counts after trypan blue staining to exclude dead cells. Experiments were repeated three times.

In vitro Angiogenesis Assay: After 48-hours of transfection, miR-93 modulated HUVECs were plated on matrigel to assess tube formation. PremiR-93 or Scramble transfected cells were plated on growth factor reduced matrigel (Cat #356231, BD Biosciences, Bedford, Mass.) at a cell density of 30,000 cells/well in a 48-well plate, and cells were cultured under conditions of 0% or 5% low serum growth medium (Life Technologies, NY). Similarly, antimiR-93 or scramble transfected cells were plated on growth factor enriched matrigel (Cat. #356234, BD Biosciences, Bedford, Mass.), and grown under conditions of 0% or 5% mixture of endothelial cell growth factors (EGM CC-3124, Lonaza, Allendale, N J). Endothelial cell tube formation was assessed 6 hours after plating. Each condition was done in triplicates. Four representative pictures were taken from each well under 100× magnification, and total complete tube numbers were counted and expressed as tube numbers per square mm.

Capillary Density: For assessment of capillary density, 21 days post-HLI, ischemic gastrocnemius muscles from pre-miR-93 and Scramble treated BALB/cJ mice were flash frozen in OCT compound and sectioned at 7 µm thickness. Sections were first blocked with 5% normal goat serum, and then incubated with rat anti-CD 31 antibody (1:25, BD Biosciences cat #550274) at 4° C. overnight. Sections were then washed with PBS and probed with alexa-555 conjugated goat anti-rat IgG at 1:25 dilution for 1 hour at room temperature. Sections were washed with PBS and mounted with Vectashield mounting medium (Vector Lab, Burlingame, Calif.). Secondary antibody only without primary antibody was used as negative control to assess non-specific binding. Three representative pictures from each section were taken under 400× magnification, using Olympus BX51 high-magnification microscope. Total number of CD31 positive spots/field and total number of muscle fiber/field were counted, and capillaries expressed as CD31 positive spots/ muscle fiber.

Results

Micro-RNA-93 is differentially regulated in ischemic hind-limb muscle of C57B1/6J mice versus BALB/cJ mice following hind-limb ischemia. From an initial micro-RNA micro-array, we used comparative micro-RNA profiling and identified miR-106b and miR-93 as the top two micro-RNAs whose expression displayed the most statistical significant interaction with strain and ischemia combined (nominal p values of 0.007 and 0.008 respectively). We then measured the expression of miR-93 and miR-106b using real-time-PCR. Compared to BALB/cJ mice, C57B1/6J mice showed a higher level of miR-93 expression in non-ischemic muscle (FIG. 1a). While differences in levels of miR-106b were directionally similar, it was not statistically different (FIG. 1b). At time points following HLI, miR-93 expression in the hind-limb muscle was increased ~5-fold at day 3 (a time point when perfusion recovery was comparable between the strains) and remained elevated ~3-fold at day 7 post-surgery in muscle from C57B1/6J mice, while BALB/cJ mice did not show this increase in miR-93 in ischemic/non-ischemic muscle (FIG. 1c). Thus, the strain with better perfusion recovery had a greater level of miR-93 prior to ischemia, and greater up-regulation of miR-93 post-HLI.

Interestingly, both miR-106b and miR-93 are transcribed as a single pre-micro-RNA from intron-13 of the MCM-7 gene. Therefore, we measured the expression of MCM-7 using real-time-PCR. In non-ischemic muscle, MCM-7 mRNA levels were higher in C57B1/6J mice compared to BALB/cJ (C57BL/6J vs. BALB/cJ relative expression: 1.02±0.11 vs. 0.69±0.08; p=0.04; mean±SEM; n=5/group). At day-3 post-HLI, there was significant increase in MCM-7 levels in ischemic muscles of C57BL/6J mice (relative expression, non-ischemic vs. ischemic: 1.11±0.32 vs. 3.87±0.95; mean±SEM; p=0.04; n=4/group). While MCM-7 expression in BALB/cJ non-ischemic vs. ischemic tissue was directionally similar, it was not significantly different (relative expression, non-ischemic vs. ischemic: 1.04±0.2 vs. 2.31±0.78; mean±SEM; p=ns; n=4/group). The pattern of MCM-7 expression in C57BL/6J and BALB/cJ mice paralleled the expression of miR-93, indicating co-regulation of the miR-106b-25 cluster with its host gene. We also checked the expression of miR-26b, another micro-RNA that was not differentially regulated by strain or ischemia based on the micro-array results. Quantitative PCR did not show any difference in levels of miR-26b between C57B1/6J and BALB/cJ mice (Supplemental FIG. 1). List of the micro-RNAs based on statistical significance of differential expression (p values) between the strains in the absence of ischemia and those that showed the most differential change with ischemia are shown in Supplemental Table 1.

Figure 2D:
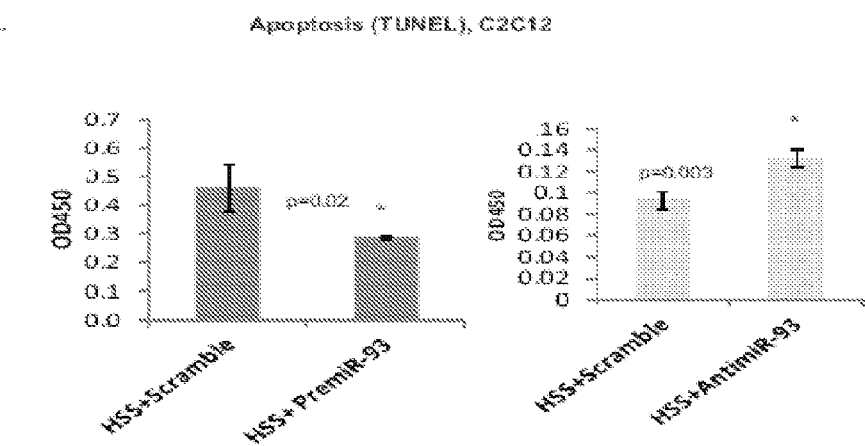

A Role for micro-RNA-93 in cells in vitro: in the absence of injury and in response to hypoxia and serum starvation (HSS). We studied HUVECs as representative endothelial cells, and C2C12 (an immortalized mouse muscle cell line) as representative skeletal muscle cells. We found that miR-93 was expressed in both cell types, and following HSS, miR-93 is upregulated in both cell types (FIG. 2a). To identify a direct role of miR-93 in response to hypoxic injury, miR-93 was over-expressed or knocked down in HUVECs and C2C12 cells. Scramble antimir or scramble miR-mimic sequences were used as controls for knockdown or over-expression experiments respectively. Antimir-93 transfection reduced miR-93 expression by ~80% in HUVECs and by ~60% in C2C12 cells (Supplemental FIG. 2, a-b). PremiR-93 transfection resulted in >100-fold over-expression of miR-93 in both cell types (Supplemental FIG. 2, c-d). Even in the absence of any external injury, knockdown of miR-93 resulted in up-regulation of caspase-9, a marker of apoptosis in both HUVECs and C2C12 cells (FIG. 2b). Following HSS, over-expression of miR-93 attenuated apoptosis, while knockdown of miR-93 increased apoptosis in both endothelial (FIG. 2c), and C2C12 cells (FIG. 2d). Collectively, these results indicate that miR-93 mediates cell survival in response to HSS in both endothelial and skeletal muscle cells.

Figures 2E, 2F, 2G:
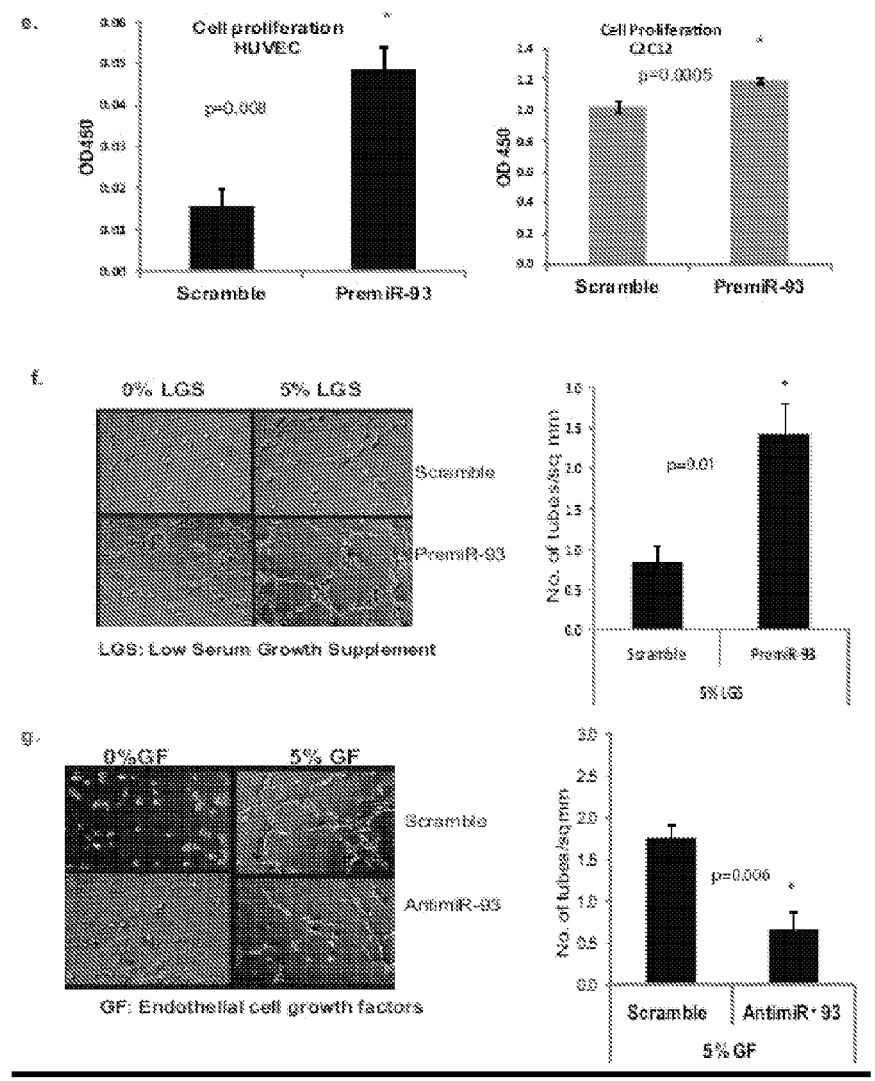

Over-expression of miR-93 enhances cell proliferation and endothelial cell tube formation. The angiogenic response to ischemia includes endothelial cell survival, proliferation, and migration. We first investigated the effects of miR-93 over-expression in cell proliferation. Over-expression of miR-93 enhanced proliferation in both endothelial and C2C12 cells (FIG. 2e). Next, we evaluated the effect of miR-93 over-expression or knockdown on endothelial cell tube formation in matrigel models. Over-expression of miR-93 enhanced endothelial cell tube formation (FIG. 2f), while knockdown of miR-93 attenuated endothelial cell tube formation (FIG. 2g). Interestingly, and unexpectedly, this effect was independent of changes in VEGF levels in HUVECs with miR-93 modulation (Supplemental FIG. 3). Collectively, these data indicate a pro-angiogenic role of miR-93 in-vitro.

Micro-RNA-93 regulates multiple genes in both endothelial cells and C2C12 cells: Micro-RNA-93 has been shown previously to target and down-regulate mRNA levels of several genes that could play important roles in cell proliferation and in recovery from hind-limb ischemia, including integrin-beta-8[21], VEGF-A[22], E2F-1, p21[23,24], and PTEN[25]. Using quantitative real-time-PCR, we first investigated the effects of miR-93 modulation on the expression of these known mRNA targets of miR-93 in HUVECs and C2C12 cells treated with HSS. Since HUVECs express relatively high levels of miR-93 and these levels are increased several folds in response to HSS (FIG. 2a), we chose to knockdown miR-93 in HUVECs and to over-express miR-93 in C2C12 cells. Table 1 summarizes these results. In HUVECs with miR-93 knockdown, the expression of p21 and E2F-1 increased, while levels of VEGF-A and Integrin-beta-8 did not change. The VEGF-A result was unexpected because Long et al. (22) showed that mirR-93 down-regulated VEGF in their studies under hyperglycemic conditions. This further suggests that use of an agonist of miR-93 would not be useful for treating PAD or ischemia. Conversely, in C2C12 cells with miR-93 over-expression, p21 and E2F-1 levels decreased, while, unexpectedly, VEGF-A, PTEN, and integrin-beta-8 levels did not change. Since p21 and E2F-1 are known components of the cell cycle pathway, we examined other genes in this pathway including MCM-7, TGFβ-1, and p53. While p53 was up-regulated in HUVECs with miR-93 knockdown, it did not change with over-expression in C2C12 cells. MCM-7 and TGFβ-1, two other genes in the cell cycle pathway that are also predicted targets of miR-93 based on computational models, were not affected by miR-93 modulation in both cell types. Cumulatively, our data indicate that in two different cell types in-vitro, miR-93 regulates multiple genes in the cell cycle pathway, resulting in gene expression changes that are expected to reduce apoptosis and enhance cell proliferation.

Figures 3A, 3B:
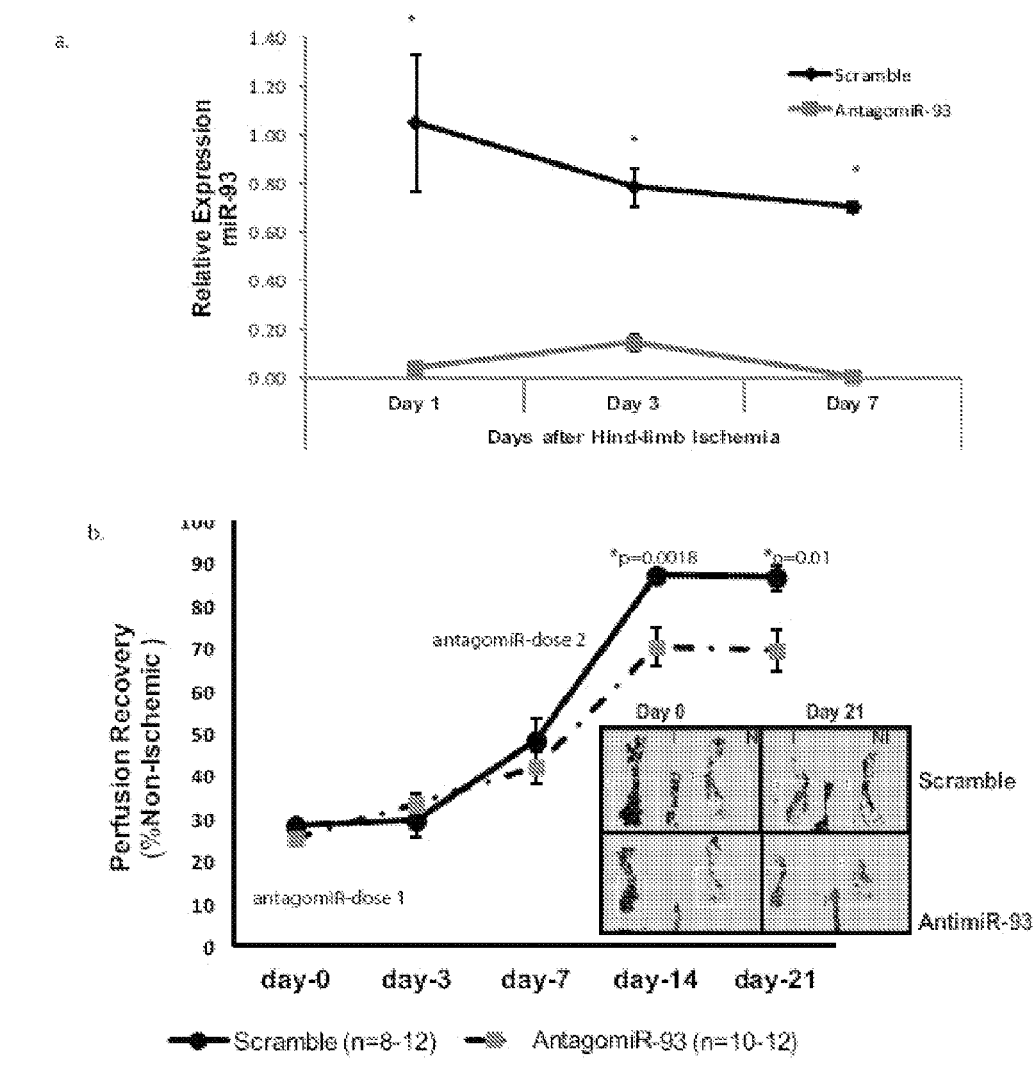
FIG. 3. Modulation of miR-93 regulates perfusion recovery in C57BL/6J (B6) and BALB/cJ (BC) mice. (a) A single intravenous dose of antagomir-93 (8 mg/kg bw) given prior to hind-limb ischemia (HLI) effectively knocked down miR-93 in the ischemic GA muscle compared to scramble treated mice. This effect was seen as early as day 1, and was persistent until at least day 7 post-HLI. Data are mean±SEM, n=3/group at days 1 and 7, n=6 at day 3; *p<0.01 at all time points (b) C57Bl/6J mice received three intravenous doses of antagomir-93 or scramble (8 mg/kg bw prior to HLI and repeated at day 7 and 14 post-HLI). Perfusion recovery in the hind-limb was monitored using Doppler imaging. Antagomir-93 treated mice showed significantly impaired perfusion recovery compared to scramble treated mice at day 14 and day 21 post-HLI (n=8-12/group, data represents mean±SEM). (c) Local intramuscular injections of premiR-93 or miR-mimic negative control (100 nM in 25 µl in two sites in the GA and 100 nM in 25 µl one site in TA) were done prior to induction of HLI. Following HLI, ischemic tissue of premiR-93 treated mice showed significant up-regulation of miR-93 at day 4, and this effect was persistent until day 10-post-HLI. (n=3/group/time point; data are mean±SEM). (d) BALB/cJ mice received a single intramuscular injection of premiR-93 prior to induction of HLI, and post-HLI perfusion recovery was monitored using Doppler imaging. PremiR-93 treated mice showed significantly improved perfusion recovery compared to scramble treated mice at day 14 and day 21 post-HLI (n=9-12/group, data represents mean±SEM). (e) At day 21 following HLI, ischemic gastrocnemius muscle from premiR-93 treated mice showed significantly higher capillary density compared to scramble treated mice (Average capillaries/muscle fiber, Scramble vs. PremiR: 1.2±0.1 vs. 1.8±01, p=0.004, data represents mean±SEM. IGA=21-day post-HLI ischemic gastrocnemius muscle).

Inhibition of miR-93 in-vivo using systemic antagomir treatment attenuates perfusion recovery from hind-limb ischemia in C57B1/6J mice: C57B1/6J mice recover remarkably well from HLI while the response in BALB/cJ mice is much poorer. C57B1/6J mice also have higher levels of expression of miR-93 in non-ischemic muscle and show increased miR-93 expression following ischemia. To test whether miR-93 modulates the response to HLI, C57B1/6J mice were treated with systemic antagomir-93. Scramble treated mice were used as controls. A single intravenous injection of antagomir-93 given 30-minutes prior to surgery knocked down miR-93 expression effectively starting at day −1, and this effect was evident even at 7-days post-injection (FIG. 3a). This effect was selective to miR-93, as levels of two other micro-RNAs with seeding sequence similarity to miR-93, miR-17 and miR-106b were not significantly affected (Supplemental FIG. 4, a-b). Antagomir-93 or scramble sequences were injected on day 0, 7, and 14 of HLI, and perfusion recovery was monitored using Doppler imaging. Consistent with miR-93's pro-angiogenic role in-vitro, antagomir-93 treated mice showed impaired perfusion recovery starting at day 14 following HLI compared to scramble treated mice (FIG. 3b). These results demonstrate that inhibiting miR-93 is effective for inhibiting perfusion recovery.

Figures 3C, 3D:
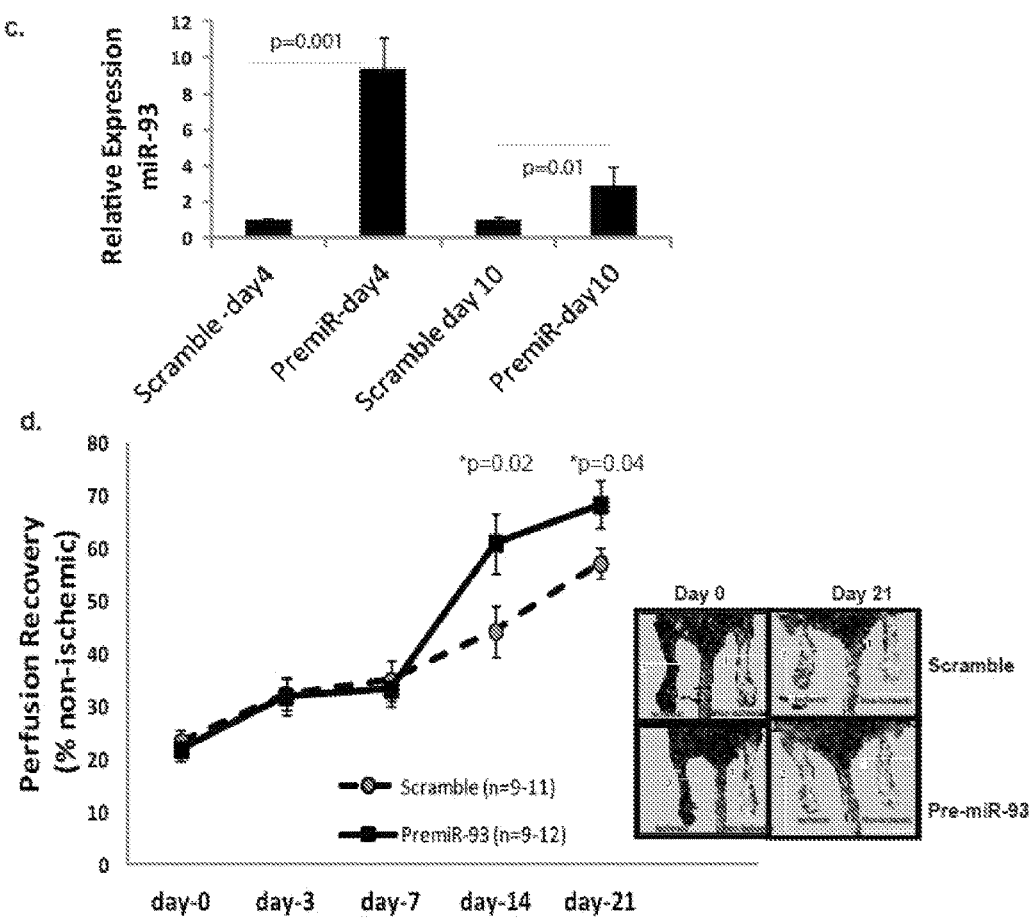
Figure 3E:
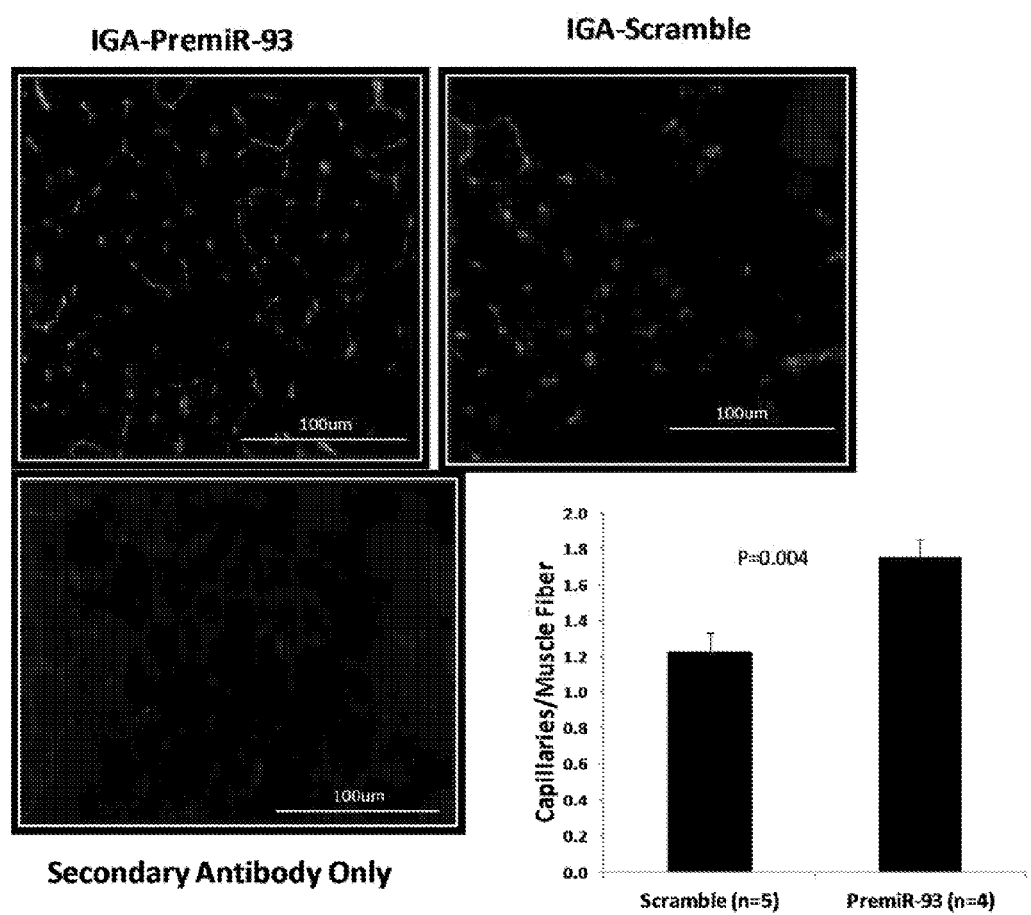

Over-expression of miR-93 in BALB/cJ mice improves perfusion recovery: When compared to C57B1/6J mice, BALB/cJ mice have lower miR-93 expression at baseline, and do not show an increase in miR-93 following HLI. To investigate whether miR-93 over-expression following HLI is sufficient to improve perfusion; we over-expressed miR-93 in BALB/cJ mice using local intramuscular injections of premiR-93 (miR-mimic) and scramble controls. Local intramuscular injection of premiR-93 resulted in significant over-expression of miR-93 that lasted at least up to 10-days post-injection (FIG. 3c). As such, premiR-93 was injected 30-minutes prior to induction of HLI. Following hind-limb ischemia, BALB/cJ mice with over-expression of miR-93 showed enhanced perfusion recovery compared to scramble treated controls (FIG. 3d). Consistent with improved perfusion recovery, at day 21 post-HLI, ischemic muscle from premiR-93 treated mice showed higher capillary density compared to scramble treated mice (FIG. 3e).

In vivo effects of miR-93 on perfusion recovery are mediated via down-regulation of multiple genes in the cell cycle pathway. We first looked at the expression of p21, E2F-1, and p53 in ischemic muscle tissue from C57BL/6J and BALB/cJ mice with miR-93 modulation. Consistent with in vitro results, knockdown of miR-93 in C57BL/6J mice up-regulated expression of p21 and p53 at both mRNA and protein levels, while E2F-1 was up-regulated only at the protein level (FIG. 4, a-b). Consistent with these findings, miR-93 over-expression in ischemic hind-limb muscle from BALB/cJ mice was associated with decreased levels of p21, E2F-1 and p53 at both mRNA (FIG. 4c) and protein levels (FIG. 4d) when compared to scramble treatment.

Figure 4A:
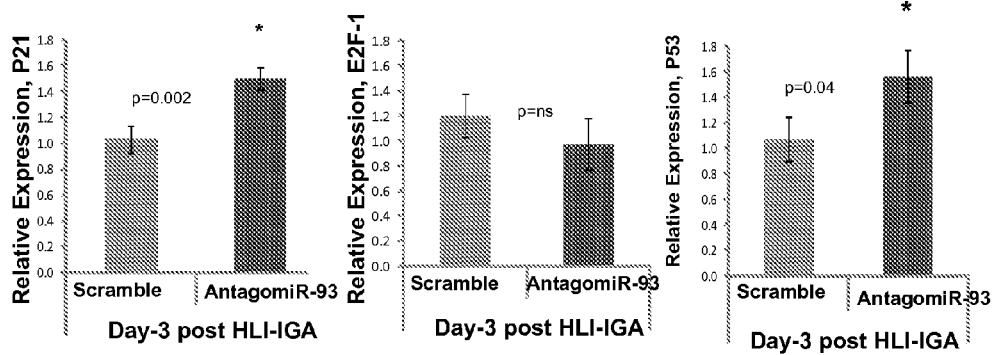
FIG. 4. Gene changes in ischemic muscles with miR-93 modulation in-vivo in C57Bl/6J and BALB/cJ mice. (a) In gastrocnemius (GA) muscle from C57BL/6J mice at day 3 post-HLI, miR-93 knockdown resulted in increased mRNA levels of p21 and p53 compared to scramble treated mice, while E2F-1 levels were not different at the mRNA level (b) In GA muscle from C57BL/6J mice at day 3 post-HLI, miR-93 knockdown resulted in increased protein levels of p21, E2F-1 and P53 compared to scramble treated mice as assessed by western blot. (n=6/group; data represent mean±SEM). At day 3 post-hind-limb ischemia, ischemic GA from BALB/cJ mice with miR-93 over-expression showed down-regulation of p21, E2F-1 and p53 at both mRNA (c) and protein (d) levels compared to scramble treated mice (n=6/group; data represent mean±SEM; western blot quantitation done using densitometry, expression levels normalized to actin). (e). heat map of the genes in the cell cycle pathway in ischemic (IGA) vs. non-ischemic (NGA) gastrocnemius muscle from untreated BALB/cJ mice at day 3 post-hind-limb ischemia. P21, E2F-1, and p53, all three genes downregulated by miR-93 over-expression in BALB/cJ mice were upregulated in ischemic muscles from untreated BALB/cJ mice. Other highlighted genes are known and/or predicted targets of miR-93 based on literature and computational predictions, but were not found to be changed with miR-93 modulation in our experiments.
Figure 4B:
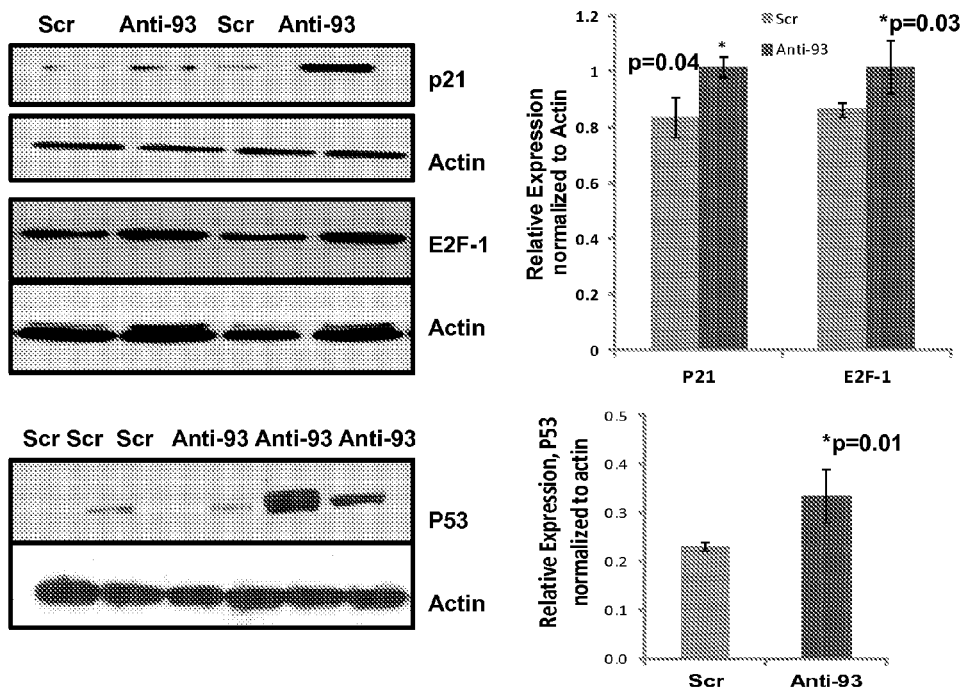
Figure 4C:
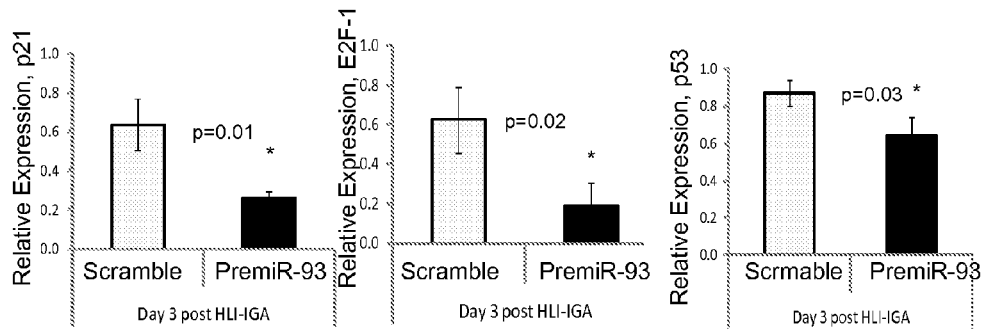
Figure 4D:
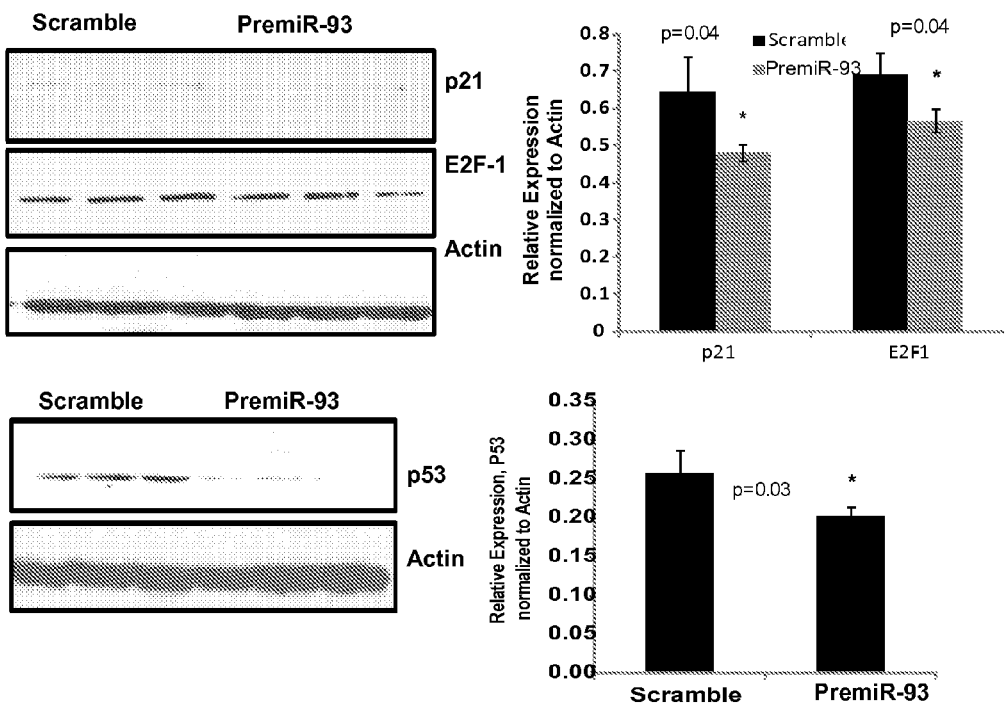
Figure 4E:
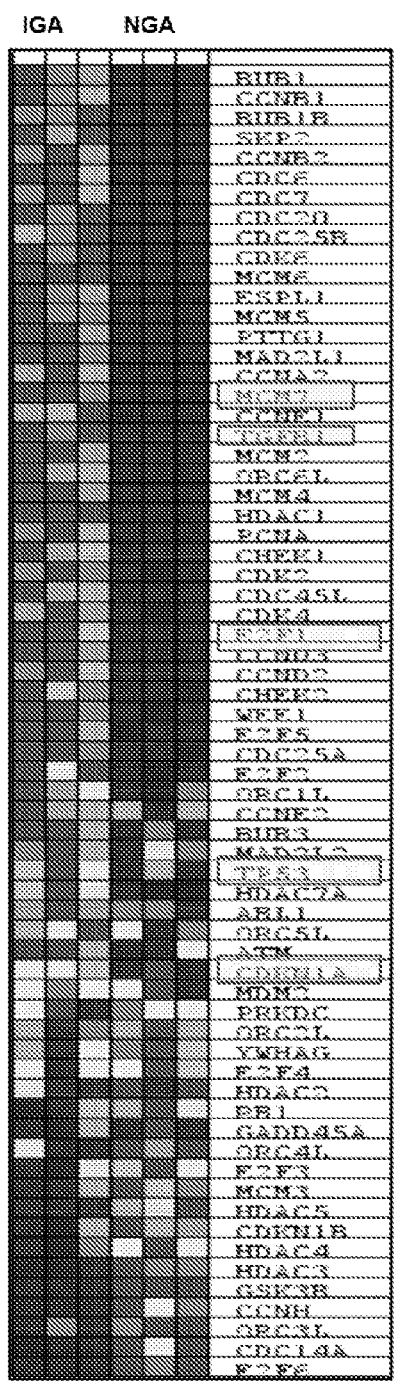

To investigate other potential genes/pathways that could play a role in improving perfusion recovery in vivo and could be linked to miR-93, we first did mRNA micro-array of ischemic vs. non-ischemic muscle of untreated BALB/cJ mice. Gene Set Enrichment Analysis (GSEA)[18] of microarray results showed 847 pathways to be up-regulated in ischemic tissue of BALB/cJ mice compared to non-ischemic tissue (Table 2 shows the top twenty pathways up-regulated in Ischemic vs. non-ischemic tissue, BALB/cJ; FDR <0.25; full list in Supplemental Table 2). We next analyzed mRNA micro-array of HUVECs under HSS with scramble versus antimiR-93, and looked for pathways that are up-regulated under miR-93 knockdown. GSEA analysis revealed 17 pathways to be up-regulated (with FDR <0.25) in response to miR-93 knockdown in HUVECs (Table 2). Interestingly, the cell cycle pathway was the only common pathway that was identified to be up-regulated both in antimiR-93 treated HUVECs and in BALB/cJ mice ischemic muscle. FIG. 4e shows the heat map of genes in the cell cycle pathway in ischemic vs. non-ischemic muscle from untreated BALB/cJ mice, with p21, p53, and E2F-1 up-regulated in the ischemic vs. non-ischemic muscle. When miR-93 was over-expressed in BALB/cJ mice, all three of these genes were down-regulated compared to scramble treated mice (FIG. 4, c-d). Conversely, when miR-93 was knocked down in C57B1/6J mice, p21, E2F-1 and p53 were all up-regulated (FIG. 4, a-b). In addition, MCM-7 and TGFβ-1, two other genes in the cell cycle pathway were also found to be potential targets of miR-93 based on computational predictions using TargetScan and MiRanda. However, when we proceeded to quantify changes in gene expression, these genes were not affected by miR-93 over-expression or knockdown in-vivo. In addition, we also examined the expression of thirteen other known and/or predicted targets of miR-93 across three other pathways that are up-regulated in ischemic tissue of untreated BALB/cJ mice. These genes were not affected by miR-93 over-expression or knockdown in-vivo. Table 3 summarizes all the genes examined, pathways involved, and changes in response to miR-93 modulation in-vivo. These observations indicate that over-expression of miR-93 in HLI modulates multiple genes in the cell cycle pathway that work in concert to reduce ischemia-induced apoptosis and enhance endothelial cell proliferation, thereby enhancing perfusion recovery following hind-limb ischemia.

Discussion

While micro-RNAs have been established to play key roles in diseased/injury states, there is limited information on the role of micro-RNAs in PAD. While our study is not the first one to identify the role of micro-RNAs in recovery from hind-limb ischemia, there are several novel aspects of our study. First, we utilized two phenotypically different inbred mouse strains to identify micro-RNAs with potential roles in adaption to ischemia, whereas prior studies have identified the target micro-RNAs based on micro-RNA micro-array from HUVECs[8] or between non-ischemic vs. ischemic tissues of a single strain of mouse[9]. The use of different mouse strains with different adaptations to HLI examined at a time-point when the recovery is comparable is an alternative non-biased strategy. Second, our in-vitro experiments show that miR-93 exerts both proliferative and anti-apoptotic effects in two different cell types relevant to perfusion recovery from HLI, and in-vivo, we confirmed miR-93's role on perfusion recovery with both gain and loss of function techniques. Third, our experiments indicate that miR-93 mediates its effects via regulation of multiple genes in the cell cycle pathway, and not via regulation of a single gene.

Using C57B1/6J mice as a model with a favorable adaptive response to HLI and BALB/cJ mice as a model with a poor adaptive response, we identified micro-RNA-93 as one of the micro-RNAs with the most consistent difference based on strain and ischemia. Follow-up in-vitro studies indicate that miR-93 is expressed in both endothelial cells and skeletal muscle cells, and both cell-types up-regulate miR-93 in response to HSS, indicating a role of miR-93 in cellular adaptation to hypoxia/serum starvation. Micro-RNA-93 over-expression enhanced cellular survival to HSS, and enhanced endothelial cell tube formation. We used modified antagomir sequences as described by Krutzfeldt et al.[19] to knockdown miR-93 in vivo. Systemic delivery of antagomir was able to knockdown miR-93 in the skeletal muscle very effectively (FIG. 3a) and specifically (Supplemental FIG. 4a-b), as previously shown by others[8,9,19] The extent of miR-93 knockdown was comparable to that shown by Bonauer et al. at 24-h post-injection[8], and by Grundmann et al.[9] at 3 and 7-days post-injection. Grundmann et al. injected antagomiR-100 at 8 mg/kg bw via tail-vein at day 0, 1, and 2 and showed significant down-regulation of miR-100 lasting up to 7-days. This is comparable to the duration of down-regulation of miR-93 observed in our experiments after a single injection, although a direct comparison is difficult as the authors in the prior studies did not specifically look at the duration of miR suppression after a single injection. In our experiments, retro-orbital injections may have resulted in better systemic delivery compared to tail-vein injections used by others[8,9]. Similarly, our over-expression studies were comparable to that observed by Ge at al[20] using a similar technique, where they showed upregulation of miR-125b at day-1 persisting up to day-7 following intramuscular injection of miR-mimic We therefore picked day-3 as the early time point and day-10 as a late time point to check expression of miR-93 following intramuscular injection of miR-93 mimic. The present experiments (FIG. 3C) showed upregulation of miR-93 at day-3 at ~9-fold, and persistent upregulation of miR-93 until day-10 at ~3-fold, which are comparable to that shown by Ge et al. Slightly better over-expression in our studies may be explained by multiple site injections rather than a single site injection. Consistent with its in-vitro effects, in-vivo treatment of C57B1/6J mice with systemic antagomir-93 attenuated perfusion recovery, while over-expression of miR-93 in BALB/cJ improved capillary density in the ischemic muscle, and enhanced perfusion recovery. Collectively, the data indicate that miR-93 enhances endothelial cell and myocyte survival and proliferation, and enhances angiogenesis to improve recovery from hind-limb ischemia.

MiR-93 is a member of the 106b-25 cluster of miRs, which is transcribed from intron-13 on the MCM-7 gene on chromosome 5 in mice and 7 in humans[24]. MCM-7 is a highly conserved mini-chromosomal maintenance protein essential for eukaryotic DNA replication. Elevated MCM-7 expression has been associated with various tumors[26]. Similarly, miR-93 over-expression has also been described in many different tumors, indicating its role in tumor survival/angiogenesis. However, the present described study is the first to investigate its role in ischemia-induced angiogenesis in a model of PAD. Like many other intronic micro-RNAs, miR-93 has been shown to regulate many genes that are involved in pathways related to its host gene. Several of miR-93 predicted and experimentally validated targets in tumor cells include cell cycle regulatory and pro-apoptotic proteins. MiR-93 has been shown to directly target E2F-1 in gastric adenoma cells and prevent TGF-β mediated apoptosis[24]. Excess levels of E2F-1 have been shown to mediate cellular apoptosis[27,28], and E2F-1 k/o mice exhibit improved perfusion recovery[29]. MiR-93 has also been shown to directly target p21 and enhance cell cycle progression[23], and to promote tumor growth in glioblastoma cells by inhibiting integrin-beta-8[21]. However, much of Fang et al. was due to indirect effects and interaction by one cell type with another[21]. That is, it appears that Fang was studying paracrine or cell-cell interactions. In addition, another key protein involved in cell cycle pathway, p53, was also regulated by modulation of miR-93 in our experiments. While it is possible that the regulation of p53 is by direct transcriptional or translational repression, it can also be downregulated as a secondary effect from other gene changes. Recent studies have shown that p53 mediates hypoxia-induced endothelial cell death[30], and knockdown of p53 attenuated anoxia-induced cell death in cardiomyocytes[31]. Therefore, by downregulating p21 and p53, miR-93 enables cell cycle progression and increased cellular proliferation, while it limits ischemia-induced apoptosis by downregulating E2F-1 and p53. The ability of miR-93 to regulate multiple genes that converge in complementary functional pathways makes it a potent regulator of perfusion recovery from hind-limb ischemia. The 106-25 cluster knockout mice that lacks miR-93 (in addition to other members of this cluster, miR-106b and miR-25) do not exhibit any phenotype under normal circumstances[32], while knockout of its paralog cluster, miR-17-92 results in neonatal death[32]. However, knockout of 106b-25 cluster in addition to miR-17-92 cluster (double knockout) worsens the miR-17-92 knockout phenotype by inducing fetal death mid-gestation. This indicates that the role of miR-93 is likely more pronounced primarily in the setting of another injury/ischemia.

Long et al. showed that miR-93 directly targets and reduces VEGF-A expression in cultured podocytes and glomeruli[22]. Surprisingly, despite predictions based on the work of Long that miR-93 would regulate VEGF-A, it is disclosed herein in both cultured HUVECs and in vivo, that VEGF-A expression was not affected by miR-93 modulation. The present application therefore discloses the unexpected result that miR-93 can regulate biologic functions, such as enhancing perfusion recovery of ischemia, independently of regulating VEGF, while others, such as Long et al. (22) have shown that miR-93 regulates VEGF. Therefore, based on prior publications it would have been predicted that an agonist of miR-93 would not be useful for treating PAD or ischemia, which is contrary to the result disclosed herein. Without wishing to be bound by any particular theory, it is theorized herein that micro-RNA regulation of target genes may likely be context and cell-type dependent, and thus not predictable. Also, as seen in our studies, miR-93 expression has been shown to parallel expression of MCM-7, indicating co-regulation of miR-93 with its host gene[24]. It has been shown that HIF-1α negatively regulates MCM-7 expression[34], and MCM-7 in turn destabilizes HIF-1α and inhibits its action[34]. In addition, Manalo et al. compared gene expression profiles in arterial endothelial cells cultured under normoxic and hypoxic conditions and in non-hypoxic cells infected with constitutively active HIF-1α, and showed the genes induced and repressed by HIF-1α. MCM proteins were found to be repressed by HIF-1α[35]. Given this, it is most likely that upregulation of MCM-7 and miR-93 under hypoxia in C57B1/6 mice is independent of HIF-1α, and therefore, miR-93 modulation of ischemia-induced angiogenesis is a potential novel mechanism independent of traditional HIF-1α regulated angiogenic genes. Based on the art described herein, the present application discloses unexpected results regarding regulation of miR-93 and reperfusion recovery and other issues associated with ischemia.

While rates of death from ischemic heart disease in the United States are declining, peripheral arterial disease of the lower extremity has not declined. PAD can be expected to become an even greater health care problem in the years ahead. The primary problem in PAD is reduced blood flow to the leg and since total occlusions in one or more of the major inflow arteries to the leg(s) is common in patients with PAD, blood flow to the leg becomes dependent on the number and extent of collateral blood vessels and their ability to connect to the distal microvasculature in ischemic muscle.

Current medical therapies used to treat patients with PAD are for systemic atherosclerosis but these agents do not treat the primary problem in PAD which is impaired blood flow. In a simple model, a single miR can bind to the 3' untranslated region of a single mRNA and target that mRNA for degradation. However, a single miR can bind to several functionally related mRNA's and thereby regulate entire biologic pathways. Utilized herein are in vivo models, a computational approach, in-vitro and gene expression studies which demonstrated that miR-93 regulated several genes simultaneously to orchestrate multiple processes in skeletal muscle adaptation to ischemia. This provides the framework for the development of novel approaches for the treatment of PAD.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

TABLE 1

Summary of genes examined in-vitro with miR-93 knockdown in Human Umbilical Vein Endothelial Cells (HUVECs) and miR-93 over-expression in mouse skeletal muscle cells (C2C12). 24 HSS = Hypoxia and Serum Starvation; 3 HSS = 3 hrs of hypoxia and serum starvation.

| | HUVEC with 24 HSS AntimiR-93 vs. Scramble | C2C12 with 3 HSS PremiR-93 vs. Scramble |
|---|---|---|
| Known Targets of miR-93 (Literature supported) | | |
| P21 | Up-regulated | Down-regulated |
| E2F-1 | Up-regulated | Down-regulated |
| PTEN | Unchanged | Unchanged |
| Integrin beta-8 | Unchanged | Unchanged |
| VEGF-A | Unchanged | Unchanged |
| Other key cell cycle regulators and/or computationally predicted targets of miR-93 | | |
| P53 | Up-regulated | Unchanged |
| MCM-7 | Unchanged | Unchanged |
| TGFβ-1 | Unchanged | Unchanged |

TABLE 2

List of top twenty pathways up-regulated (Gene Set Enrichment Analysis of mRNA arrays, FDR < 0.25) in ischemic vs. non-ischemic tissue from untreated BALB/cJ mice, and list of pathways upregulated in antimiR-93 vs. scramble treated HUVECs exposed to 24-hours of hypoxia and serum starvation (24 HSS). Cell cycle pathway was the single common pathway up-regulated both in antimiR-93 treated HUVECs and in BALB/cJ mice ischemic muscle.

| Gene Sets/Pathways Upregulated in Ischemic vs. Non-Ischemic muscle from untreated BALB/cJ mice at day 3 post-hind-limb ischemia | FDR q-val | Gene Sets/Pathways Upregulated in AntimiR-93 vs. Scramble treated HUVECs exposed to 24 HSS | FDR q-val |
|---|---|---|---|
| HUMAN_TISSUE_TESTIS | 0.050 | GOLGI_VESICLE_TRANSPORT | 0.000 |
| TAVOR_CEBP_UP | 0.050 | ELECTRON_TRANSPORT_GO_0006118 | 0.126 |
| BCNU_GLIOMA_MGMT_24HRS_DN | 0.064 | OUTER_MEMBRANE | 0.140 |
| BYSTRYKH_HSC_CIS_GLOCUS | 0.065 | CELL_CYCLE_ARREST_GO_0007050 | 0.202 |
| HSA04664_FC_EPSILON_RI_SIGNALING_PATHWAY | 0.066 | APICOLATERAL_PLASMA_MEMBRANE | 0.206 |
| CELL_CYCLE | 0.066 | NEGATIVE_REGULATION_OF_CELL_CYCLE | 0.209 |
| HEMATOPOESIS_RELATED_TRANSCRIPTION_FACTORS | 0.067 | ORGANELLE_LOCALIZATION | 0.210 |
| XU_CBP_UP | 0.067 | SYNAPSE_ORGANIZATION_AND_BIOGENESIS | 0.211 |
| BASSO_REGULATORY_HUBS | 0.067 | BIOGENIC_AMINE_METABOLIC_PROCESS | 0.214 |
| DNA_DAMAGE_SIGNALING | 0.067 | ORGANELLE_OUTER_MEMBRANE | 0.214 |
| MANALO_HYPOXIA_DN | 0.067 | IMMUNE_EFFECTOR_PROCESS | 0.217 |
| RACCYCDPATHWAY | 0.067 | CELL_CORTEX_PART | 0.220 |
| HSA04110_CELL_CYCLE | 0.068 | COLLAGEN | 0.220 |
| CMV_ALL_UP | 0.068 | APICAL_JUNCTION_COMPLEX | 0.220 |
| IFN_BETA_UP | 0.069 | N_ACYLTRANSFERASE_ACTIVITY | 0.229 |

TABLE 2-continued

List of top twenty pathways up-regulated (Gene Set Enrichment Analysis of mRNA arrays, FDR < 0.25) in ischemic vs. non-ischemic tissue from untreated BALB/cJ mice, and list of pathways upregulated in antimiR-93 vs. scramble treated HUVECs exposed to 24-hours of hypoxia and serum starvation (24 HSS). Cell cycle pathway was the single common pathway up-regulated both in antimiR-93 treated HUVECs and in BALB/cJ mice ischemic muscle.

| Gene Sets/Pathways Upregulated in Ischemic vs. Non-Ischemic muscle from untreated BALB/cJ mice at day 3 post-hind-limb ischemia | FDR q-val | Gene Sets/Pathways Upregulated in AntimiR-93 vs. Scramble treated HUVECs exposed to 24 HSS | FDR q-val |
|---|---|---|---|
| PYRIMIDINE_METABOLISM | 0.070 | TIGHT_JUNCTION | 0.234 |
| WILLERT_WNT_NCCIT_ALL_UP | 0.070 | SERINE_HYDROLASE_ACTIVITY | 0.240 |
| CHANG_SERUM_RESPONSE_UP | 0.070 | | |
| HSC_MATURE_SHARED | 0.070 | | |
| GREENBAUM_E2A_UP | 0.070 | | |

TABLE 3

Summary of gene changes in the ischemic hind-limb at day 3 post-hind-limb ischemia in response to miR-93 modulation in-vivo.

| Genes | BALB/cJ PremiR-93 vs. Scramble (by qPCR and/or western blot) | C57BL/6J Antagomir-93 vs. Scramble (by qPCR and/or western blot) | Pathway/s involved |
|---|---|---|---|
| P21 | Down-regulated | Up-regulated | Cell Cycle |
| E2F-1 | Down-regulated | Up-regulated | Cell Cycle/Apoptosis |
| P53 | Down-regulated | Up-regulated | Cell Cycle/Apoptosis |
| PTEN | No change | No change | Phosphoprotein phosphatase |
| Integrin beta-8 | No change | No change | Integrin signaling |
| VEGF-A | No change | No change | Angiogenesis/proliferation |
| MCM-7 | No change | No change | Cell cycle |
| TGFβ1 | No change | No change | Cell cycle |
| Epiregulin | No change | No change | Metabolic |
| BMP-2 | No change | No change | Metabolic |
| ATP8b | No change | No change | Metabolic |
| Dusp-4 | No change | No change | Phosphoprotein phosphatase |

SUPPLEMENTAL TABLE 1

List of top ten most differentially expressed micro-RNAs by micro-Array sorted based on different comparisons. C57Bl/6J and BALB/CJ mice (n = 3/group) underwent hind-limb ischemia. At day 3-post-ischemia, total RNA was isolated from gastrocnemius muscles and an illumina micro-RNA array was done, looking for 380 mouse micro-RNAs.

| Identifier | P-value |
|---|---|
| *Top Ten Micro-RNAs Differentially Regulated by Strain and Ischemia* | |
| mmu-miR-106b | 0.0061 |
| mmu-miR-106b93 | 0.0089 |
| mmu-miR-let-7i | 0.0174 |
| mmu-miR-17 | 0.0187 |
| mmu-miR-214* | 0.0191 |
| mmu-miR-124 | 0.0192 |
| mmu-miR-540-3p | 0.0205 |
| mmu-miR-351 | 0.0214 |
| mmu-miR-204 | 0.0221 |
| mmu-miR-541 | 0.0233 |
| *Top Ten Micro-RNAs Differentially Regulated by Strain Alone* | |
| mmu-miR-339-3p | 0.0009 |
| mmu-miR-324-5p | 0.00196 |
| solexa-622-718 | 0.00236 |
| mmu-miR-106a: 9.1 | 0.00348 |
| solexa-200-2167 | 0.00377 |
| mmu-miR-338-3p | 0.00548 |
| mmu-miR-466 | 0.00568 |
| mmu-miR-127 | 0.00582 |
| mmu-miR-410 | 0.0059 |
| mmu-miR-669h-3p | 0.00919 |
| *Top Ten Micro-RNAs Differentially Regulated By Ischemia Alone* | |
| mmu-miR-101b: 9.1 | 0.00273 |
| mmu-miR-101a: 9.1 | 0.00376 |
| mmu-miR-143 | 0.00559 |
| mmu-miR-140 | 0.00622 |
| mmu-miR-879 | 0.00642 |
| mmu-miR-27a | 0.00822 |
| solexa-130-3526 | 0.009 |
| mmu-miR-30e | 0.0092 |
| mmu-miR-479 | 0.0097 |
| Mmu-miR-127 | 0.01125 |

SUPPLEMENTAL TABLE 2

Full list of pathways up-regulated (FDR < 0.25) in ischemic vs. non-ischemic tissue from untreated BALB/C mice (based on GSEA analysis of mRNA arrays).

| NAME | FDR q-val |
|---|---|
| HUMAN_TISSUE_TESTIS | 0.05 |
| TAVOR_CEBP_UP | 0.05 |
| BCNU_GLIOMA_MGMT_24HRS_DN | 0.064809084 |
| BYSTRYKH_HSC_CIS_GLOCUS | 0.06584324 |

SUPPLEMENTAL TABLE 2-continued

Full list of pathways up-regulated (FDR < 0.25) in ischemic vs. non-ischemic
tissue from untreated BALB/C mice (based on GSEA analysis of mRNA arrays).

| NAME | FDR q-val |
| --- | --- |
| HSA04664_FC_EPSILON_RI_SIGNALING_PATHWAY | 0.06622046 |
| CELL_CYCLE | 0.06629 |
| HEMATOPOESIS_RELATED_TRANSCRIPTION_FACTORS | 0.06661608 |
| XU_CBP_UP | 0.06700018 |
| BASSO_REGULATORY_HUBS | 0.06703148 |
| DNA_DAMAGE_SIGNALING | 0.06736976 |
| MANALO_HYPOXIA_DN | 0.067468196 |
| RACCYCDPATHWAY | 0.06775575 |
| HSA04110_CELL_CYCLE | 0.067927875 |
| CMV_ALL_UP | 0.0681 |
| IFN_BETA_UP | 0.06815929 |
| PYRIMIDINE_METABOLISM | 0.068412416 |
| WILLERT_WNT_NCCIT_ALL_UP | 0.06892387 |
| CHANG_SERUM_RESPONSE_UP | 0.06946456 |
| HSC_MATURE_SHARED | 0.07003704 |
| GREENBAUM_E2A_UP | 0.07036249 |
| HSC_MATURE_ADULT | 0.07048955 |
| ALCALAY_AML_NPMC_DN | 0.07064423 |
| CCR5PATHWAY | 0.07068086 |
| UVB_NHEK3_C6 | 0.07080033 |
| GILDEA_BLADDER_UP | 0.07120818 |
| BREAST_DUCTAL_CARCINOMA_GENES | 0.07128935 |
| ELONGINA_KO_DN | 0.07134255 |
| UVC_HIGH_D2_DN | 0.071420886 |
| TFF2_KO_UP | 0.07163233 |
| DAC_PANC_UP | 0.07168678 |
| BRUNO_IL3_DN | 0.07197612 |
| HSC_LATEPROGENITORS_SHARED | 0.0720423 |
| BRG1_ALAB_UP | 0.07207382 |
| HSC_LATEPROGENITORS_FETAL | 0.07209282 |
| CALRES_MOUSE_NEOCORTEX_DN | 0.072404265 |
| ZHAN_TONSIL_PCBC | 0.072409675 |
| FSH_OVARY_MCV152_UP | 0.072438024 |
| CELL_CYCLE_KEGG | 0.07244094 |
| CELL_CYCLE_CHECKPOINT | 0.07253369 |
| UVB_SCC_UP | 0.07270865 |
| HSA04620_TOLL_LIKE_RECEPTOR_SIGNALING_PATHWAY | 0.0727895 |
| CELLCYCLEPATHWAY | 0.073041104 |
| ET743_SARCOMA_72HRS_UP | 0.07318242 |
| NAB_LUNG_DN | 0.07327142 |
| CMV_24HRS_UP | 0.073491715 |
| UVB_NHEK3_C8 | 0.07352338 |
| HEARTFAILURE_VENTRICLE_DN | 0.07356298 |
| G1PATHWAY | 0.073589124 |
| ADIP_DIFF_CLUSTER3 | 0.07372476 |
| HSC_LATEPROGENITORS_ADULT | 0.073958986 |
| BRENTANI_PROTEIN_MODIFICATION | 0.074010365 |
| GENOTOXINS_ALL_4HRS_REG | 0.0743307 |
| HSC_MATURE_FETAL | 0.07469621 |
| BECKER_TAMOXIFEN_RESISTANT_UP | 0.07480314 |
| AGED_MOUSE_HYPOTH_UP | 0.075054124 |
| IDX_TSA_DN_CLUSTER4 | 0.07523184 |
| BCNU_GLIOMA_NOMGMT_48HRS_DN | 0.07542257 |
| G1_TO_S_CELL_CYCLE_REACTOME | 0.07563645 |
| UVB_SCC_DN | 0.07579693 |
| HSA04115_P53_SIGNALING_PATHWAY | 0.075802006 |
| OLDAGE_DN | 0.07618109 |
| ZHAN_MULTIPLE_MYELOMA_SUBCLASSES_DIFF | 0.076202296 |
| GLYCOSPHINGOLIPID_METABOLISM | 0.076264076 |
| HYPOXIA_FIBRO_UP | 0.07659237 |
| HSA04650_NATURAL_KILLER_CELL_MEDIATED_CYTOTOXICITY | 0.07682923 |
| HSA00240_PYRIMIDINE_METABOLISM | 0.07692899 |
| PEART_HISTONE_UP | 0.077149995 |
| SANSOM_APC_4_DN | 0.077250384 |
| PEART_HISTONE_DN | 0.07727423 |
| SCHUMACHER_MYC_UP | 0.07762844 |
| BRENTANI_REPAIR | 0.07772115 |
| ROSS_CBF_MYH | 0.077735685 |
| HSA00052_GALACTOSE_METABOLISM | 0.07799198 |
| BLEO_HUMAN_LYMPH_HIGH_24HRS_UP | 0.07806986 |
| FSH_OVARY_MCV152_DN | 0.07836521 |
| XU_CBP_DN | 0.07838582 |
| MYC_TARGETS | 0.07874852 |
| MPRPATHWAY | 0.07914234 |
| CANTHARIDIN_DN | 0.07945373 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
| --- | --- |
| SANSOM_APC_5_DN | 0.07966169 |
| UVB_NHEK3_C5 | 0.079998754 |
| HDACI_COLON_BUT16HRS_DN | 0.08013886 |
| PENG_LEUCINE_DN | 0.08034357 |
| HDACI_COLON_BUT48HRS_DN | 0.080696404 |
| HDACI_COLON_BUT_DN | 0.08105753 |
| BRCA1_OVEREXP_PROSTATE_UP | 0.0814173 |
| BRCA_PROGNOSIS_NEG | 0.08258 |
| HALMOS_CEBP_UP | 0.0828362 |
| UVC_HIGH_ALL_DN | 0.08319704 |
| DER_IFNB_UP | 0.083263844 |
| UV-4NQO_FIBRO_DN | 0.08366139 |
| ET743_HELA_UP | 0.08442017 |
| TOLLPATHWAY | 0.08461013 |
| P21_P53_MIDDLE_DN | 0.08477871 |
| VHL_RCC_UP | 0.08497831 |
| UVC_TTD_ALL_DN | 0.08614139 |
| PENG_RAPAMYCIN_UP | 0.08632516 |
| ABRAHAM_AL_VS_MM_UP | 0.086510174 |
| GAMMA-UV_FIBRO_UP | 0.087118134 |
| KRETZSCHMAR_IL6_DIFF | 0.087196164 |
| BROCKE_IL6 | 0.08805103 |
| LEE_TCELLS5_UP | 0.088323444 |
| NKTPATHWAY | 0.08869194 |
| TPA_RESIST_LATE_UP | 0.08869298 |
| BASSO_GERMINAL_CENTER_CD40_DN | 0.08905461 |
| TGFBETA_C2_UP | 0.08911723 |
| BRENTANI_CELL_CYCLE | 0.08912608 |
| WANG_HOXA9_VS_MEIS1_DN | 0.08945446 |
| ZHAN_MMPC_EARLYVS | 0.08978339 |
| NICK_RHAPC_UP | 0.089797534 |
| TNFALPHA_4HRS_UP | 0.08988574 |
| RUIZ_TENASCIN_TARGETS | 0.09014662 |
| LVAD_HEARTFAILURE_DN | 0.09027048 |
| AGED_MOUSE_CEREBELLUM_UP | 0.09027932 |
| UNDERHILL_PROLIFERATION | 0.09050191 |
| KANNAN_P53_UP | 0.090578474 |
| P21_P53_ANY_DN | 0.09060948 |
| VANTVEER_BREAST_OUTCOME_GOOD_VS_POOR_DN | 0.09063328 |
| LINDSTEDT_DEND_DN | 0.09063949 |
| ROSS_MLL_FUSION | 0.0907165 |
| UVC_HIGH_D3_DN | 0.090725005 |
| JNK_UP | 0.09091946 |
| AGED_MOUSE_NEOCORTEX_UP | 0.090945095 |
| HYPOXIA_RCC_UP | 0.09100389 |
| TPA_SENS_EARLY_UP | 0.09125636 |
| BRENTANI_SIGNALING | 0.09132675 |
| PENG_GLUCOSE_DN | 0.09165474 |
| JISON_SICKLE_CELL | 0.091849454 |
| NEMETH_TNF_UP | 0.09209056 |
| H2O2_CSBDIFF_C1 | 0.09210463 |
| BAF57_BT549_DN | 0.09230463 |
| LEI_MYB_REGULATED_GENES | 0.092337385 |
| REOVIRUS_HEK293_DN | 0.09233815 |
| AS3_FIBRO_DN | 0.09236295 |
| UEDA_MOUSE_LIVER | 0.09240781 |
| ABRAHAM_MM_VS_AL_DN | 0.092446804 |
| ET743_SARCOMA_48HRS_DN | 0.09247453 |
| MYOD_NIH3T3_DN | 0.092498705 |
| HSA00760_NICOTINATE_AND_NICOTINAMIDE_METABOLISM | 0.092528045 |
| FLECHNER_KIDNEY_TRANSPLANT_REJECTION_PBL_UP | 0.09258354 |
| HOFFMANN_BIVSBII_BI_TABLE2 | 0.09258866 |
| ZHAN_MMPC_SIM | 0.09262444 |
| NI2_MOUSE_UP | 0.09263615 |
| HINATA_NFKB_UP | 0.092658125 |
| LEE_TCELLS9_UP | 0.09266641 |
| HG_PROGERIA_DN | 0.09268967 |
| SHEPARD_CRASH_AND_BURN_MUT_VS_WT_DN | 0.09269242 |
| SERUM_FIBROBLAST_CORE_UP | 0.09269454 |
| LIZUKA_L1_GR_G1 | 0.09270097 |
| CMV_UV-CMV_COMMON_HCMV_6HRS_UP | 0.09271182 |
| LI_FETAL_VS_WT_KIDNEY_UP | 0.0927844 |
| HSA04670_LEUKOCYTE_TRANSENDOTHELIAL_MIGRATION | 0.09279239 |
| SHEPARD_GENES_COMMON_BW_CB_MO | 0.092807256 |
| TNFALPHA_ALL_UP | 0.092820235 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
|---|---|
| JISON_SICKLECELL_DIFF | 0.09286636 |
| OXSTRESS_RPE_H2O2HNE_DN | 0.092877164 |
| BECKER_TAMOXIFEN_RESISTANT_DN | 0.09288919 |
| HOHENKIRK_MONOCYTE_DEND_DN | 0.09289221 |
| CPR_NULL_LIVER_UP | 0.09289665 |
| BYSTROM_IL5_UP | 0.09290746 |
| SHEPARD_NEG_REG_OF_CELL_PROLIFERATION | 0.09291989 |
| UVB_NHEK3_ALL | 0.092927724 |
| KENNY_WNT_UP | 0.09293406 |
| HOFMANN_MANTEL_LYMPHOMA_VS_LYMPH_NODES_UP | 0.09295821 |
| UVB_NHEK2_DN | 0.09298089 |
| ALCALAY_AML_NPMC_UP | 0.092983745 |
| NING_COPD_DN | 0.09298717 |
| GENOTOXINS_4HRS_DISCR | 0.09300757 |
| WANG_HOXA9_VS_MEIS1_UP | 0.09302454 |
| IFN_GAMMA_UP | 0.09303833 |
| TPA_RESIST_MIDDLE_DN | 0.093089424 |
| HSA00230_PURINE_METABOLISM | 0.0930917 |
| AS3_FIBRO_C4 | 0.09309298 |
| SHEPARD_CELL_PROLIFERATION | 0.09309684 |
| ADIP_DIFF_CLUSTER5 | 0.093124814 |
| GSK3PATHWAY | 0.09313526 |
| HDACI_COLON_BUT12HRS_DN | 0.09315126 |
| P53PATHWAY | 0.093157254 |
| SANSOM_APC_LOSS4_UP | 0.09318556 |
| LEI_HOXC8_DN | 0.09319186 |
| GAMMA_UNIQUE_FIBRO_DN | 0.09320535 |
| IFN_ALL_UP | 0.09322175 |
| DIAB_NEPH_DN | 0.093226776 |
| OXSTRESS_RPETHREE_DN | 0.0932322 |
| SCHRAETS_MLL_UP | 0.09324405 |
| VHL_NORMAL_UP | 0.0932444 |
| BCRABL_HL60_CDNA_DN | 0.09326578 |
| WNT_TARGETS | 0.093274444 |
| KNUDSEN_PMNS_UP | 0.09328712 |
| SANA_TNFA_ENDOTHELIAL_DN | 0.09329307 |
| LI_FETAL_VS_WT_KIDNEY_DN | 0.09329964 |
| IDX_TSA_DN_CLUSTER1 | 0.093303815 |
| TARTE_PLASMA_BLASTIC | 0.09331439 |
| YU_CMYC_UP | 0.09335085 |
| CHIARETTI_T_ALL_DIFF | 0.09335565 |
| TNFA_NFKB_DEP_UP | 0.09335753 |
| ADIPOGENESIS_HMSC_CLASS8_DN | 0.09336921 |
| CORDERO_KRAS_KD_VS_CONTROL_DN | 0.09339853 |
| ZHAN_MM_CD138_PR_VS_REST | 0.0934531 |
| GOLDRATH_CELLCYCLE | 0.09347236 |
| BRCA1_SW480_UP | 0.09348996 |
| HOFFMANN_BIVSBII_BI | 0.093538776 |
| TPA_SENS_LATE_UP | 0.09356527 |
| CMV_HCMV_TIMECOURSE_12HRS_UP | 0.09356714 |
| CELL_PROLIFERATION | 0.093600065 |
| IL6_SCAR_FIBRO_UP | 0.09360304 |
| WALKER_MM_SNP_DIFF | 0.09360719 |
| TNFR1PATHWAY | 0.093649015 |
| SASAKI_ATL_UP | 0.093665026 |
| HSA04662_B_CELL_RECEPTOR_SIGNALING_PATHWAY | 0.093780704 |
| DER_IFNG_UP | 0.09380333 |
| ET743_SARCOMA_72HRS_DN | 0.09381784 |
| HSA04520_ADHERENS_JUNCTION | 0.0938862 |
| GUO_HEX_UP | 0.09393246 |
| VERHAAK_AML_NPM1_MUT_VS_WT_UP | 0.094044015 |
| TPA_SENS_MIDDLE_DN | 0.09405091 |
| ZHAN_MMPC_SIM_BC_AND_MM | 0.09408061 |
| UVC_TTD_4HR_DN | 0.09421959 |
| IRITANI_ADPROX_VASC | 0.09429331 |
| SASAKI_TCELL_LYMPHOMA_VS_CD4_UP | 0.09433405 |
| BRG1_SW13_UP | 0.094377175 |
| IFN_ANY_UP | 0.09451051 |
| PRMT5_KD_UP | 0.094614275 |
| FALT_BCLL_IG_MUTATED_VS_WT_UP | 0.0947059 |
| GERY_CEBP_TARGETS | 0.094724044 |
| ST_DICTYOSTELIUM_DISCOIDEUM_CAMP_CHEMOTAXIS_PATHWAY | 0.094805285 |
| POD1_KO_UP | 0.094920196 |
| PASSERINI_APOPTOSIS | 0.09493991 |
| ADIP_DIFF_CLUSTER4 | 0.095222645 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
| --- | --- |
| NAKAJIMA_MCS_UP | 0.09541266 |
| LE_MYELIN_UP | 0.095552936 |
| HYPOXIA_RCC_NOVHL_UP | 0.09560426 |
| IRS1_KO_ADIP_UP | 0.095720574 |
| REOVIRUS_HEK293_UP | 0.09572745 |
| FRASOR_ER_UP | 0.09574929 |
| 4NQO_ESR_WS_UNREG | 0.09579752 |
| CELL_SURFACE_RECEPTOR_LINKED_SIGNAL_TRANSDUCTION | 0.09585844 |
| E2F3_ONCOGENIC_SIGNATURE | 0.09591108 |
| STARCH_AND_SUCROSE_METABOLISM | 0.095926255 |
| UVC_XPCS_4HR_DN | 0.09605442 |
| CAMPTOTHECIN_PROBCELL_DN | 0.09689154 |
| DORSAM_HOXA9_UP | 0.09856794 |
| HTERT_UP | 0.098945975 |
| BRCA1_OVEREXP_UP | 0.099289335 |
| UVC_HIGH_D6_DN | 0.09987931 |
| UVC_XPCS_8HR_DN | 0.10015042 |
| ICHIBA_GVHD | 0.10016795 |
| LINDSTEDT_DEND_8H_VS_48H_UP | 0.10035346 |
| PARK_MSCS_LIN2 | 0.10054283 |
| HOFMANN_MDS_CD34_LOW_AND_HIGH_RISK | 0.10060569 |
| IDX_TSA_UP_CLUSTER2 | 0.10064254 |
| CMV_HCMV_6HRS_DN | 0.1006583 |
| HDACI_COLON_BUT24HRS_DN | 0.10071625 |
| CMV_8HRS_UP | 0.10073929 |
| TAKEDA_NUP8_HOXA9_6H_DN | 0.10074499 |
| UVC_TTD-XPCS_COMMON_DN | 0.100753926 |
| CHESLER_BRAIN_HIGHEST_VARIANCE_GENES | 0.100857735 |
| IRITANI_ADPROX_DN | 0.10091207 |
| HSA03030_DNA_POLYMERASE | 0.10105875 |
| HSA00600_SPHINGOLIPID_METABOLISM | 0.10111378 |
| CHIARETTI_T_ALL | 0.10233358 |
| ST_B_CELL_ANTIGEN_RECEPTOR | 0.10370769 |
| SHEPARD_BMYB_MORPHOLINO_DN | 0.1038577 |
| CALRES_RHESUS_UP | 0.103903 |
| FALT_BCLL_DN | 0.103979364 |
| IDX_TSA_DN_CLUSTER3 | 0.10406017 |
| LINDSTEDT_DEND_UP | 0.10409972 |
| ET743_RESIST_DN | 0.10418003 |
| IL1_CORNEA_UP | 0.1041947 |
| FERNANDEZ_MYC_TARGETS | 0.10426418 |
| HSIAO_LIVER_SPECIFIC_GENES | 0.10429789 |
| MAGRANGEAS_MULTIPLE_MYELOMA_IGL_VS_IGK_DN | 0.10430001 |
| CORDERO_KRAS_KD_VS_CONTROL_UP | 0.104382195 |
| BRENTANI_DEATH | 0.10440076 |
| CANCER_UNDIFFERENTIATED_META_UP | 0.10445315 |
| HESS_HOXAANMEIS1_UP | 0.1044975 |
| HESS_HOXAANMEIS1_DN | 0.104883105 |
| RAS_ONCOGENIC_SIGNATURE | 0.10513935 |
| GALINDO_ACT_UP | 0.10551507 |
| ET743_SARCOMA_6HRS_UP | 0.10557761 |
| BRCA1_OVEREXP_PROSTATE_DN | 0.10576794 |
| UVC_XPCS_ALL_DN | 0.10595959 |
| HYPOXIA_REVIEW | 0.10605718 |
| TGFBETA_EARLY_UP | 0.10609327 |
| GAY_YY1_DN | 0.10615256 |
| PENG_GLUCOSE_UP | 0.106204465 |
| FCER1PATHWAY | 0.10621549 |
| ZHAN_MM_CD138_MF_VS_REST | 0.106245935 |
| ET743_SARCOMA_DN | 0.10628241 |
| VERHAAK_AML_NPM1_MUT_VS_WT_DN | 0.1062915 |
| FSH_GRANULOSA_UP | 0.10634685 |
| PENG_LEUCINE_UP | 0.1063795 |
| G2PATHWAY | 0.10643596 |
| TAKEDA_NUP8_HOXA9_10D_UP | 0.106542505 |
| NF90_DN | 0.10654499 |
| SMOOTH_MUSCLE_CONTRACTION | 0.10654831 |
| IL6_FIBRO_UP | 0.10658014 |
| MATSUDA_VALPHAINKT_DIFF | 0.106731914 |
| DSRNA_UP | 0.10673951 |
| PTDINSPATHWAY | 0.10679032 |
| FLECHNER_KIDNEY_TRANSPLANT_WELL_PBL_DN | 0.10681937 |
| SANSOM_APC_LOSS5_UP | 0.1069167 |
| ALZHEIMERS_INCIPIENT_UP | 0.10693791 |
| HBX_HCC_DN | 0.10699859 |

SUPPLEMENTAL TABLE 2-continued

Full list of pathways up-regulated (FDR < 0.25) in ischemic vs. non-ischemic
tissue from untreated BALB/C mice (based on GSEA analysis of mRNA arrays).

| NAME | FDR q-val |
|---|---|
| ZUCCHI_EPITHELIAL_DN | 0.107008144 |
| TPA_SENS_MIDDLE_UP | 0.10710271 |
| HOFFMANN_BIVSBII_IMVM | 0.10713769 |
| TSADAC_HYPOMETH_OVCA_UP | 0.107181855 |
| GUO_HEX_DN | 0.10719817 |
| RUTELLA_HEMATOGFSNDCS_DIFF | 0.10723969 |
| HADDAD_CD45CD7_PLUS_VS_MINUS_UP | 0.10728993 |
| HADDAD_HSC_CD7_UP | 0.10764286 |
| PROLIFERATION_GENES | 0.10782312 |
| CMV_UV-CMV_COMMON_HCMV_6HRS_DN | 0.107929885 |
| AD12_ANY_DN | 0.108007856 |
| DNA_REPLICATION_REACTOME | 0.108226836 |
| UVB_NHEK3_C7 | 0.10841111 |
| ATRIA_UP | 0.109495826 |
| HYPOXIA_NORMAL_UP | 0.109529614 |
| LEE_MYC_E2F1_UP | 0.10971624 |
| RCC_NL_UP | 0.111033596 |
| AGUIRRE_PANCREAS_CHR8 | 0.111155055 |
| PARK_RARALPHA_MOD | 0.111185774 |
| LEE_MYC_TGFA_UP | 0.111220814 |
| INSULIN_ADIP_INSENS_UP | 0.11137461 |
| IFNA_HCMV_6HRS_UP | 0.111499 |
| NGUYEN_KERATO_UP | 0.111564636 |
| CELL_CYCLE_REGULATOR | 0.111755826 |
| ACTINYPATHWAY | 0.11183212 |
| LH_GRANULOSA_UP | 0.1120178 |
| ZHAN_MM_MOLECULAR_CLASSI_UP | 0.1122046 |
| IFN_ALPHA_UP | 0.112217344 |
| RADIATION_SENSITIVITY | 0.11224026 |
| BRCA1KO_MEF_DN | 0.11230446 |
| BREASTCA_TWO_CLASSES | 0.11239252 |
| CREB_BRAIN_8WKS_UP | 0.11242606 |
| ESR_FIBROBLAST_UP | 0.11249384 |
| RADMACHER_AMLNORMALKARYTYPE_SIG | 0.11275865 |
| CMV-UV_HCMV_6HRS_UP | 0.11286231 |
| GH_GHRHR_KO_24HRS_DN | 0.11287937 |
| ROSS_AML1_ETO | 0.11306378 |
| ABBUD_LIF_UP | 0.11324926 |
| PHOSPHATIDYLINOSITOL_SIGNALING_SYSTEM | 0.11392149 |
| HSA04060_CYTOKINE_CYTOKINE_RECEPTOR_INTERACTION | 0.114121 |
| TUMOR_SUPRESSOR | 0.11430686 |
| ZHAN_PCS_MULTIPLE_MYELOMA_SPKD | 0.11449379 |
| HOFFMANN_BIVSBII_LGBII | 0.11516408 |
| GN_CAMP_GRANULOSA_DN | 0.11519823 |
| UVB_NHEK1_DN | 0.11523961 |
| HDACI_COLON_BUT30MIN_DN | 0.11574291 |
| CMV_HCMV_TIMECOURSE_ALL_UP | 0.11588081 |
| DRUG_RESISTANCE_AND_METABOLISM | 0.11592808 |
| IDX_TSA_DN_CLUSTER5 | 0.11606796 |
| ZHAN_MULTIPLE_MYELOMA_VS_NORMAL_DN | 0.116114326 |
| WANG_MLL_CBP_VS_GMP_UP | 0.11623408 |
| P21_ANY_DN | 0.1162562 |
| HPV31_DN | 0.11641858 |
| LU_IL4BCELL | 0.11644549 |
| UVB_NHEK1_C1 | 0.116604105 |
| IRITANI_ADPROX_LYMPH | 0.116790675 |
| BOQUEST_CD31PLUS_VS_CD31MINUS_UP | 0.116846606 |
| MMS_HUMAN_LYMPH_LOW_4HRS_DN | 0.11757067 |
| CIS_XPC_DN | 0.11775731 |
| KNUDSEN_PMNS_DN | 0.1180087 |
| TAKEDA_NUP8_HOXA9_16D_DN | 0.11859642 |
| UVB_NHEK1_C6 | 0.11864519 |
| NGUYEN_KERATO_DN | 0.11957301 |
| BLEO_MOUSE_LYMPH_LOW_24HRS_DN | 0.11961402 |
| CELL_MOTILITY | 0.12029685 |
| IL2RBPATHWAY | 0.12088914 |
| IDX_TSA_UP_CLUSTER3 | 0.120919846 |
| YAGI_AML_PROG_ASSOC | 0.12138579 |
| HSA00790_FOLATE_BIOSYNTHESIS | 0.12152317 |
| OLD_FIBRO_UP | 0.12157718 |
| LAL_KO_6MO_UP | 0.12162986 |
| TARTE_BCELL | 0.12164226 |
| IDX_TSA_DN_CLUSTER6 | 0.121713884 |
| HOGERKORP_CD44_UP | 0.12176959 |
| ST_TUMOR_NECROSIS_FACTOR_PATHWAY | 0.12236386 |

SUPPLEMENTAL TABLE 2-continued

Full list of pathways up-regulated (FDR < 0.25) in ischemic vs. non-ischemic
tissue from untreated BALB/C mice (based on GSEA analysis of mRNA arrays).

| NAME | FDR q-val |
| --- | --- |
| TGFBETA_ALL_UP | 0.12255479 |
| RADAEVA_IFNA_UP | 0.12449681 |
| TAKEDA_NUP8_HOXA9_3D_UP | 0.12451883 |
| UVC_LOW_C2_DN | 0.12462516 |
| UVC_HIGH_D8_DN | 0.124690294 |
| EMT_UP | 0.12471138 |
| OXSTRESS_RPETWO_DN | 0.12482102 |
| KUMAR_HOXA_DIFF | 0.12486712 |
| LEE_TCELLS3_UP | 0.124884784 |
| PARK_MSCS_BOTH | 0.12508032 |
| APOPTOSIS_KEGG | 0.12517367 |
| DAC_PANC50_UP | 0.12563193 |
| TPA_SENS_LATE_DN | 0.12654063 |
| LEE_E2F1_UP | 0.1265787 |
| MATRIX_METALLOPROTEINASES | 0.1267711 |
| UV-CMV_UNIQUE_HCMV_6HRS_UP | 0.12691027 |
| CMV_HCMV_TIMECOURSE_48HRS_DN | 0.1269645 |
| IFN_BETA_GLIOMA_UP | 0.127105 |
| HTERT_DN | 0.12722939 |
| CMV_HCMV_TIMECOURSE_ALL_DN | 0.12730068 |
| FSH_GRANULOSA_DN | 0.12736738 |
| O6BG_RESIST_MEDULLOBLASTOMA_DN | 0.12749323 |
| LH_GRANULOSA_DN | 0.12768342 |
| ST_ADRENERGIC | 0.12768647 |
| BRENTANI_CELL_ADHESION | 0.12788069 |
| BREAST_CANCER_ESTROGEN_SIGNALING | 0.1284447 |
| DNMT1_KO_UP | 0.12844634 |
| ELONGINA_KO_UP | 0.1286384 |
| SHIPP_FL_VS_DLBCL_DN | 0.12863909 |
| IL7PATHWAY | 0.12981917 |
| ZHAN_TONSIL_BONEMARROW | 0.13076092 |
| DAVIES_MGUS_MM | 0.1309579 |
| ST_T_CELL_SIGNAL_TRANSDUCTION | 0.13119389 |
| FERRANDO_MLL_T_ALL_UP | 0.13161941 |
| IFNALPHA_RESIST_DN | 0.13215357 |
| MMS_MOUSE_LYMPH_HIGH_4HRS_UP | 0.13322589 |
| UVB_NHEK4_6HRS_UP | 0.13327979 |
| STEFFEN_AML_PML_PLZF_TRGT | 0.133425 |
| SIG_BCR_SIGNALING_PATHWAY | 0.13362506 |
| MITOCHONDRIAPATHWAY | 0.13363753 |
| EGF_HDMEC_UP | 0.13382609 |
| LAL_KO_3MO_UP | 0.13402808 |
| ROTH_HTERT_DIFF | 0.1350049 |
| VEGF_MMMEC_ALL_UP | 0.13608687 |
| YAGI_AML_PROGNOSIS | 0.13608956 |
| TPA_SENS_EARLY_DN | 0.13641003 |
| AGEING_KIDNEY_SPECIFIC_UP | 0.13749892 |
| CMV_ALL_DN | 0.1379116 |
| HDACI_COLON_BUT24HRS_UP | 0.13800333 |
| BREASTCA_THREE_CLASSES | 0.13816813 |
| ETSPATHWAY | 0.138208 |
| UVC_HIGH_D9_DN | 0.13837415 |
| IRS1_KO_ADIP_DN | 0.13880534 |
| HSA05210_COLORECTAL_CANCER | 0.13900763 |
| CIS_XPC_UP | 0.13904755 |
| ZHANG_EFT_EWSFLI1_UP | 0.1392057 |
| CMV_24HRS_DN | 0.13921085 |
| SANA_IFNG_ENDOTHELIAL_DN | 0.13925274 |
| SANA_TNFA_ENDOTHELIAL_UP | 0.13937165 |
| SIG_PIP3_SIGNALING_IN_B_LYMPHOCYTES | 0.1394103 |
| FERRANDO_MLL_T_ALL_DN | 0.13945885 |
| HSA05223_NON_SMALL_CELL_LUNG_CANCER | 0.13982873 |
| PARK_RARALPHA_UP | 0.14052689 |
| GREENBAUM_E2A_DN | 0.14097859 |
| HOHENKIRK_MONOCYTE_DEND_UP | 0.1411 |
| CHAUHAN_2ME2 | 0.14122844 |
| MMS_HUMAN_LYMPH_HIGH_24HRS_UP | 0.14235373 |
| VEGF_MMMEC_12HRS_UP | 0.14276302 |
| HSA04370_VEGF_SIGNALING_PATHWAY | 0.14289977 |
| ET743PT650_COLONCA_DN | 0.142916 |
| NAKAJIMA_MCSMBP_EOS | 0.14296825 |
| HDACI_COLON_SUL48HRS_DN | 0.14306012 |
| ATMPATHWAY | 0.1431044 |
| HSA04810_REGULATION_OF_ACTIN_CYTOSKELETON | 0.14311977 |
| IFN_BETA_GLIOMA_DN | 0.14314601 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
|---|---|
| WALLACE_JAK2_DIFF | 0.1431744 |
| STRESS_TPA_SPECIFIC_UP | 0.14322004 |
| YAGI_AML_PROG_FAB | 0.14323133 |
| FALT_BCLL_UP | 0.14327726 |
| ZHAN_MM_MOLECULAR_CLASSI_DN | 0.14328639 |
| TAKEDA_NUP8_HOXA9_8D_UP | 0.14334565 |
| GPCRS_CLASS_A_RHODOPSIN_LIKE | 0.14335345 |
| STEMCELL_COMMON_DN | 0.14336893 |
| ERKPATHWAY | 0.14348094 |
| LEE_TCELLS1_UP | 0.14348719 |
| TAKEDA_NUP8_HOXA9_16D_UP | 0.14352603 |
| AD12_24HRS_DN | 0.14361675 |
| LEE_TCELLS8_UP | 0.1437899 |
| CMV_HCMV_TIMECOURSE_6HRS_DN | 0.14381593 |
| GALACTOSE_METABOLISM | 0.14390767 |
| OLDONLY_FIBRO_UP | 0.14402978 |
| SIG_CHEMOTAXIS | 0.14404705 |
| LEE_TCELLS10_UP | 0.1440939 |
| H2O2_CSBDIFF_C2 | 0.14410831 |
| POD1_KO_MOST_UP | 0.14412153 |
| HDACI_COLON_CUR2HRS_UP | 0.14414567 |
| HDACI_COLON_SUL24HRS_DN | 0.14416648 |
| CHAUVIN_ANDROGEN_REGULATED_GENES | 0.14424974 |
| H2O2_CSBRESCUED_UP | 0.14471224 |
| SPPAPATHWAY | 0.14545694 |
| SA_CASPASE_CASCADE | 0.14558618 |
| CARIES_PULP_UP | 0.14569725 |
| HSA00220_UREA_CYCLE_AND_METABOLISM_OF_AMINO_GROUPS | 0.14571595 |
| CHESLER_BRAIN_CIS_GENES | 0.14574213 |
| BLEO_HUMAN_LYMPH_HIGH_4HRS_UP | 0.14579727 |
| BRENTANI_TRANSCRIPTION_FACTORS | 0.14582695 |
| HDACI_COLON_BUT48HRS_UP | 0.14589293 |
| YAO_P4_KO_VS_WT_DN | 0.14591011 |
| HSA04120_UBIQUITIN_MEDIATED_PROTEOLYSIS | 0.14602496 |
| AGED_RHESUS_UP | 0.14604557 |
| TPA_RESIST_MIDDLE_UP | 0.14619894 |
| SERUM_FIBROBLAST_CELLCYCLE | 0.14620738 |
| FASPATHWAY | 0.14624318 |
| HSA00512_O_GLYCAN_BIOSYNTHESIS | 0.1462919 |
| ST_INTERLEUKIN_4_PATHWAY | 0.1463951 |
| ET743_SARCOMA_UP | 0.14640698 |
| CXCR4PATHWAY | 0.14641401 |
| GOLDRATH_HP | 0.14660743 |
| PROSTAGLANDIN_SYNTHESIS_REGULATION | 0.1466934 |
| EMT_DN | 0.14688298 |
| TPA_RESIST_LATE_DN | 0.14702436 |
| IRITANI_ADPROX_UP | 0.14705583 |
| BASSO_GERMINAL_CENTER_CD40_UP | 0.14707331 |
| ZHAN_MM_CD1_VS_CD2_DN | 0.14721611 |
| IGLESIAS_E2FMINUS_UP | 0.1472165 |
| WIELAND_HEPATITIS_B_INDUCED | 0.14724728 |
| LEE_MYC_UP | 0.14740938 |
| ZHAN_MMPC_LATEVS | 0.14752746 |
| CROONQUIST_IL6_STARVE_UP | 0.14758644 |
| DNMT1_KO_DN | 0.14760305 |
| CMV_HCMV_TIMECOURSE_20HRS_DN | 0.14772251 |
| IFNA_UV-CMV_COMMON_HCMV_6HRS_UP | 0.14788888 |
| UVC_TTD_8HR_DN | 0.14791833 |
| CMV_HCMV_6HRS_UP | 0.14940266 |
| ADIP_VS_PREADIP_DN | 0.14973073 |
| LINDSTEDT_DEND_8H_VS_48H_DN | 0.14978209 |
| ZHAN_MM_CD1_VS_CD2_UP | 0.14984885 |
| G13_SIGNALING_PATHWAY | 0.14997144 |
| CALCIUM_REGULATION_IN_CARDIAC_CELLS | 0.15004124 |
| REN_E2F1_TARGETS | 0.15005425 |
| KANG_TERT_DN | 0.15014863 |
| VANASSE_BCL2_TARGETS | 0.15016152 |
| DER_IFNA_UP | 0.15016164 |
| HSA04660_T_CELL_RECEPTOR_SIGNALING_PATHWAY | 0.15023437 |
| IFNALPHA_NL_UP | 0.15025584 |
| NEMETH_TNF_DN | 0.15031175 |
| CHIARETTI_ZAP70_DIFF | 0.15034086 |
| OKUMURA_MC_LPS | 0.15042824 |
| UVB_NHEK2_UP | 0.15049413 |
| UVB_NHEK3_CO | 0.15050691 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
| --- | --- |
| CMV_HCMV_TIMECOURSE_48HRS_UP | 0.15063983 |
| AGED_MOUSE_RETINA_ANY_UP | 0.15112324 |
| ET743_SARCOMA_24HRS_DN | 0.15157622 |
| TARTE_PC | 0.15170725 |
| JECHLINGER_EMT_UP | 0.15175733 |
| WERNER_FIBRO_DN | 0.15185222 |
| CMV_8HRS_DN | 0.1518977 |
| CROONQUIST_IL6_STROMA_UP | 0.15208888 |
| IL1RPATHWAY | 0.15214935 |
| AGED_MOUSE_CORTEX_UP | 0.15217562 |
| TAKEDA_NUP8_HOXA9_8D_DN | 0.1522808 |
| FLECHNER_KIDNEY_TRANSPLANT_REJECTION_UP | 0.1527369 |
| LEE_DENA_UP | 0.15282856 |
| BYSTROM_IL5_DN | 0.15415153 |
| PENG_RAPAMYCIN_DN | 0.15426636 |
| AS3_FIBRO_C3 | 0.15441811 |
| WERNERONLY_FIBRO_DN | 0.15456103 |
| LEE_TCELLS4_UP | 0.15458624 |
| AS3_FIBRO_UP | 0.15470093 |
| HEMATOP_STEM_ALL_UP | 0.15475011 |
| MUNSHI_MM_VS_PCS_UP | 0.15480834 |
| ZHAN_MMPC_SIMAL | 0.15499856 |
| RAY_P210_DIFF | 0.1550941 |
| FERRARI_4HPR_UP | 0.15518945 |
| VEGF_MMMEC_3HRS_UP | 0.15523078 |
| IFNALPHA_HCC_UP | 0.15528588 |
| HASLINGER_B_CLL_11Q23 | 0.15528953 |
| UVC_LOW_ALL_DN | 0.15533017 |
| ST_FAS_SIGNALING_PATHWAY | 0.15554893 |
| TARTE_MATURE_PC | 0.15573774 |
| PENG_GLUTAMINE_UP | 0.15592724 |
| YANG_OSTECLASTS_SIG | 0.15657431 |
| PENG_GLUTAMINE_DN | 0.15691812 |
| SANA_IFNG_ENDOTHELIAL_UP | 0.15695943 |
| ERM_KO_SERTOLI_DN | 0.15707411 |
| SHEPARD_POS_REG_OF_CELL_PROLIFERATION | 0.15714772 |
| 4NQO_UNIQUE_FIBRO_UP | 0.15733673 |
| DOX_RESIST_GASTRIC_UP | 0.15737425 |
| KUROKAWA_5FU_IFN_SENSITIVE_VS_RESISTANT_DN | 0.15743662 |
| YU_CMYC_DN | 0.15749827 |
| CTNNB1_ONCOGENIC_SIGNATURE | 0.1587554 |
| SA_B_CELL_RECEPTOR_COMPLEXES | 0.15891938 |
| ROSS_PML_RAR | 0.15902102 |
| HSA01030_GLYCAN_STRUCTURES_BIOSYNTHESIS_1 | 0.15919058 |
| GAMMA_ESR_OLD_UNREG | 0.15921193 |
| IDX_TSA_UP_CLUSTER4 | 0.15991868 |
| NO1PATHWAY | 0.16062583 |
| HDACI_COLON_SUL_DN | 0.16112022 |
| HSA00565_ETHER_LIPID_METABOLISM | 0.16131279 |
| PASSERINI_IMMUNE | 0.16215943 |
| CHANG_SERUM_RESPONSE_DN | 0.16351765 |
| ADDYA_K562_HEMIN_TREATMENT | 0.16384988 |
| HSA04512_ECM_RECEPTOR_INTERACTION | 0.16390312 |
| RUTELLA_HEPATGFSNDCS_UP | 0.1651148 |
| CMV_HCMV_TIMECOURSE_24HRS_DN | 0.16583315 |
| ST_G_ALPHA_I_PATHWAY | 0.16597734 |
| INOS_ALL_DN | 0.16606128 |
| MAMMARY_DEV_UP | 0.16707349 |
| AS3_FIBRO_C1 | 0.16727026 |
| HASLINGER_B_CLL_12 | 0.1673312 |
| AGEING_KIDNEY_UP | 0.16749705 |
| AS3_FIBRO_C2 | 0.16755186 |
| PASSERINI_SIGNAL | 0.1677289 |
| ATRBRCAPATHWAY | 0.16775142 |
| TPA_RESIST_EARLY_DN | 0.16782525 |
| OXSTRESS_RPE_H2O2TBH_DN | 0.1678344 |
| P53_BRCA1_UP | 0.1678418 |
| CELL_ADHESION | 0.16795067 |
| HSA00310_LYSINE_DEGRADATION | 0.16802531 |
| TGFBETA_LATE_UP | 0.16803889 |
| HSA05222_SMALL_CELL_LUNG_CANCER | 0.1701583 |
| RAC1PATHWAY | 0.17040874 |
| HDACI_COLON_SUL30MIN_DN | 0.17152873 |
| MOREAUX_TACI_HI_IN_PPC_UP | 0.17201042 |
| GLYCEROLIPID_METABOLISM | 0.17364457 |

SUPPLEMENTAL TABLE 2-continued

Full list of pathways up-regulated (FDR < 0.25) in ischemic vs. non-ischemic
tissue from untreated BALB/C mice (based on GSEA analysis of mRNA arrays).

| NAME | FDR q-val |
| --- | --- |
| STOSSI_ER_UP | 0.17372909 |
| HDACI_COLON_CLUSTER9 | 0.17434259 |
| NF90_UP | 0.17454778 |
| KLEIN_PEL_DN | 0.17564699 |
| PARK_MSCS_DIFF | 0.1757411 |
| ADIP_HUMAN_DN | 0.1757531 |
| RIBAVIRIN_RSV_UP | 0.17576809 |
| TENEDINI_MEGAKARYOCYTIC_GENES | 0.17580557 |
| CMV_IE86_UP | 0.17582427 |
| CROONQUIST_IL6_RAS_DN | 0.1759441 |
| TSA_HEPATOMA_UP | 0.17594522 |
| NFKBPATHWAY | 0.17603053 |
| ROSS_CBF_LEUKEMIA | 0.1761407 |
| GALE_FLT3ANDAPL_UP | 0.17615002 |
| ADIP_DIFF_CLUSTER2 | 0.17622577 |
| POMEROY_MD_TREATMENT_GOOD_VS_POOR_DN | 0.17623748 |
| HSA04080_NEUROACTIVE_LIGAND_RECEPTOR_INTERACTION | 0.1763555 |
| HADDAD_CD45CD7_PLUS_VS_MINUS_DN | 0.1767668 |
| HSA04612_ANTIGEN_PROCESSING_AND_PRESENTATION | 0.17696081 |
| HADDAD_HSC_CD7_DN | 0.17705052 |
| ADIP_DIFF_CLUSTER1 | 0.17716199 |
| HDACI_COLON_BUT_UP | 0.17736544 |
| HSA00100_BIOSYNTHESIS_OF_STEROIDS | 0.17781189 |
| SERUM_FIBROBLAST_CORE_DN | 0.17786564 |
| TSA_HEPATOMA_CANCER_UP | 0.17787606 |
| SMITH_HCV_INDUCED_HCC_UP | 0.17789568 |
| HSC_INTERMEDIATEPROGENITORS_ADULT | 0.18001235 |
| GO_ROS | 0.18005292 |
| S1P_SIGNALING | 0.18021575 |
| NADLER_OBESITY_UP | 0.18025519 |
| BAF57_BT549_UP | 0.18033901 |
| LIAN_MYELOID_DIFF_GRANULE | 0.18042083 |
| GNATENKO_PLATELET_UP | 0.18045807 |
| PASSERINI_INFLAMMATION | 0.18059188 |
| CALRES_MOUSE_NEOCORTEX_UP | 0.18062651 |
| GNATENKO_PLATELET | 0.1807396 |
| XPB_TTD-CS_UP | 0.18079405 |
| HSA04514_CELL_ADHESION_MOLECULES | 0.18083291 |
| DAC_BLADDER_UP | 0.18086575 |
| UVB_NHEK1_UP | 0.18093763 |
| TSA_CD4_UP | 0.1810399 |
| GPCRDB_CLASS_A_RHODOPSIN_LIKE | 0.18107054 |
| HALMOS_CEBP_DN | 0.181276 |
| HSA05220_CHRONIC_MYELOID_LEUKEMIA | 0.18175948 |
| BRCA1_MES_UP | 0.18191634 |
| MUNSHI_MM_UP | 0.1823359 |
| BHATTACHARYA_ESC_UP | 0.18247174 |
| WNTPATHWAY | 0.18253918 |
| HSA00530_AMINOSUGARS_METABOLISM | 0.18265657 |
| CERAMIDEPATHWAY | 0.1828597 |
| FLECHNER_KIDNEY_TRANSPLANT_WELL_UP | 0.18293731 |
| KANG_TERT_UP | 0.18365723 |
| OVARIAN_INFERTILITY_GENES | 0.18385155 |
| GH_GHRHR_KO_6HRS_DN | 0.18395166 |
| LIAN_MYELOID_DIFF_RECEPTORS | 0.18399741 |
| TAKEDA_NUP8_HOXA9_10D_DN | 0.18440002 |
| CHOLESTEROL_BIOSYNTHESIS | 0.1847759 |
| HSA04540_GAP_JUNCTION | 0.1848347 |
| TAVOR_CEBP_DN | 0.18556434 |
| HSA00500_STARCH_AND_SUCROSE_METABOLISM | 0.1856034 |
| PLATELET_EXPRESSED | 0.18569198 |
| AGEING_BRAIN_UP | 0.186651 |
| DIAB_NEPH_UP | 0.1866737 |
| BCNU_GLIOMA_MGMT_48HRS_DN | 0.18687859 |
| AGED_MOUSE_CEREBELLUM_DN | 0.1874551 |
| HSA00030_PENTOSE_PHOSPHATE_PATHWAY | 0.18766026 |
| WONG_IFNA_HCC_RESISTANT_VS_SENSITIVE_DN | 0.18778451 |
| DFOSB_BRAIN_8WKS_UP | 0.18808551 |
| HADDAD_HPCLYMPHO_ENRICHED | 0.18845524 |
| HBX_HEP_UP | 0.18865947 |
| BOQUEST_CD31PLUS_VS_CD31MINUS_DN | 0.18866067 |
| TCELL_ANERGIC_UP | 0.19079365 |
| HSA00260_GLYCINE_SERINE_AND_THREONINE_METABOLISM | 0.19159348 |
| CCR3PATHWAY | 0.1915958 |
| HCC_SURVIVAL_GOOD_VS_POOR_DN | 0.1916092 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
| --- | --- |
| CASPASEPATHWAY | 0.19174318 |
| ROS_MOUSE_AORTA_DN | 0.1917559 |
| H2O2_CSBRESCUED_C1_UP | 0.19181655 |
| HDACI_COLON_CUR_UP | 0.19189991 |
| CANCER_NEOPLASTIC_META_UP | 0.19196437 |
| UV_UNIQUE_FIBRO_UP | 0.19258218 |
| GAMMA-UV_FIBRO_DN | 0.19291615 |
| NING_COPD_UP | 0.19328448 |
| BENNETT_SLE_UP | 0.1938234 |
| IGF1_NIH3T3_UP | 0.19403242 |
| CROONQUIST_RAS_STROMA_UP | 0.19477823 |
| HIVNEFPATHWAY | 0.19495702 |
| CARIES_PULP_HIGH_UP | 0.19508535 |
| CROMER_HYPOPHARYNGEAL_MET_VS_NON_UP | 0.1951668 |
| TAKEDA_NUP8_HOXA9_3D_DN | 0.19658327 |
| STANELLE_E2F1_UP | 0.1978441 |
| VEGF_MMMEC_6HRS_UP | 0.1991934 |
| APOPTOSIS | 0.19987626 |
| APOPTOSIS_GENMAPP | 0.19989651 |
| CROMER_HYPOPHARYNGEAL_MET_VS_NON_DN | 0.20057206 |
| PASSERINI_PROLIFERATION | 0.20094965 |
| LEE_ACOX1_UP | 0.20226721 |
| BRENTANI_CYTOSKELETON | 0.20314501 |
| ADIPOGENESIS_HMSC_CLASS3_UP | 0.20336221 |
| FRASOR_ER_DN | 0.20343539 |
| PASSERINI_ADHESION | 0.20356679 |
| PASSERINI_EM | 0.20358007 |
| DAC_FIBRO_UP | 0.20428288 |
| FLOTHO_CASP8AP2_MRD_DIFF | 0.20437786 |
| UVC_HIGH_D7_DN | 0.20440628 |
| HSC_INTERMEDIATEPROGENITORS_SHARED | 0.20462373 |
| CMV_HCMV_TIMECOURSE_14HRS_DN | 0.20476495 |
| BASSO_HCL_DIFF | 0.20574453 |
| GAMMA_ESR_WS_UNREG | 0.2057917 |
| IGF_VS_PDGF_DN | 0.20666905 |
| CROONQUIST_IL6_RAS_UP | 0.20723964 |
| IRS_KO_ADIP_DN | 0.20752625 |
| FLECHNER_KIDNEY_TRANSPLANT_WELL_PBL_UP | 0.2093802 |
| APPEL_IMATINIB_UP | 0.2107771 |
| HSA05214_GLIOMA | 0.21128817 |
| BRCA2_BRCA1_UP | 0.21251862 |
| HSA04360_AXON_GUIDANCE | 0.21335466 |
| PARK_HSC_VS_MPP_UP | 0.21349284 |
| LIZUKA_L0_SM_L1 | 0.21357848 |
| KERATINOCYTEPATHWAY | 0.21368635 |
| N_GLYCAN_BIOSYNTHESIS | 0.21369067 |
| METPATHWAY | 0.21382597 |
| HIPPOCAMPUS_DEVELOPMENT_PRENATAL | 0.21384783 |
| TGFBETA_C1_UP | 0.21391122 |
| HSA01031_GLYCAN_STRUCTURES_BIOSYNTHESIS_2 | 0.2139361 |
| HSA04010_MAPK_SIGNALING_PATHWAY | 0.21404946 |
| FLECHNER_KIDNEY_TRANSPLANT_REJECTION_PBL_DN | 0.21407354 |
| LIAN_MYELOID_DIFF_TF | 0.21415913 |
| ECMPATHWAY | 0.21429983 |
| CMV_HCMV_TIMECOURSE_1HR_DN | 0.21430913 |
| INSULIN_SIGNALING | 0.21436907 |
| RORIE_ES_PNET_UP | 0.21459675 |
| IDX_TSA_DN_CLUSTER2 | 0.21487209 |
| UEDA_MOUSE_SCN | 0.2150408 |
| TNF_AND_FAS_NETWORK | 0.21509545 |
| STRESS_GENOTOXIC_SPECIFIC_DN | 0.21512306 |
| NTHIPATHWAY | 0.21542308 |
| AGED_RHESUS_DN | 0.21564633 |
| HANSON_NFKAPPB_IND | 0.21593153 |
| HDACI_COLON_CLUSTER6 | 0.21621247 |
| HSA05219_BLADDER_CANCER | 0.21648672 |
| HSA01430_CELL_COMMUNICATION | 0.21658385 |
| HSA04510_FOCAL_ADHESION | 0.21669702 |
| AGUIRRE_PANCREAS_CHR12 | 0.2168742 |
| SMITH_HTERT_DN | 0.21999177 |
| ST_PHOSPHOINOSITIDE_3_KINASE_PATHWAY | 0.2200618 |
| JECHLINGER_EMT_DN | 0.22019191 |
| CELL_ADHESION_RECEPTOR_ACTIVITY | 0.22155796 |
| GOLDRATH_CYTOLYTIC | 0.22161815 |
| TNFR2PATHWAY | 0.2216969 |

SUPPLEMENTAL TABLE 2-continued

Full list of pathways up-regulated (FDR < 0.25) in ischemic vs. non-ischemic tissue from untreated BALB/C mice (based on GSEA analysis of mRNA arrays).

| NAME | FDR q-val |
|---|---|
| CMV-UV_HCMV_6HRS_DN | 0.2218287 |
| JAIN_NEMO_DIFF | 0.22184545 |
| HSC_HSC_FETAL | 0.2220867 |
| VERNELL_PRB_CLSTR1 | 0.2223137 |
| BUT_TSA_UP | 0.22237343 |
| CHEN_HOXA5_TARGETS_DN | 0.22312076 |
| HDACI_COLON_CUR_DN | 0.22334173 |
| STRESS_ARSENIC_SPECIFIC_DN | 0.22519669 |
| PENTOSE_PHOSPHATE_PATHWAY | 0.22524716 |
| MMS_MOUSE_LYMPH_HIGH_24HRS_UP | 0.22597119 |
| MENSSEN_MYC_UP | 0.22597916 |
| HADDAD_HSC_CD10_UP | 0.2260113 |
| CROONQUIST_RAS_STROMA_DN | 0.2262417 |
| NAB_LUNG_UP | 0.2264721 |
| ST_GA12_PATHWAY | 0.22669226 |
| BRG1_ALAB_DN | 0.22756894 |
| HDACI_COLON_SUL16HRS_DN | 0.22758031 |
| HSA00510_N_GLYCAN_BIOSYNTHESIS | 0.22761597 |
| TNFALPHA_30MIN_UP | 0.22775866 |
| FETAL_LIVER_ENRICHED_TRANSCRIPTION_FACTORS | 0.22872427 |
| INOSITOL_PHOSPHATE_METABOLISM | 0.22881456 |
| MANALO_HYPOXIA_UP | 0.2289087 |
| HSA01032_GLYCAN_STRUCTURES_DEGRADATION | 0.2289546 |
| KLEIN_PEL_UP | 0.22988707 |
| HSA04210_APOPTOSIS | 0.22989124 |
| UV-4NQO_FIBRO_UP | 0.23033006 |
| SIG_REGULATION_OF_THE_ACTIN_CYTOSKELETON_BY_RHO_GTPASES | 0.23105277 |
| ZHAN_MM_CD138_HP_VS_REST | 0.23247305 |
| INSULIN_NIH3T3_UP | 0.23272075 |
| TGFBETA_C5_UP | 0.23543428 |
| PURINE_METABOLISM | 0.23597485 |
| GH_AUTOCRINE_UP | 0.23621017 |
| BRENTANI_IMMUNE_FUNCTION | 0.23727974 |
| AGUIRRE_PANCREAS_CHR1 | 0.2383487 |
| WNT_SIGNALING | 0.23855525 |
| CHEN_HOXA5_TARGETS_UP | 0.23858711 |
| HSA04610_COMPLEMENT_AND_COAGULATION_CASCADES | 0.23873012 |
| GH_AUTOCRINE_DN | 0.2394122 |
| RIBAVIRIN_RSV_DN | 0.24160875 |
| SMITH_HTERT_UP | 0.24165125 |
| HSA04630_JAK_STAT_SIGNALING_PATHWAY | 0.24340692 |
| STRESS_ARSENIC_SPECIFIC_UP | 0.24574614 |
| TSADAC_PANC50_UP | 0.24603078 |
| HSA00561_GLYCEROLIPID_METABOLISM | 0.2464587 |
| ZHAN_MM_CD138_CD1_VS_REST | 0.24645932 |
| CELL_ADHESION_MOLECULE_ACTIVITY | 0.2464768 |
| INOS_ALL_UP | 0.24656406 |
| LEE_CIP_UP | 0.24662143 |
| CALCINEURIN_NF_AT_SIGNALING | 0.2466587 |
| RHOPATHWAY | 0.24722067 |

BIBLIOGRAPHY

1. He L, Hannon G J. MicroRNAs: small RNAs with a big role in gene regulation. *Nat Rev Genet.* 2004; 5:522-531.
2. Sun W, Julie Li Y S, Huang H D, Shyy J Y, Chien S. microRNA: a master regulator of cellular processes for bioengineering systems. *Annu Rev Biomed Eng.* 2010; 12:1-27.
3. Yang W J, Yang D D, Na S, Sandusky G E, Zhang Q, Zhao G. Dicer is required for embryonic angiogenesis during mouse development. *J Biol Chem.* 2005; 280:9330-9335.
4. Lee K H, Chen Y L, Yeh S D, Hsiao M, Lin J T, Goan Y G, Lu P J. MicroRNA-330 acts as tumor suppressor and induces apoptosis of prostate cancer cells through E2F1-mediated suppression of Akt phosphorylation. *Oncogene.* 2009; 28:3360-3370.
5. Niu J, Shi Y, Tan G, Yang C H, Fan M, Pfeffer L M, Wu Z H. DNA damage induces NF-kappaB-dependent microRNA-21 upregulation and promotes breast cancer cell invasion. *J Biol Chem.* 2012; 287:21783-21795.
6. Ozen M, Creighton C J, Ozdemir M, Ittmann M. Widespread deregulation of microRNA expression in human prostate cancer. *Oncogene.* 2008; 27:1788-1793.
7. Ueda T, Volinia S, Okumura H, Shimizu M, Taccioli C, Rossi S, Alder H, Liu C G, Oue N, Yasui W, Yoshida K, Sasaki H, Nomura S, Seto Y, Kaminishi M, Calin G A, Croce C M. Relation between microRNA expression and progression and prognosis of gastric cancer: a microRNA expression analysis. *Lancet Oncol.* 2010; 11:136-146.
8. Bonauer A, Carmona G, Iwasaki M, Mione M, Koyanagi M, Fischer A, Burchfield J, Fox H, Doebele C, Ohtani K, Chavakis E, Potente M, Tjwa M, Urbich C, Zeiher A M, Dimmeler S. MicroRNA-92a controls angiogenesis and functional recovery of ischemic tissues in mice. *Science.* 2009; 324:1710-1713.
9. Grundmann S, Hans F P, Kinniry S, Heinke J, Helbing T, Bluhm F, Sluijter J P, Hoefer I, Pasterkamp G, Bode C, Moser M. MicroRNA-100 regulates neovascularization by suppression of mammalian target of rapamycin in endothelial and vascular smooth muscle cells. *Circulation*. 2011; 123:999-1009.

10. Yin K J, Olsen K, Hamblin M, Zhang J, Schwendeman S P, Chen Y E. Vascular endothelial cell-specific microRNA-15a inhibits angiogenesis in hindlimb ischemia. *J Biol Chem*. 2012; 287:27055-27064.

11. Dokun A O, Keum S, Hazarika S, Li Y, Lamonte G M, Wheeler F, Marchuk D A, Annex B H. A quantitative trait locus (LSq-1) on mouse chromosome 7 is linked to the absence of tissue loss after surgical hindlimb ischemia. *Circulation*. 2008; 117:1207-1215.

12. Chalothorn D, Clayton J A, Zhang H, Pomp D, Faber J E. Collateral density, remodeling, and VEGF-A expression differ widely between mouse strains. *Physiol Genomics*. 2007; 30:179-191.

13. Helisch A, Wagner S, Khan N, Drinane M, Wolfram S, Heil M, Ziegelhoeffer T, Brandt U, Pearlman J D, Swartz H M, Schaper W. Impact of mouse strain differences in innate hindlimb collateral vasculature. *Arterioscler Thromb Vasc Biol*. 2006; 26:520-526.

14. Li Y, Hazarika S, Xie D, Pippen A M, Kontos C D, Annex B H. In mice with type 2 diabetes, a vascular endothelial growth factor (VEGF)-activating transcription factor modulates VEGF signaling and induces therapeutic angiogenesis after hindlimb ischemia. *Diabetes*. 2007; 56:656-665.

15. Hazarika S, Dokun A O, Li Y, Popel A S, Kontos C D, Annex B H. Impaired angiogenesis after hindlimb ischemia in type 2 diabetes mellitus: differential regulation of vascular endothelial growth factor receptor 1 and soluble vascular endothelial growth factor receptor 1. *Circ Res*. 2007; 101:948-956.

16. Team R D C. R: A language and environment for statistical computing: R Foundation for Statistical Computing; 2009:1-409.

17. Dunning M J, Smith M L, Ritchie M E, Tavare S. beadarray: R classes and methods for Illumina bead-based data. *Bioinformatics*. 2007; 23:2183-2184.

18. Subramanian A, Tamayo P, Mootha V K, Mukherjee S, Ebert B L, Gillette M A, Paulovich A, Pomeroy S L, Golub T R, Lander E S, Mesirov J P. Gene set enrichment analysis: a knowledge-based approach for interpreting genome-wide expression profiles. *Proc Natl Acad Sci USA*. 2005; 102:15545-15550.

19. Krutzfeldt J, Rajewsky N, Braich R, Rajeev K G, Tuschl T, Manoharan M, Stoffel M. Silencing of microRNAs in vivo with 'antagomirs'. *Nature*. 2005; 438:685-689.

20. Ge Y, Sun Y, Chen J. IGF-II is regulated by microRNA-125b in skeletal myogenesis. *J Cell Biol*. 2011; 192:69-81.

21. Fang L, Deng Z, Shatseva T, Yang J, Peng C, Du W W, Yee A J, Ang L C, He C, Shan S W, Yang B B. MicroRNA miR-93 promotes tumor growth and angiogenesis by targeting integrin-beta8. *Oncogene*. 2011; 30:806-821.

22. Long J, Wang Y, Wang W, Chang B H, Danesh F R. Identification of microRNA-93 as a novel regulator of vascular endothelial growth factor in hyperglycemic conditions. *J Biol Chem*. 2010; 285:23457-23465.

23. Ivanovska I, Ball A S, Diaz R L, Magnus J F, Kibukawa M, Schelter J M, Kobayashi S V, Lim L, Burchard J, Jackson A L, Linsley P S, Cleary M A. MicroRNAs in the miR-106b family regulate p21/CDKN1A and promote cell cycle progression. *Mol Cell Biol*. 2008; 28:2167-2174.

24. Petrocca F, Vecchione A, Croce C M. Emerging role of miR-106b-25/miR-17-92 clusters in the control of transforming growth factor beta signaling. *Cancer Res*. 2008; 68:8191-8194.

25. Fu X, Tian J, Zhang L, Chen Y, Hao Q. Involvement of microRNA-93, a new regulator of PTEN/Akt signaling pathway, in regulation of chemotherapeutic drug cisplatin chemosensitivity in ovarian cancer cells. *FEBS Lett*. 2012; 586:1279-1286.

26. Toyokawa G, Masuda K, Daigo Y, Cho H S, Yoshimatsu M, Takawa M, Hayami S, Maejima K, Chino M, Field H I, Neal D E, Tsuchiya E, Ponder B A, Maehara Y, Nakamura Y, Hamamoto R. Minichromosome Maintenance Protein 7 is a potential therapeutic target in human cancer and a novel prognostic marker of non-small cell lung cancer. *Mol Cancer*. 2011; 10:65-66.

27. Dong Y B, Yang H L, Elliott M J, Liu T J, Stilwell A, Atienza C, Jr., McMasters K M. Adenovirus-mediated E2F-1 gene transfer efficiently induces apoptosis in melanoma cells. *Cancer*. 1999; 86:2021-2033.

28. Shan B, Lee W H. Deregulated expression of E2F-1 induces S-phase entry and leads to apoptosis. *Mol Cell Biol*. 1994; 14:8166-8173.

29. Qin G, Kishore R, Dolan C M, Silver M, Wecker A, Luedemann C N, Thorne T, Hanley A, Curry C, Heyd L, Dinesh D, Kearney M, Martelli F, Murayama T, Goukassian D A, Zhu Y, Losordo D W. Cell cycle regulator E2F1 modulates angiogenesis via p53-dependent transcriptional control of VEGF. *Proc Natl Acad Sci USA*. 2006; 103:11015-11020.

30. Stempien-Otero A, Karsan A, Cornejo C J, Xiang H, Eunson T, Morrison R S, Kay M, Winn R, Harlan J. Mechanisms of hypoxia-induced endothelial cell death. Role of p53 in apoptosis. *J Biol Chem*. 1999; 274:8039-8045.

31. Wang J X, Jiao J Q, Li Q, Long B, Wang K, Liu J P, Li Y R, Li P F. miR-499 regulates mitochondrial dynamics by targeting calcineurin and dynamin-related protein-1. *Nat Med*. 2011; 17:71-78.

32. Ventura A, Young A G, Winslow M M, Lintault L, Meissner A, Erkeland S J, Newman J, Bronson R T, Crowley D, Stone J R, Jaenisch R, Sharp P A, Jacks T. Targeted deletion reveals essential and overlapping functions of the miR-17 through 92 family of miRNA clusters. *Cell*. 2008; 132:875-886.

33. Li Y, Tan W, Neo T W, Aung M O, Wasser S, Lim S G, Tan T M. Role of the miR-106b-25 microRNA cluster in hepatocellular carcinoma. *Cancer Sci*. 2009; 100:1234-1242.

34. Hubbi M E, Luo W, Baek J H, Semenza G L. MCM proteins are negative regulators of hypoxia-inducible factor 1. *Mol Cell*. 2011; 42:700-712.

35. Manalo D J, Rowan A, Lavoie T, Natarajan L, Kelly B D, Ye S Q, Garcia J G, Semenza G L. Transcriptional regulation of vascular endothelial cell responses to hypoxia by HIF-1. *Blood*. 2005; 105:659-669.

What is claimed is:

1. A method of treating or preventing a disease, disorder, injury, or condition associated with skeletal muscle ischemia, wherein said disease, disorder, injury, or condition is peripheral arterial disease, said method comprising administering to a subject a pharmaceutical composition comprising an effective amount of an agonist of miRNA expression, levels, or activity, a pharmaceutically-acceptable carrier, wherein said miRNA is miR-93, and optionally an additional therapeutic agent, thereby treating said disease, disorder, or condition associated with ischemia.

2. The method of claim 1, wherein said agonist of miR-93 is selected from the group of isolated nucleic acids consisting of a nucleic acid comprising a nucleic acid sequence encoding a precursor miR-93, a nucleic acid comprising a nucleic acid sequence encoding a mature miR-93, a nucleic acid comprising a precursor miR-93, and a nucleic acid comprising a mature miR-93, and biologically active fragments or homologs thereof.

3. The method of claim 2, wherein said isolated nucleic acid is a precursor miR-93, and biologically active fragments or homologs thereof.

4. The method of claim 2, wherein said isolated nucleic acid is a mature miR-93, and biologically active fragments or homologs thereof.

5. The method of claim 2, wherein said isolated nucleic acid is a deoxyribonucleic acid.

6. The method of claim 2, wherein said isolated nucleic acid is a ribonucleic acid.

7. The method of claim 3, wherein said sequences encoding miR-93 or comprising mir-93 microRNA are selected from the group consisting of SEQ NOs:1, 2, 5, 6, 7, 8, 9, and 10, and biologically active fragments and homologs thereof.

8. The method of claim 1, wherein said agonist increases miR-93 expression, levels, or activity.

9. The method of claim 8, wherein said agonist is an miR-93 mimic.

10. The method of claim 7, wherein said isolated nucleic acid is encoded by a vector.

11. The method of claim 10, wherein said vector is an expression vector selected from an miRNA expression vector or AAV expression vector.

12. The method of claim 11, wherein said expression vector is an miRNA expression vector.

13. The method of claim 10, wherein said isolated nucleic acid is operably-linked to a cell-specific promoter.

14. The method of claim 10, wherein a lipid vehicle comprises said isolated nucleic acid.

15. The method of claim 1, wherein said additional therapeutic agent comprises an anti-ischemia agent.

16. The method of claim 1, wherein said method decreases expression of at least one cell cycle pathway gene.

17. The method of claim 16, wherein said cell cycle pathway genes are selected from the group consisting of p21, E2F-1, and p53.

18. The method of claim 16, wherein expression of at least two of p21, EF-1, and p53 decreases.

19. The method of claim 1, wherein expression or levels of at least one of VEGF-A, PTEN, MCM-7, TGF-β1, Epiregulin, BMP-2, ATP8b, Dusp-4, and integrin β8 do not change.

20. The method of claim 16, wherein said expression is in skeletal muscle cells.

21. The method of claim 1, wherein said agonist is incorporated into a skeletal muscle cell or an endothelial cell.

22. The method of claim 1, wherein said agonist incorporates into at least one skeletal muscle cell and at least one endothelial cell.

23. The method of claim 1, wherein said method enhances perfusion recovery.

24. The method of claim 1, wherein said method enhances the angiogenic response to ischemia.

25. The method of claim 1, wherein said method stimulates cell proliferation.

26. The method of claim 25, wherein said cell is an endothelial cell or a skeletal muscle cell.

27. The method of claim 1, wherein said method increases capillary density.

28. The method of claim 1, wherein said method reduces apoptosis.

29. The method of claim 28, wherein said apoptosis is hypoxia-induced apoptosis.

30. The method of claim 1, wherein said administration is by a route selected from the group consisting of oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, rectal, intrasternal injection, kidney dialytic infusion, and parenteral.

31. The method of claim 30, wherein said administration is intramuscular.

32. The method of claim 1, wherein said agonist is administered at a frequency selected from the group consisting of at least once a day, twice a day, three times a day, four times a day, once a week, twice a week, once a month, and twice a month.

33. The method of claim 1, wherein said subject is a human.

34. The method of claim 1, wherein at least two agonists are administered.

35. The method of claim 1, wherein said treatment is prophylactic.

36. The method of claim 1, wherein said ischemia is selected from the group consisting of vascular ischemia, peripheral arterial disease, and brain ischemia.

\* \* \* \* \*

SEQUENCE LISTING

<160> NUMBER OF SEQ ID NOS: 10

<210> SEQ ID NO 1
<211> LENGTH: 80
<212> TYPE: DNA
<213> ORGANISM: Homo sapiens

<400> SEQUENCE: 1 ctggggctc caaagtgctg ttcgtgcagg tagtgtgatt acccaaccta ctgctgagct    60
agcacttccc gagcccccgg                                              80

<210> SEQ ID NO 2
<211> LENGTH: 22
<212> TYPE: DNA
<213> ORGANISM: Homo sapiens

<400> SEQUENCE: 2
aaagtgctgt tcgtgcaggt ag                                           22

<210> SEQ ID NO 3
<211> LENGTH: 23
<212> TYPE: RNA
<213> ORGANISM: Homo sapiens

<400> SEQUENCE: 3
cuaccugcac gaacagcacu uug                                          23

<210> SEQ ID NO 4
<211> LENGTH: 23
<212> TYPE: RNA
<213> ORGANISM: homo sapiens

<400> SEQUENCE: 4
cuaccugcac gaacagcacu uug                                          23

<210> SEQ ID NO 5
<211> LENGTH: 80
<212> TYPE: RNA
<213> ORGANISM: Homo sapiens

<400> SEQUENCE: 5 cuggggcuc caaagugcug uucgugcagg uagugugauu acccaaccua cugcugagcu    60
agcacuuccc gagcccccgg                                              80

<210> SEQ ID NO 6
<211> LENGTH: 22
<212> TYPE: RNA
<213> ORGANISM: Homo sapiens

<400> SEQUENCE: 6
aaagugcugu ucgugcaggu ag                                           22

<210> SEQ ID NO 7
<211> LENGTH: 23
<212> TYPE: RNA
<213> ORGANISM: Homo sapiens

<400> SEQUENCE: 7
caaagugcug uucgugcagg uag                                          23

```
<210> SEQ ID NO 8
<211> LENGTH: 22
<212> TYPE: RNA
<213> ORGANISM: Homo sapiens

<400> SEQUENCE: 8
acugcugagc uagcacuucc cg                                              22

<210> SEQ ID NO 9
<211> LENGTH: 80
<212> TYPE: RNA
<213> ORGANISM: Homo sapiens

<400> SEQUENCE: 9 cuggggcuc caaagugcug uucgugcagg uagugugauu acccaaccua cugcugagcu      60
agcacuuccc gagccccgg                                                  80

<210> SEQ ID NO 10
<211> LENGTH: 22
<212> TYPE: RNA
<213> ORGANISM: Homo sapiens

<400> SEQUENCE: 10
aaagugcugu ucgugcaggu ag                                              22
```